United States Patent
Zitvogel et al.

(10) Patent No.: US 10,646,521 B2
(45) Date of Patent: May 12, 2020

(54) MICROBIOTA COMPOSITION, AS A MARKER OF RESPONSIVENESS TO CHEMOTHERAPY, AND USE OF MICROBIAL MODULATORS (PRE-, PRO- OR SYNBIOTICS) FOR IMPROVING THE EFFICACY OF A CANCER TREATMENT

(71) Applicants: INSTITUT GUSTAVE ROUSSY, Villejuif (FR); UNIVERSITÉ PARIS—SACLAY, Saint Aubin (FR); INSTITUT NATIONAL DE LA SANTÉ ET DE LA RECHERCHE MÉDICALE, Paris (FR); INSTITUT DE LA RECHERCHE AGRONOMIQUE, Paris (FR)

(72) Inventors: Laurence Zitvogel, Paris (FR); Ivo Gomperts Boneca, Vitry sur Seine (FR); Patricia Lepage, Chatillon (FR); Sophie Viaud, Paris (FR); Romain Daillere, Villejuif (FR)

(73) Assignees: INSTITUT GUSTAVE ROUSSY, Villejuif (FR); UNIVERSITÉ PARIS—SACLAY, Saint Aubin (FR); INSTITUT NATIONAL DE LA SANTÉ ET DE LA RECHERCHE MÉDICALE, Paris (FR); INSTITUT DE LA RECHERCHE AGRONOMIQUE, Paris (FR)

( * ) Notice: Subject to any disclaimer, the term of this patent is extended or adjusted under 35 U.S.C. 154(b) by 117 days.

(21) Appl. No.: 15/038,073

(22) PCT Filed: Nov. 21, 2014

(86) PCT No.: PCT/IB2014/066249
§ 371 (c)(1),
(2) Date: May 20, 2016

(87) PCT Pub. No.: WO2015/075688
PCT Pub. Date: May 28, 2015

(65) Prior Publication Data
US 2016/0303172 A1 Oct. 20, 2016

Related U.S. Application Data

(60) Provisional application No. 61/907,076, filed on Nov. 21, 2013.

(30) Foreign Application Priority Data

Nov. 21, 2013 (EP) .................................. 13306597

(51) Int. Cl.
*A61K 35/744* (2015.01)
*A61K 35/741* (2015.01)
*A61K 35/747* (2015.01)
*A61K 39/39* (2006.01)
*C12R 1/46* (2006.01)
*A61K 39/00* (2006.01)

(52) U.S. Cl.
CPC .......... *A61K 35/744* (2013.01); *A61K 35/741* (2013.01); *A61K 35/747* (2013.01); *C12R 1/46* (2013.01); *A61K 2039/55594* (2013.01)

(58) Field of Classification Search
CPC ...... C12N 1/20; A61K 31/739; A61K 39/116; G01N 33/569
See application file for complete search history.

(56) References Cited

FOREIGN PATENT DOCUMENTS

| WO | 2008/141240 A1 | 11/2008 |
|---|---|---|
| WO | 2010/033426 A2 | 9/2009 |
| WO | 2010/033424 A2 | 3/2010 |
| WO | 2010/033425 A2 | 3/2010 |
| WO | 2011/131472 A1 | 10/2011 |

OTHER PUBLICATIONS

Takada et al. Infect. Immun. 63: 57-65, 1995.*
Abe et al. Ann. N.Y. Acad. Sci. 685: 372-374, 1993.*
Shibata et al. J. Bacteriol. 174: 6117-6124, 1992.*
Abe et al. Jpn. J. Cancer Res. (Gann) 76: 626-630, 1985.*
Glick. Enterococcus faecalis, pp. 1-2, 2005.*
Tsutsui et al. FEMS Microbiol. Immunol. 3: 211-218, 1991.*
'Lentinan', Wolters Kluwer Health, 2009.*
Reisser et al. BioEssays 24: 284-289, 2002.*
Osterlund P et al: "Lactobacillus supplementation for diarrhoea related to chemotherapy of colorectal cancer: A randomised study", British Journal of Cancer, Nature Publishing Group, GB, vol. 97, No. 8, Oct. 22, 2007 (Oct. 22, 2007), pp. 1028-1034.
Alex Sparreboom et al: "Mechanisms of Action of Cancer Chemotherapeutic Agents: Antitumour Antibiotics" In: "The Cancer Handbook", Jan. 1, 2002 (Jan. 1, 2002), John Wiley & Sons, Ltd, Chichester, UK, ISBN: 978-0-47-002507-9 DOI: 10.1002/0470025077. chap84e.

(Continued)

*Primary Examiner* — Sarvamangala Devi
(74) *Attorney, Agent, or Firm* — Arrigo, Lee, Guttman & Mouta-Bellum, LLP

(57) ABSTRACT

The present invention provides methods for determining if a patient is likely to benefit from a cancer treatment, by determining if said patient has a gut dysbiosis with an over representation of certain bacterial species. The present invention also provides probiotic strains to improve the efficacy of a cancer treatment, especially chemotherapy, in patients in need thereof.

Figure 1A:
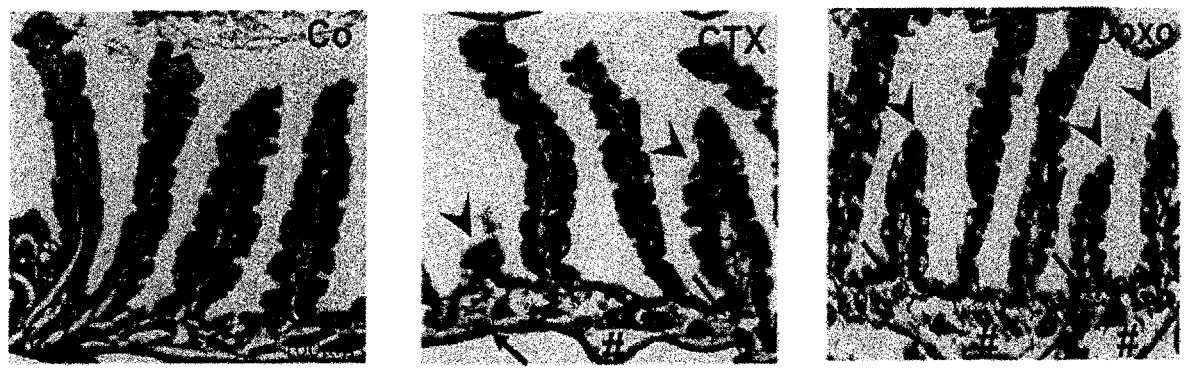

20 Claims, 53 Drawing Sheets
Specification includes a Sequence Listing.

(56) References Cited

OTHER PUBLICATIONS

Kirsty C. Newman et al: "Whatever turns you on: accessory-cell-dependent activation of NK cells by pathogens", Nature Reviews Immunology, vol. 7, No. 4, Apr. 1, 2007 (Apr. 1, 2007), pp. 279-291.

Jutta Zwielehner et al: "Changes in Human Fecal Microbiota Due to Chemotherapy Analyzed by TaqMan-PCR, 454 Sequencing and PCR-DGGE Fingerprinting", PLOS ONE, vol. 6, No. 12, Dec. 14, 2011 (Dec. 14, 2011), p. e28654.

Hannah R Wardill et al: "Chemotherapy-induced gut toxicity: are alterations to intestinal tight junctions pivotal?", Cancer Chemotherapy and Pharmacology, Springer, Berlin, DE, vol. 70, No. 5, Sep. 30, 2012 (Sep. 30, 2012), pp. 627-635.

S. Viaud et al: "The Intestinal Microbiota Modulates the Anticancer Immune Effects of Cyclophosphamide", Science, vol. 342, No 6161, Nov. 21, 2013 (Nov. 21, 2013), pp. 971-976.

N. Iida et al: "Commensal Bacteria Control Cancer Response to Therapy by Modulating the Tumor Microenvironment", Science, vol. 342, No. 6161, Nov. 21, 2013 (Nov. 21, 2013), pp. 967-970.

E. Miyauchi et al: "Cell wall fraction of Enterococcus hirae ameliorates TNF-[alpha]-induced barrier impairment in the human epithelial tight junction", Letters in Applied Microbiology, vol. 46, No. 4, Apr. 1, 2008 (Apr. 1, 2008), pp. 469-476.

Sophie Viaud et al: "Why should we need the gut microbiota to respond to cancer therapies?", Oncoimmunology, vol. 3, No. 1, Jan. 1, 2014 (Jan. 1, 2014), p. e27574.

Keller, R., et al., "Macrophage Response to Bacteria: Induction of Marked Secretory and Cellular Activities by Lipoteichoic Acids," Infection and Immunity, vol. 60, No. 9, pp. 3664-3672 (1992).

Routy, B., et al., "Gut microbiome influences efficacy of PD-1-based immunotherapy against epithelial tumors," Science 10.1126/science.aan3706 (2017).

Ying, H.U., et al., "Fermentation Characteristics of Enterococcus hirae and Applications thereof," Journal of Dairy Science and Technology 2012, vol. 35 No. 1 p. 15-19.

Zitvogel, L., et al., "The anticancer immune response: indispensable for therapeutic success?" J. Clin. Invest. 118:1991-2001 (2008). doi:10.1172/JCI35180.

* cited by examiner

- ☐ *L. johnsonii*
- ■ *L. murinus*
- ▨ *E. hirae*
- ☐ *L. intestinalis*
- ■ *L. reuteri*

Comp1=9.18%
Comp2=8.26%

Monte-Carlo test
Observation: 0.05645551

Based on 999 replicates
Simulated p-value: 0.018

| | OT_ID | 1stHit_Sab_score |
|---|---|---|
| FECES | | |
| Increased in DKO_CTX | denovo1095 | 0.974 |
| | denovo527 | 0.964 |
| | denovo2207 | 0.99 |
| | denovo2583 | 0.989 |
| | denovo1890 | 0.987 |
| | denovo1247 | 0.987 |
| | denovo1435 | 0.979 |
| | denovo1425 | 0.997 |
| | denovo500 | 0.987 |
| | denovo922 | 0.972 |
| | denovo1248 | 0.988 |
| | denovo2049 | 1 |
| | denovo1427 | 1 |
| | denovo944 | 0.994 |
| | denovo1466 | 0.992 |
| | denovo66 | 0.924 |
| | denovo586 | 0.987 |
| Decreased in DKO_CTX | denovo210 | 0.991 |
| | denovo322 | 0.973 |
| | denovo1068 | 0.978 |
| | denovo321 | 1 |
| | denovo2284 | 0.973 |
| | denovo448 | 1 |
| | denovo1092 | 1 |
| | denovo1758 | 0.964 |
| | denovo740 | 0.984 |
| ILEUM | | |
| Increased in DKO_CTX | denovo1119 | 1 |
| | denovo891 | 0.975 |
| Decreased in DKO_CTX | denovo139 | 0.99 |
| | denovo183 | 0.988 |
| | denovo2 | 0.946 |
| | denovo123 | 0.864 |
| | denovo1163 | 0.968 |
| | denovo247 | 0.98 |
| | denovo9 | 1 |

*FIG. 40*

| 1stHit_sequence_name | Sab_score_relative |
|---|---|
| uncultured organism; ELU0008-T58-S-NI_000347; HQ740254 | 0.679 |
| uncultured bacterium; TLR1KO1.4C8_8F; JF912749 | 0.814 |
| uncultured bacterium; 16saw30-1f03.w2k; EF602764 | 0.651 |
| Gram-negative bacterium cL10-2b-4; AY239469 | 0.989 |
| uncultured bacterium; C12_M13; AY989974 | 0.672 |
| uncultured bacterium; L7-2; AJ400249 | 0.741 |
| uncultured bacterium; K78S4_31b02; EU456737 | 0.679 |
| uncultured bacterium; molerat_aai71f08; EU463206 | 0.726 |
| uncultured bacterium; C12_B13; AY989991 | 0.718 |
| uncultured bacterium; HFDE2558FC11; JQ893123 | 0.702 |
| uncultured bacterium; S26-9; AJ308395 | 0.740 |
| uncultured bacterium; lean2_aaa03b03; EF096057 | 0.683 |
| uncultured bacterium; 16sms100-2e08; JF245898 | 0.992 |
| uncultured bacterium; K78S2_44d09; EU451570 | 0.751 |
| segmented filamentous bacterium; X77814 | 0.992 |
| uncultured bacterium; S30-4; AJ400241 | 0.662 |
| uncultured bacterium; 16saw31-1g05.w2k; EF602844 | 0.629 |
| uncultured bacterium; C20_c05; AY991747 | 0.870 |
| uncultured bacterium; C23_e07; AY992451 | 0.852 |
| uncultured bacterium; C11_G031; AY991574 | 0.963 |
| uncultured bacterium; 16saw39-1f04.w2k; EF604615 | 0.900 |
| uncultured bacterium; nby247g05c1; HM808026 | 0.837 |
| uncultured bacterium; WD4_aal38f11; EU510442 | 0.903 |
| uncultured bacterium; C13-5; AJ308396 | 0.915 |
| uncultured bacterium; M1_b04_2; DQ014737 | 0.903 |
| uncultured bacterium; YO00276F08; FJ837703 | 0.875 |
| | |
| segmented_filamentous_bacterium_X77814 | 1.000 |
| uncultured_bacterium_CRWD2_aaa04c11_EU503767 | 0.716 |
| uncultured_bacterium_16saw30_1f03w2k_EF602764 | 0.651 |
| uncultured_bacterium_S26_9_AJ308395 | 0.740 |
| uncultured_bacterium_DE05987D03_JQ694965 | 0.651 |
| uncultured_bacterium_C16_B17_AY992192 | 0.689 |
| uncultured_bacterium_obob1_aaa02c05_EF096190 | 0.968 |
| uncultured_bacterium_aaa49d07_DQ817835 | 0.975 |
| uncultured_bacterium_H77S2_33b09_EU454901 | 0.799 |

*FIG. 40 (CONT.)*

| sequence_name_relati | phylum | family |
|---|---|---|
| Gram-negative bacterium cTPY-13; AY239461 | Bacteroidetes | Porphyromonadaceae |
| Gram-negative bacterium cL10-2b-4; AY239469 | Bacteroidetes | Porphyromonadaceae |
| Barnesiella intestinihominis (T); YIT 11860; AB370251 | Bacteroidetes | Porphyromonadaceae |
| Gram-negative bacterium cL10-2b-4; AY239469 | Bacteroidetes | Porphyromonadaceae |
| Gram-negative bacterium cL10-2b-4; AY239469 | Bacteroidetes | Porphyromonadaceae |
| Gram-negative bacterium cL10-2b-4; AY239469 | Bacteroidetes | Porphyromonadaceae |
| Porphyromonas sp. MI10-1288x; HM583587 | Bacteroidetes | Porphyromonadaceae |
| Gram-negative bacterium cL10-2b-4; AY239469 | Bacteroidetes | Porphyromonadaceae |
| Gram-negative bacterium cL10-2b-4; AY239469 | Bacteroidetes | Porphyromonadaceae |
| Alloprevotella rava; F0323; GU470887 | Bacteroidetes | Prevotellaceae |
| Parasutterella excrementihominis (T); YIT 11859 | Proteobacteria | Sutterellaceae |
| Gram-negative bacterium cL10-2b-4; AY239469 | Bacteroidetes | Porphyromonadaceae |
| Lactobacillus murinus; ONS2; AY324630 | Firmicutes | Lactobacillaceae |
| Gram-negative bacterium cTPY-13; AY239461 | Bacteroidetes | Porphyromonadaceae |
| segmented filamentous bacterium; X77814 | Firmicutes | Clostridiaceae 1 |
| Gram-negative bacterium cL10-2b-4; AY239469 | Bacteroidetes | Porphyromonadaceae |
| Barnesiella sp. 177; KJ572412 | Bacteroidetes | Porphyromonadaceae |
| Clostridium aldenense (T); RMA 9741; DQ279736 | Firmicutes | Lachnospiraceae |
| Clostridium sp. Culture Jar-8; AB622825 | Firmicutes | Ruminococcaceae |
| Clostridium sp. Clone-17; AB622837 | Firmicutes | Lachnospiraceae |
| Clostridium sp. ASF356; ASF 356; AF157052 | Firmicutes | Lachnospiraceae |
| Clostridium populeti (T); ATCC 35295; X71853 | Firmicutes | Lachnospiraceae |
| unidentified bacterium; CCCM41; AY654953 | Firmicutes | Lachnospiraceae |
| Clostridium sp. ASF502; ASF 502; AF157053 | Firmicutes | Lachnospiraceae |
| Clostridium oroticum; type strain: DSM 1287; 6; FR749922 | Firmicutes | Lachnospiraceae |
| Oscillibacter sp. G2; HM626173 | Firmicutes | Ruminococcaceae |
| | | |
| segmented_filamentous_bacterium_X77814 | Firmicutes | Clostridiaceae_1 |
| Clostridium_sp_ID4_AY960571 | Firmicutes | Erysipelotrichaceae |
| Barnesiella_intestinihominis_YIT_11860_AB370251 | Bacteroidetes | Porphyromonadaceae |
| Parasutterella_excrementihominis_YIT_11859__JCM_15078__DS | Proteobacteria | Sutterellaceae |
| Barnesiella_intestinihominis_YIT_11860_AB370251 | Bacteroidetes | Porphyromonadaceae |
| Barnesiella_intestinihominis_YIT_11860_AB370251 | Bacteroidetes | Porphyromonadaceae |
| Clostridium_sp_Culture_54_AB622823 | Firmicutes | Lachnospiraceae |
| Staphylococcus_lentus_PLC_6_AY161045 | Firmicutes | Staphylococcaceae |
| Clostridium_leptum_DSM_753T_AJ305238 | Firmicutes | Ruminococcaceae |

*FIG. 40 (CONT. 1)*

| | | Mean | | | | p-value (t-test) | |
|---|---|---|---|---|---|---|---|
| genus | WT_CTX | WT | DKO_CTX | DKO | WT_CTX vs WT | DKO_CTX vs DKO | WT_CTX vs DKO_CTX |
| unclassified_"Porphyromonadaceae" | 3.548 | 0.003 | 21.396 | 5.188 | 0.374 | 0.020 | 0.016 |
| Barnesiella | 0.002 | 0.000 | 7.907 | 0.669 | 0.374 | 0.002 | 0.003 |
| Barnesiella | 6.410 | 4.997 | 8.890 | 3.839 | 0.696 | 0.027 | 0.335 |
| Barnesiella | 1.392 | 1.105 | 5.437 | 0.534 | 0.868 | 0.041 | 0.092 |
| Barnesiella | 0.148 | 0.003 | 2.773 | 0.485 | 0.383 | 0.047 | 0.032 |
| Barnesiella | 0.431 | 1.263 | 1.844 | 0.382 | 0.274 | 0.004 | 0.005 |
| Porphyromonas | 1.102 | 1.225 | 1.968 | 0.565 | 0.880 | 0.007 | 0.173 |
| Barnesiella | 0.865 | 2.466 | 1.632 | 0.321 | 0.412 | 0.001 | 0.075 |
| Barnesiella | 0.711 | 0.501 | 1.708 | 0.567 | 0.643 | 0.018 | 0.079 |
| Alloprevotella | 0.489 | 1.706 | 1.062 | 0.155 | 0.534 | 0.020 | 0.298 |
| Parasutterella | 0.490 | 0.384 | 0.964 | 0.120 | 0.772 | 0.004 | 0.085 |
| Barnesiella | 0.391 | 0.457 | 0.900 | 0.282 | 0.862 | 0.022 | 0.163 |
| Lactobacillus | 0.194 | 0.404 | 0.430 | 0.036 | 0.408 | 0.048 | 0.226 |
| unclassified_"Porphyromonadaceae" | 0.019 | 0.000 | 0.265 | 0.036 | 0.374 | 0.038 | 0.031 |
| unclassified_Clostridiaceae 1 | 0.000 | 0.000 | 0.199 | 0.000 | na | 0.038 | 0.038 |
| Barnesiella | 0.016 | 0.035 | 0.080 | 0.007 | 0.540 | 0.032 | 0.048 |
| Barnesiella | 0.057 | 0.025 | 0.087 | 0.024 | 0.266 | 0.018 | 0.253 |
| Clostridium XlVa | 0.262 | 0.059 | 0.045 | 1.047 | 0.140 | 0.015 | 0.113 |
| Clostridium IV | 0.223 | 0.210 | 0.000 | 0.300 | 0.947 | 0.037 | 0.259 |
| unclassified_Lachnospiraceae | 0.022 | 0.010 | 0.000 | 0.152 | 0.454 | 0.015 | 0.145 |
| Clostridium XlVb | 0.148 | 0.100 | 0.034 | 0.155 | 0.580 | 0.033 | 0.105 |
| Clostridium XlVa | 0.000 | 0.019 | 0.000 | 0.095 | 0.391 | 0.012 | na |
| unclassified_Lachnospiraceae | 0.060 | 0.112 | 0.008 | 0.100 | 0.633 | 0.003 | 0.070 |
| unclassified_Lachnospiraceae | 0.039 | 0.065 | 0.000 | 0.044 | 0.700 | 0.036 | 0.312 |
| Clostridium XlVa | 0.054 | 0.006 | 0.000 | 0.033 | 0.250 | 0.029 | 0.199 |
| Oscillibacter | 0.022 | 0.013 | 0.005 | 0.033 | 0.609 | 0.048 | 0.247 |
| | | | | | | | |
| unclassified_Clostridiaceae_1 | 0.386 | 0.058 | 6.913 | 1.248 | 0.402 | 0.053 | 0.030 |
| Allobaculum | 0.000 | 0.000 | 0.016 | 0.001 | na | 0.041 | 0.029 |
| Barnesiella | 8.331 | 5.164 | 2.258 | 5.201 | 0.378 | 0.049 | 0.110 |
| Parasutterella | 1.475 | 1.554 | 0.522 | 1.101 | 0.900 | 0.004 | 0.041 |
| Barnesiella | 0.059 | 0.046 | 0.017 | 0.075 | 0.660 | 0.051 | 0.097 |
| Barnesiella | 0.047 | 0.013 | 0.023 | 0.077 | 0.106 | 0.033 | 0.235 |
| unclassified_Lachnospiraceae | 0.018 | 0.034 | 0.007 | 0.032 | 0.350 | 0.028 | 0.309 |
| Staphylococcus | 0.000 | 0.000 | 0.001 | 0.021 | na | 0.021 | 0.356 |
| Clostridium_IV | 0.018 | 0.000 | 0.000 | 0.009 | 0.202 | 0.037 | 0.202 |

*FIG. 40 (CONT. 2)*

SEQUENCE LISTING

```
<160> NUMBER OF SEQ ID NOS: 34

<210> SEQ ID NO 1
<211> LENGTH: 20
<212> TYPE: DNA
<213> ORGANISM: Artificial Sequence
<220> FEATURE:
<223> OTHER INFORMATION: Primer

<400> SEQUENCE: 1
```

```
agagtttgat catggctcag                                               20

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
aaggaggtga tccaaccgca                                               20

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
ctcctacggg aggcagcagt                                               20

<210> SEQ ID NO 4
<211> LENGTH: 18
<212> TYPE: DNA
<213> ORGANISM: Artificial Sequence
<220> FEATURE:
<223> OTHER INFORMATION: Primer

<400> SEQUENCE: 4
gcatgtggtt taattcga                                                 18

<210> SEQ ID NO 5
<211> LENGTH: 15
<212> TYPE: DNA
<213> ORGANISM: Artificial Sequence
<220> FEATURE:
<223> OTHER INFORMATION: Primer

<400> SEQUENCE: 5
tacggraggc agcag                                                    15

<210> SEQ ID NO 6
<211> LENGTH: 19
<212> TYPE: DNA
<213> ORGANISM: Artificial Sequence
<220> FEATURE:
<223> OTHER INFORMATION: Primer

<400> SEQUENCE: 6
ggactaccag ggtatctaa                                                19

<210> SEQ ID NO 7
<211> LENGTH: 19
<212> TYPE: DNA
<213> ORGANISM: Artificial Sequence
<220> FEATURE:
<223> OTHER INFORMATION: Primer

<400> SEQUENCE: 7
atggagggga atacagccc                                                19

<210> SEQ ID NO 8
<211> LENGTH: 20
<212> TYPE: DNA
<213> ORGANISM: Artificial Sequence
```

```
<220> FEATURE:
<223> OTHER INFORMATION: Primer

<400> SEQUENCE: 8
ttctttgcag ctccttcgtt                                              20

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
ccaggatact gagggcatgt                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
cttatcagtt ggcgtttggg                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
cctgtgcaag aagcagagtg                                              20

<210> SEQ ID NO 12
<211> LENGTH: 20
<212> TYPE: DNA
<213> ORGANISM: Artificial Sequence
<220> FEATURE:
<223> OTHER INFORMATION: Primer

<400> SEQUENCE: 12
gttctgctga ttccccttcc                                              20

<210> SEQ ID NO 13
<211> LENGTH: 16
<212> TYPE: DNA
<213> ORGANISM: Artificial Sequence
<220> FEATURE:
<223> OTHER INFORMATION: Primer

<400> SEQUENCE: 13
ggccgatgac gagccc                                                  16

<210> SEQ ID NO 14
<211> LENGTH: 23
<212> TYPE: DNA
<213> ORGANISM: Artificial Sequence
<220> FEATURE:
<223> OTHER INFORMATION: Primer

<400> SEQUENCE: 14
tgtctttgga actttgtctg caa                                          23
```

<210> SEQ ID NO 15
<211> LENGTH: 20
<212> TYPE: DNA
<213> ORGANISM: Artificial Sequence
<220> FEATURE:
<223> OTHER INFORMATION: Primer

<400> SEQUENCE: 15
cagcaccacc tctacgaaca                                              20

<210> SEQ ID NO 16
<211> LENGTH: 20
<212> TYPE: DNA
<213> ORGANISM: Artificial Sequence
<220> FEATURE:
<223> OTHER INFORMATION: Primer

<400> SEQUENCE: 16
cgccaccaaa ctgagatgat                                              20

<210> SEQ ID NO 17
<211> LENGTH: 20
<212> TYPE: DNA
<213> ORGANISM: Artificial Sequence
<220> FEATURE:
<223> OTHER INFORMATION: Primer

<400> SEQUENCE: 17
ctcgtctgaa ggcagagtca                                              20

<210> SEQ ID NO 18
<211> LENGTH: 20
<212> TYPE: DNA
<213> ORGANISM: Artificial Sequence
<220> FEATURE:
<223> OTHER INFORMATION: Primer

<400> SEQUENCE: 18
tggcagagag gtattgaggg                                              20

<210> SEQ ID NO 19
<211> LENGTH: 20
<212> TYPE: DNA
<213> ORGANISM: Artificial Sequence
<220> FEATURE:
<223> OTHER INFORMATION: Primer

<400> SEQUENCE: 19
aggatgtccc tgctctcctt                                              20

<210> SEQ ID NO 20
<211> LENGTH: 20
<212> TYPE: DNA
<213> ORGANISM: Artificial Sequence
<220> FEATURE:
<223> OTHER INFORMATION: Primer

<400> SEQUENCE: 20
gcctgcggac tctaccataa                                              20

<210> SEQ ID NO 21
<211> LENGTH: 20
<212> TYPE: DNA
<213> ORGANISM: Artificial Sequence
<220> FEATURE:
<223> OTHER INFORMATION: Primer

```
<400> SEQUENCE: 21
tgagctcatt gaatgcttgg                                                      20

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
acagcaaggc gaaaaaggat                                                      20

<210> SEQ ID NO 23
<211> LENGTH: 21
<212> TYPE: DNA
<213> ORGANISM: Artificial Sequence
<220> FEATURE:
<223> OTHER INFORMATION: Primer

<400> SEQUENCE: 23
tgtcaaattc attcatggcc t                                                    21

<210> SEQ ID NO 24
<211> LENGTH: 20
<212> TYPE: DNA
<213> ORGANISM: Artificial Sequence
<220> FEATURE:
<223> OTHER INFORMATION: Primer

<400> SEQUENCE: 24
atcgatttct cccctgtgaa                                                      20

<210> SEQ ID NO 25
<211> LENGTH: 20
<212> TYPE: DNA
<213> ORGANISM: Artificial Sequence
<220> FEATURE:
<223> OTHER INFORMATION: Primer

<400> SEQUENCE: 25
tgagcttccc agatcacaga                                                      20

<210> SEQ ID NO 26
<211> LENGTH: 20
<212> TYPE: DNA
<213> ORGANISM: Artificial Sequence
<220> FEATURE:
<223> OTHER INFORMATION: Primer

<400> SEQUENCE: 26
tccagaaggc cctcagacta                                                      20

<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ggtgataacc ccgtagtgga                                                      20

<210> SEQ ID NO 28
```

-continued

```
<210> SEQ ID NO 28
<211> LENGTH: 20
<212> TYPE: DNA
<213> ORGANISM: Artificial Sequence
<220> FEATURE:
<223> OTHER INFORMATION: Primer

<400> SEQUENCE: 28
ctgcaaagaa gacccacacc                                              20

<210> SEQ ID NO 29
<211> LENGTH: 20
<212> TYPE: DNA
<213> ORGANISM: Artificial Sequence
<220> FEATURE:
<223> OTHER INFORMATION: Primer

<400> SEQUENCE: 29
atcctgtaat ggcttgtggg                                              20

<210> SEQ ID NO 30
<211> LENGTH: 20
<212> TYPE: DNA
<213> ORGANISM: Artificial Sequence
<220> FEATURE:
<223> OTHER INFORMATION: Primer

<400> SEQUENCE: 30
tcaaccagca ccagacagag                                              20

<210> SEQ ID NO 31
<211> LENGTH: 20
<212> TYPE: DNA
<213> ORGANISM: Artificial Sequence
<220> FEATURE:
<223> OTHER INFORMATION: Primer

<400> SEQUENCE: 31
caacccaggt ccttcctaaa                                              20

<210> SEQ ID NO 32
<211> LENGTH: 20
<212> TYPE: DNA
<213> ORGANISM: Artificial Sequence
<220> FEATURE:
<223> OTHER INFORMATION: Primer

<400> SEQUENCE: 32
ggagagccct ggataccaac                                              20

<210> SEQ ID NO 33
<211> LENGTH: 8
<212> TYPE: PRT
<213> ORGANISM: Artificial Sequence
<220> FEATURE:
<223> OTHER INFORMATION: control peptide

<400> SEQUENCE: 33

Ser Ile Ile Asn Phe Glu Lys Leu
1               5

<210> SEQ ID NO 34
<211> LENGTH: 20
<212> TYPE: PRT
<213> ORGANISM: Artificial Sequence
<220> FEATURE:
<223> OTHER INFORMATION: CBir1- peptide 455-475
```

```
<400> SEQUENCE: 34

Asp Met Ala Thr Glu Met Val Lys Tyr Ser Asn Ala Asn Ile Leu Ser
1               5                   10                  15

Gln Ala Gly Gln
            20
```

MICROBIOTA COMPOSITION, AS A MARKER OF RESPONSIVENESS TO CHEMOTHERAPY, AND USE OF MICROBIAL MODULATORS (PRE-, PRO- OR SYNBIOTICS) FOR IMPROVING THE EFFICACY OF A CANCER TREATMENT

FIELD OF THE INVENTION

The present invention relates to the field of anticancer treatment. In particular, the present invention concerns the role of the microbiota in the efficacy of cancer treatments, and provides methods for determining if a patient is likely to benefit from a cancer treatment, as well as probiotics to improve the efficacy of such a treatment in patients in need thereof.

BACKGROUND AND PRIOR ART

Conventional cancer treatments involve a combination of chemotherapy, surgery, hormonal therapy and/or radiation treatment to eradicate neoplastic cells in a patient. Cancer chemotherapy is based on the use of drugs which kill replicating cells, hopefully faster than the agents kill the patient's normal cells. Surgery is used to reduce tumor bulk, but has little impact once the cancer has metastasized. Radiation is effective only in a localized area. All of these approaches pose significant drawbacks and added risks such as increased susceptibility to infection.

A further approach to cancer therapy is to target the immune system ("immunotherapy") rather than or in addition to targeting the tumor itself.

However, despite advances in detection and treatment, many therapeutic protocols make only a minor contribution to survival rates, raising into question the cost-effectiveness and impact on quality of life of such treatments.

Recently, the important contribution of the innate and adaptive immune systems to the antitumour effects of conventional chemotherapy-based and radiotherapy-based cancer treatments has been described (Kroemer et al., 2013; Zitvogel et al., 2008).

It is now well established that gut commensal bacteria profoundly shape mammalian immunity (Hooper et al., 20112). Intestinal dysbiosis, which constitutes a disequilibrium in the bacterial ecosystem, can lead to overrepresentation of some bacteria able to promote colon carcinogenesis by favoring chronic inflammation or local immunosuppression (Grivennikov et al., 2012; Wu et al., 2009). However, the effects of microbial dysbiosis on non-gastrointestinal cancers are unknown.

Anticancer chemotherapeutics often cause mucositis (a debilitating mucosal barrier injury associated with bacterial translocation) and neutropenia, two complications that require treatment with antibiotics, which in turn can result in dysbiosis (Ubeda et al., 2010; van Vliet et al., 2010).

There is therefore a compelling need for the development of improved treatments for cancer which favor a constructive interaction, if not a synergy, between treatments such as chemotherapy and/or radiation and immunity.

SUMMARY OF THE INVENTION

In this context, the inventors observed that cyclophosphamide (CTX) alters the composition of small intestinal microbiota in mice and provokes the translocation of selected species of Gram+ bacteria into secondary lymphoid organs. There, these bacteria stimulate the generation of a specific subset of "pathogenic" T helper 17 (pTh17) cells and memory Th1 immune responses. The inventors also demonstrated that germ-free mice or hosts treated with antibiotics killing Gram+ bacteria exhibited reduced pTh17 responses and relative chemoresistance to CTX unless adoptively transferred with pTh17 cells. Moreover, dysbiosis interfered with the activity of other anticancer chemotherapeutics (such as anthracyclines and oxaliplatine). These results reveal a crucial role of the gut microbiota in shaping the anticancer immune response. These results, as well as other results related to the interaction between gut microbiota and antineoplastic treatments, are reviewed in severa recent publications (Dzutsev et al., 2014; Viaud et al., Cancer Res., 2014; Viaud et al., Cell Death Differ., 2014 and Viaud et al., Oncoimmunology, 2014).

The present invention provides a probiotic composition which can be used as an adjuvant to an antineoplastic treatment administered to a cancer patient, wherein said probiotic composition comprises bacteria selected amongst *Enterococcus hirae, Lactobacillus johnsonii*, segmented filamentous bacteria (SFB), *Porphyromonas, Barnesiella, Holdemania* and mixtures thereof.

Another aspect of the present invention is the use of a combination of a chemotherapeutic agent and of an antibiotic composition which decreases the firmicutes/bacteroidetes ratio or specifically augments SFB and/or Porphyromonadaceae and/or decreases *Clostridium* group IV in the gut microbiota of an individual when administered to said individual, for treating a patient having a cancer.

The invention also relates to the use of an antibiotic composition such as those described above, for modulating the gut microbiota of a patient to potentiate the anticancer effects of a chemotherapeutic agent administered to said patient.

An immunogenic composition comprising fragments of bacteria selected from the group consisting of *Enterococcus hirae, Lactobacillus johnsonii, Enterococcus faecalis*, segmented filamentous bacteria (SFB), *Porphyromonas, Barnesiella, Holdemania* and mixtures thereof is also part of the present invention, as well as its use as an adjuvant to an antineoplastic treatment administered to a cancer patient.

The invention further pertains to cell compositions and their use in adoptive cell transfer in combination with a chemotherapeutic agent. A first cell composition comprises antigen presenting cells (APC) which have been pulsed ex vivo with a probiotic composition or with an immunogenic composition as described above, and a second cell composition comprises memory T cells obtained by a process comprising ex vivo contacting T cells from a cancer patient with a first cell composition as defined above.

The present invention also provides an in vitro method of identifying a patient likely to be a good responder to a chemotherapy, comprising determining the functionality of TLR 4, NOD1 and NOD2 in said patient, wherein if said patient lacks a functional TLR 4 and/or NOD1 and/or NOD2, the patient is identified as a good responder to a chemotherapy.

The present invention also provides a method for in vitro determining whether a cancer patient can benefit from an antineoplastic treatment, comprising the following steps:

(i) from an appropriate biological sample from said patient, for example obtained from a biopsy of duodenum or ileum mucosae, or from a fecal sample from the patient, determining the relative abundance of "unfavorable" bacteria in the specific context of cancer treatment, for example bacteria from a group comprising or consisting of the species *Parabacteroides distasonis* and *Faecalibacterium*

*prausnitzii* and the genera *Gemmiger, Alistipes* and *Clostridium* cluster IV in said patient's gut microbiota;

(ii) determining the presence or absence of an intestinal dysbiosis;

wherein an intestinal dysbiosis with an over-representation of "unfavorable" bacteria indicates that the patient will not be a good responder to the antineoplastic treatment.

The present invention also provides a method for in vitro determining whether an antineoplastic treatment is to be continued or stopped for a cancer patient, comprising the following steps:

(i) from a biological sample from said patient, such as a blood sample obtained 3 to 9 weeks, preferably 6-9 weeks after the beginning of said antineoplastic treatment, analyzing memory CD4$^+$ T cell response directed against at least one commensal species of bacteria, for example against *L. johnsonii, E. hirae* and/or *E. Faecalis*;

(ii) for each commensal species against which the CD4$^+$ T cell response is analyzed, classifying the response in one of the following categories:

no memory CD4$^+$ T cell response;

memory response of a Th10 phenotype;

memory response of a Th1 phenotype, wherein if a memory response of a Th1 phenotype is observed for at least one commensal species, the antineoplastic treatment is continued, and in absence of such a response, the antineoplastic treatment is stopped.

The classification of the response can be performed, for example, by comparing pre- and post-treatment secretion of cytokines in ex vivo restimulation assays.

The present invention also pertains to a method for in vitro determining the biological effects of a neoadjuvant antineoplastic treatment which has been administered to a patient, comprising the following steps:

(i) from an appropriate biological sample from said patient, for example obtained from a biopsy of duodenum or ileum mucosae from the patient, determining the relative abundance of bacteria from a first group comprising *Lactobacillus* and *Bifidobacterium* genera in said microbiota;

(ii) from the same biological sample, determining the relative abundance of bacteria from a second group comprising *Parabacteroides distasonis, Faecalibacterium prausnitzii, Gemmiger, Alistipes* and *Clostridium* cluster IV in said gut microbiota;

(iii) calculating the ratio between the abundance of bacteria from the first group and the abundance of bacteria from the second group, wherein if said ratio is above a predetermined threshold, the result indicates that the neoadjuvant antineoplastic treatment induced a T-bet/Th1 local and systemic immune response.

Another object of the present invention is a probiotic bacterial strain selected from the group consisting of *Lactobacillus johnsonii* (especially strain CNCM I-4823), *Enterococcus hirae* (especially strain CNCM I-4815) and *Enterococcus faecalis*, for use in combination with an antineoplastic agent for inducing a T-bet/Th1 local and systemic immune response, as well as a composition comprising the same.

The invention also pertains to adoptive cell transfer of a cell obtained by stimulating naive CD4+ T cells from a cancer patient in the presence of a mixture of IL-1β, IL-6 and IL23, in said cancer patient, in combination with an antineoplastic treatment, for treating cancer.

LEGENDS TO THE FIGURES

FIG. 1: Cyclophosphamide disrupts gut mucosal integrity.

(A-B). Hematoxilin-eosin staining of the small intestine epithelium at 48 h post-NaCl (Co) or CTX or doxorubicin (Doxo) therapy in C57BL/6 naïve mice (A). The numbers of inflammatory foci depicted/mm (B, left panel, indicated with arrowhead on A), thickness of the lamina propria reflecting edema (B, middle panel, indicated with # on A) and the reduced length of villi (B, right panel, indicated with arrowhead in A) were measured in 5 ilea on 100 villi/ileum from CTX or Doxo-treated mice. (C). A representative microphotograph of an ileal villus containing typical mucin-containing goblet cells is shown in vehicle- and CTX or Doxo-treated mice (left panels). The number of goblet cells/villus was enumerated in the right panel for both chemotherapy agents. (D). Specific staining of Paneth cells is shown in two representative immunofluorescence microphotographs (D, left panels). The quantification of Paneth cells was performed measuring the average area of the lysozyme-positive clusters in 6 ilea harvested from mice treated with NaCl (Co) or CTX at 24-48 hours. (E). Quantitative PCR (qPCR) analyses of Lysozyme M and RegIIIγ transcription levels in duodenum and ileum lamina propria cells from mice treated with CTX at 18 hours. Means±SEM of normalized deltaCT of 3-4 mice/group concatenated from three independent experiments. (F). In vivo intestinal permeability assays measuring 4 kDa fluorescein isothiocyanate (FITC)-dextran plasma accumulation at 18 hours post-CTX at two doses. Graph showing all data from four independent experiments, each dot representing one mouse (n=13-15). Data were analyzed with the t-test. *, $p<0.05$, , $p<0.01$, *, $p<0.001$.

FIG. 2: Cyclophosphamide induces mucosa-associated microbial dysbiosis and bacterial translocation in secondary lymphoid organs.

(A-B). At 48 hours post-CTX or Doxo, mesenteric lymph node (mLN) and spleen cells from naïve mice were cultivated in aerobic and anaerobic conditions and colonies were enumerated (A) from each mouse treated with NaCl (Co) (n=10-16), CTX (n=12-27) or Doxo (n=3-17) (3-4 experiments) and identified by mass spectrometry (B). In NaCl controls, attempts of bacterial identification mostly failed and yielded 67% *Lactobacillus. murinus* (not shown). Data were analyzed with the t-test. (C). The microbial composition (genus level) was analyzed by 454 pyrosequencing of the 16S rRNA gene from ilea and caeca of naïve mice and B16F10 tumor bearers. Principal Component Analyses (PCA) highlighted specific clustering of mice microbiota (each dot represents one mouse) depending on the treatment (NaCl: Co, grey dots; CTX-treated, black dots). A Monte Carlo rank test was applied to assess the significance of these clusterings. (D). Quantitative PCR (qPCR) analyses of various bacterial groups associated with small intestine mucosa were performed on CTX or NaCl (Co)-treated, naïve or MCA205 tumor-bearing mice. Absolute values were calculated for total bacteria, Lactobacilli, Enterococci and *Clostridium* group IV and normalized by the dilution and weight of the sample. Standard curves were generated from serial dilutions of a known concentration of genomic DNA from each bacterial group and by plotting threshold cycles (Ct) vs. bacterial quantity (CFU). Points below the dotted lines were under the detection threshold. Data were analyzed with the linear model or generalized linear model. *, $p<0.5$, , $p<0.1$, *, $p<0.001$, ns, non significant.

FIG. 3: CTX-induced pTh17 effectors and memory Th1 responses depend on gut microbiota.

(A). Splenocytes from CTX versus NaCl treated animals reared in germ-free (GF) or conventional specific pathogen-free (SPF) conditions (left panel) and treated or not with ATB or vancomycin (Vanco) (right panel) were cross-linked using anti-CD3+anti-CD28 Ab for 48 h. IL-17 was measured by ELISA. Two to 3 experiments containing 2-9 mice/group are presented, each dot representing one mouse. (B). Correlations between the quantity of specific mucosal bacterial groups and the spleen Th17 signature. Each dot represents one mouse bearing no tumor (round dots), a B16F10 melanoma (diamond dots) or a MCA205 sarcoma (square dots), open dots featuring NaCl-treated mice and full dots indicating CTX-treated animals. (C). Intracellular analyses of splenocytes harvested from non-tumor-bearing mice after 7 days of either NaCl or CTX treatment, under ATB or water regimen as control. Means±SEM of percentages of IFN$\gamma^+$ Th17 cells, T-bet$^+$ cells among ROR$\gamma$t$^+$ CD4$^+$ T cells and CXCR3$^+$ cells among CCR6$^+$CD4$^+$ T cells in 2-8 independent experiments, each dot representing one mouse. (D) Intracellular staining of total splenocytes harvested 7 days post-CTX treatment from naïve mice orally-reconstituted with the indicated bacterial species after ATB treatment. (E). 7 days post CTX or NaCl (Co) treatment, splenic CD4$^+$ T cells were restimulated ex vivo with bone-marrow dendritic cells (BM-DCs) loaded with decreasing amounts of bacteria for 24 hours. IFN$\gamma$ release, monitored by ELISA, is shown. The numbers of responder mice (based on the NaCl baseline threshold) out of the total number of mice tested is indicated (n). Statistical comparisons were based on the paired t-test. Data were either analyzed with beta regression or linear model and correlation analyses from modified Kendall tau. *, p<0.05, ***, p<0.001, ns, non significant.

FIG. 4: Vancomycin blunts CTX-induced pTh17 differentiation which is mandatory for the tumoricidal activity of chemotherapy.

(A). After a 3 week-long pretreatment with broad-spectrum ATB, DBA2 mice were inoculated with P815 mastocytomas (day 0), treated at day 6 with CTX (arrow) and tumor growth was monitored. Tumor growth kinetics are shown in FIG. 13A and percentages of tumor-free mice at sacrifice are depicted for two experiments of 11-14 mice/group. (B). MCA205 sarcoma were inoculated at day 0 in specific pathogen-free (SPF) or germ-free (GF) mice that were optionally mono-associated with segmented filamentous bacteria (SFB), treated with CTX (arrow) and monitored for growth kinetics (means±SEM). One representative experiment (n=5-8 mice/group) out of two to three is shown for GF mice and two pooled experiments (n=14 mice/group) for SPF mice (C). After a 3 week-conditioning with vancomycin or colistin, C57BL/6 mice were inoculated with MCA205 sarcomas (day 0), treated at day 12-15 with CTX (arrow) and tumor growth was monitored. Concatenated data (n=15-20 mice/group) from two independent experiments are shown for colistin treatment and one representative experiment (n=6 mice/group) for vancomycin treatment. (D). Eight week-old KP (KrasLSL-G12D/WT; p53$^{Flox/Flox}$) mice received an adenovirus expressing the Cre recombinase (AdCre) by intranasal instillation to initiate lung adenocarcinoma (d0). Vancomycin was started for a subgroup of mice ("Chemo+Vanco") on d77 post-AdCre. One week after the start of vancomycin, CTX-based chemotherapy was applied i.p. to mice that only received chemotherapy ("Chemo") or those that received in parallel vancomycin ("Chemo+Vanco"). Mice received chemotherapy on d84, d91 and d98. A control group was left untreated ("Co"). Data show the evolution of total lung tumor volumes (mean±SEM) assessed by non invasive imaging between d73 and d100 in 6-12 mice/group. (E). As in FIG. 3C, the number of pTh17 cells in spleens from untreated or vancomycin treated mice bearing established (15-17 days) MCA205 tumors was determined, 7 days after CTX treatment. Each dot represents one mouse from 2 pooled experiments. (F). Flow cytometric analyses of CD3$^+$ and CD4$^+$IFN$\gamma^+$ T cells were performed by gating on CD45$^+$ live tumor-infiltrating lymphocytes (TILs) extracted from day 18 established MCA205 tumors (8 days post-CTX) in water or vancomycin-treated mice. Each dot representing one mouse from up to four pooled experiments. (G). MCA205 tumors established in WT mice pretreated for 3 weeks with water or vancomycin were injected with CTX (arrow), and tumor growth was monitored. At day 7 post-CTX, 3 million of ex vivo generated. Th17 or pTh17 CD4$^+$ T cells were injected intravenously. Up to three experiments comprising 2-10 mice/group were pooled. Data were either analyzed with the t-test, linear model or generalized linear model. *, p<0.5, , p<0.1, *, p<0.001, ns, non significant.

Figure 5A:
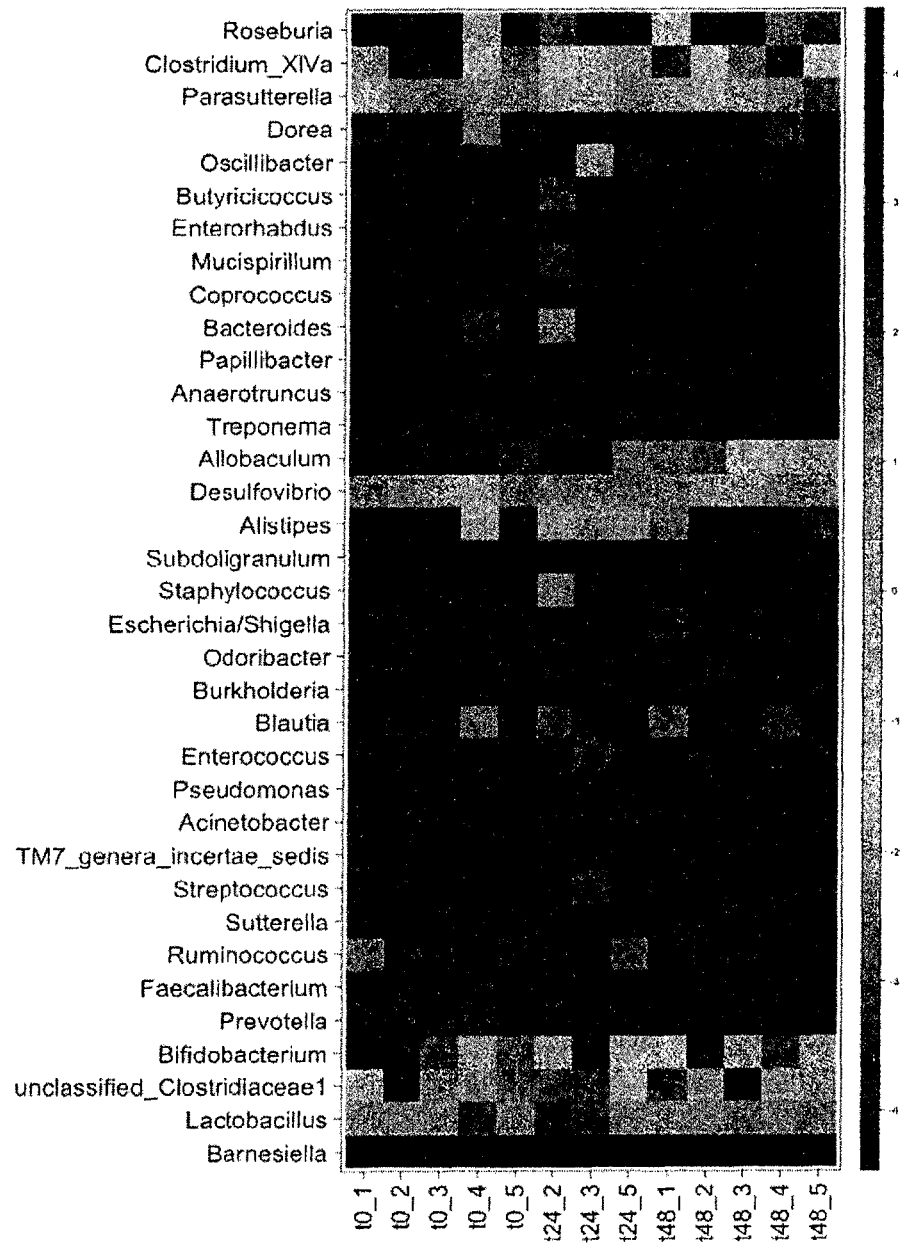
Figure 5B:
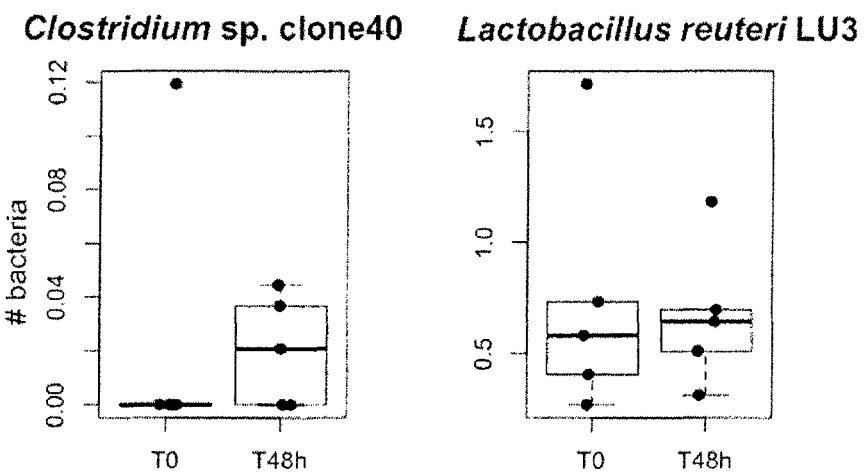
Figure 5C:
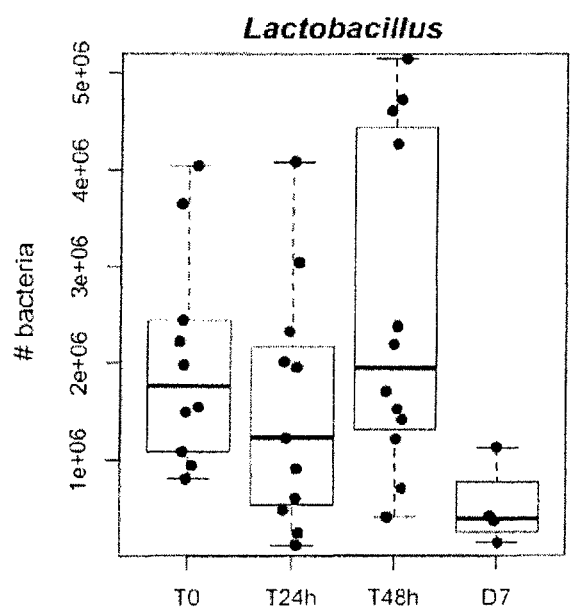

FIG. 5: Lack of dysbiosis 24 or 48 h post-CTX.

(A). Overall composition of the gut microbiota as assessed by high-throughput 454 pyrosequencing of the 16S rRNA gene at various time points (0, 24, 48 hours post-CTX). Each column represents data from one mouse small intestine mucosal microbiota, t0 (before CTX injection), t24 and t48 (24 and 48 hours post-CTX). The positive gradient of representativity of distinct genera (heatmap of the Log$_{10}$-transformation) is indicated. Statistical analyses: ns between t0 and t24 or t48 hrs. (B-C). Detailed example of the pyrosequencing data for *Clostridium* sp. clone 40 and for *L. reuteri*. qPCR analysis of Lactobacilli amounts overtime as detailed in Materials and Methods.

Figure 6:
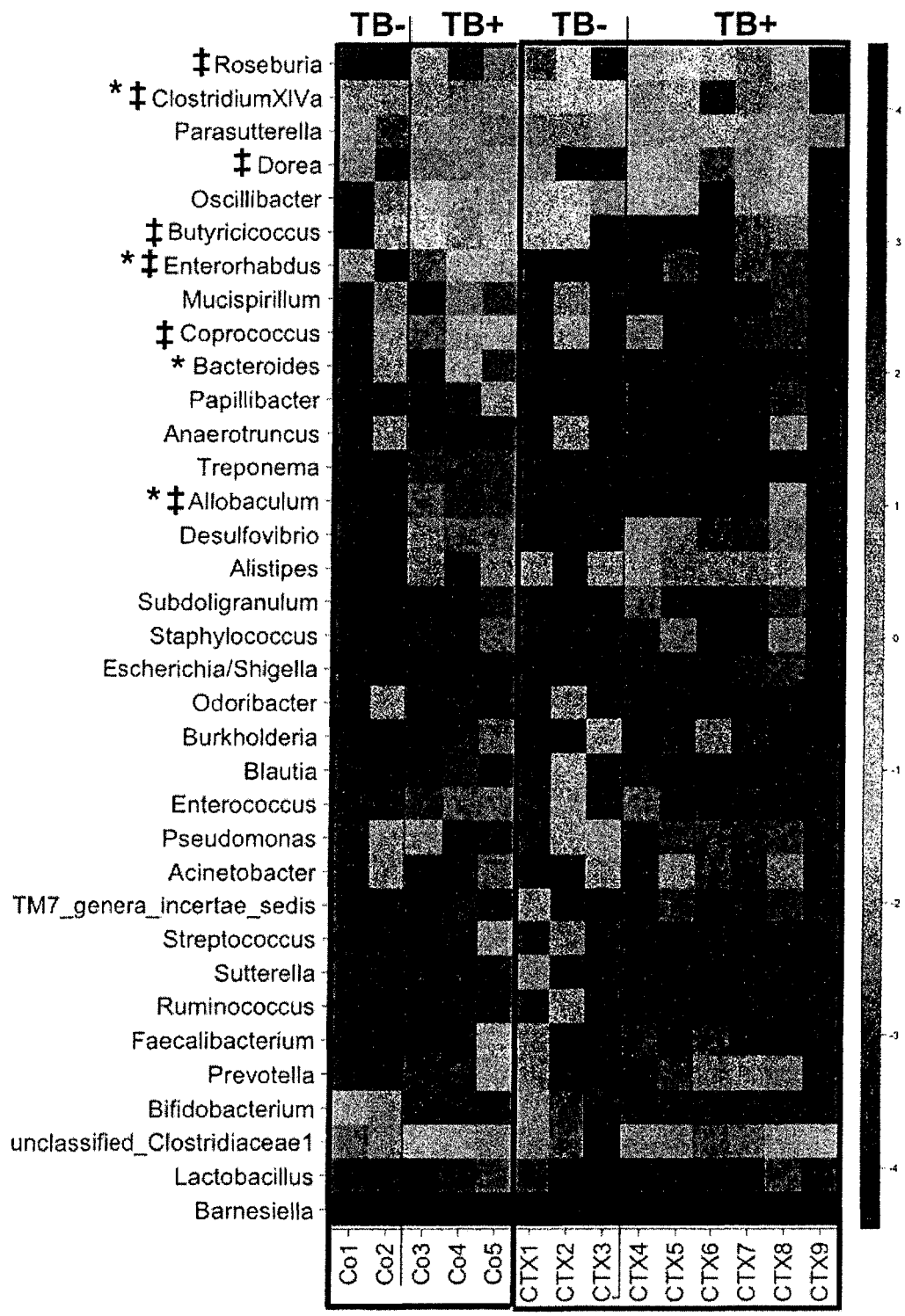

FIG. 6: Distribution of bacterial genera in the ileum of mice treated with CTX. Heatmap of the Log$_{10}$-transformation of relative abundance of genus in the small intestine from NaCl (Co) and CTX-treated animals. Prior to CTX therapy, tumors were inoculated in a subgroup of animals (TB+). Only bacterial genera representing more than 0.05% of the whole microbiota are presented. The applied log$_{10}$-transformation on relative abundances data has been explained in the microbiota Materials and Methods section. No specific clustering method has been applied for heatmap construction. Average delta of percentages between Co and CTX for each genus was calculated to re-order bacterial genera.

Figure 2A:
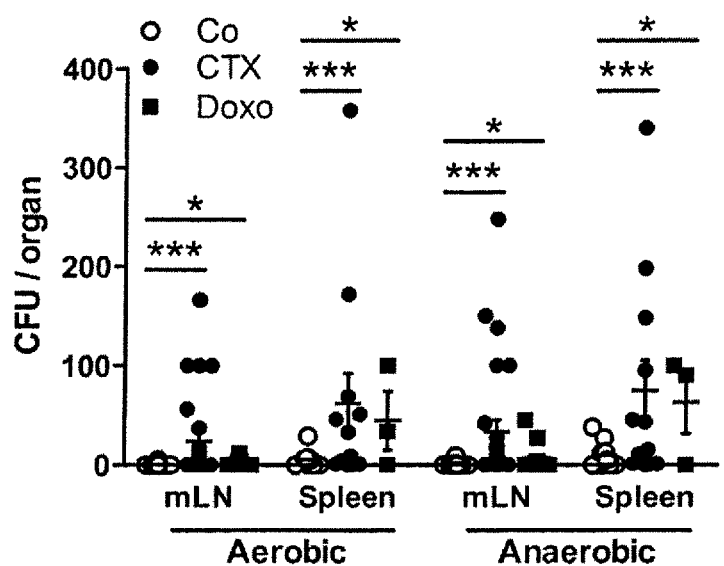
Figure 2B:
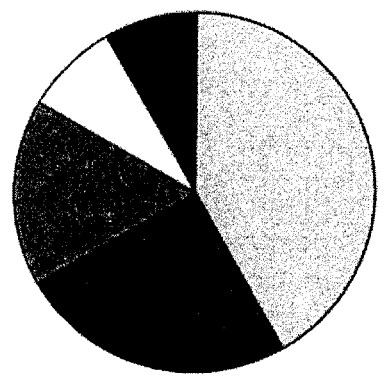

CTX induced a reduction of bacterial groups from the Firmicutes phylum distributed within four genera and groups (*Clostridium* cluster XIVa, *Roseburia*, unclassified Lachnospiraceae, *Coprococcus*, Table 2) in the mucosa of CTX-treated animals. CTX was also associated with a reduction in the proportion of Spirochaetes phylum (p=0.016), in particular the *Treponema* genus (0.025% in NaCl vs 0% in CTX group; p=0.016). At the level of species, some bacteria were either overrepresented (such as *Lactobacillus reuteri*) or underrepresented (such as *Clostridium* sp. clone 40 and several other butyrate-producers from the Lachnospiraceae family and from the *Clostridium* cluster XIVa) post-CTX (FIG. 2B). Segmented filamentous bacterium X77814 (SFB) did not reveal a consistent enrichment in CTX-treated mice compared with controls (7.95% SFB in CTX versus 0.83% in vehicle controls, p=0.08, Table 2). Wilcoxon test: *, p<0.05 in Co versus CTX in TB$^-$ groups, ‡, p<0.05 in Co versus CTX in TB$^+$ groups.

FIG. 7: Loss of CD103$^+$CD11b$^+$ and Th17 cells in the duodenal lamina propria and Th1 polarization of splenocytes correlating with small intestine bacterial species.

(A). Dendritic cell (DC) subsets in LP of the small intestine. Flow cytometry analyses and quantification of various DC subsets residing in small and large intestine LP at day 0, day 3 and day 7 post-CTX injection. The graph depicts means+SEM of the percentages of DC in 7 mice/ time point in two concatenated experiments. Large intestine DC subsets were not affected by CTX (not shown). Data were analyzed with the Mann Whitney t-test. (B-C). Modulations of Th17 cells seven days post-CTX. (B) Flow cytometry analyses of lymphocytes separated from the LP of duodenum and ileum, harvested from NaCl versus CTX-treated mice. The graphs depict the concatenated data from eight independent experiments, each dot representing one experiment. Statistical comparisons were based on the Wilcoxon test. (C). Left panel: a micrograph picture of immunofluorescence staining of ileum in NaCl versus CTX-treated mice. γδ TCR$^+$ cells were stained in green (ALEXA FLUOR 488) using an anti-γδ TCR Ab and CD3$^+$ T cells were stained in blue (ALEXA FLUOR 647) using anti-CD3 Ab. Right panel: the enumeration of positive cells was performed on 100 villi in three ilea by two independent researchers. (D). Th1 polarization of splenocytes at day 7 post-CTX injection. Splenocytes from CTX versus NaCl treated animals reared in GF or conventional SPF conditions (left panel) and treated or not with ATB or vancomycin (right panel) were cross-linked using anti-CD3±anti-CD28 Abs for 48 h. The levels of IFNγ were monitored in 48 hour-supernatants by ELISA. Three experiments containing 2-9 mice/group are presented, each dot representing one mouse. Data from (C) and (D) were analyzed with the t-test. (E). Idem as in FIG. 3C but correlations were analyzed between each bacterial group and IFNγ secretory profile as shown FIG. 6 (C) in naïve, B16F10 or MCA205 tumor bearers. (F). Representative dot plot flow cytometry analysis of splenic pTh17 cells as enumerated in FIG. 3C at day 7 post-CTX. *, $p<0.05$, **, $p<0.01$, ns, not significant.

Figure 8A:
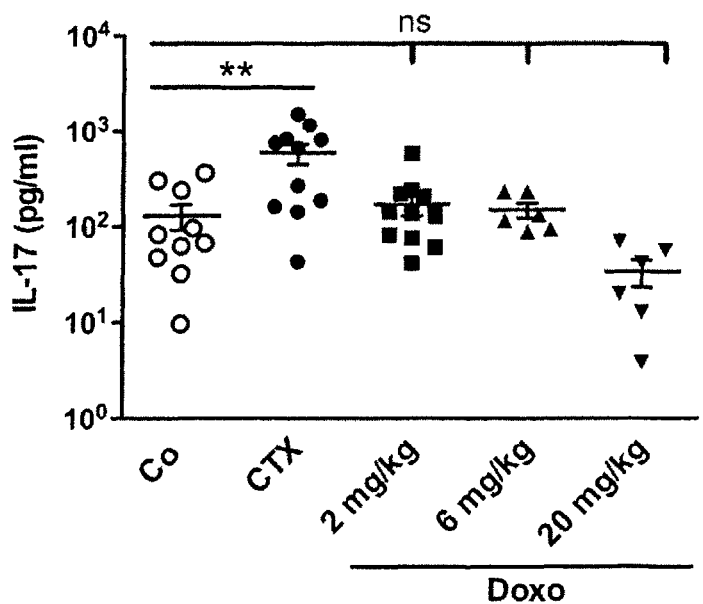
Figure 8B:
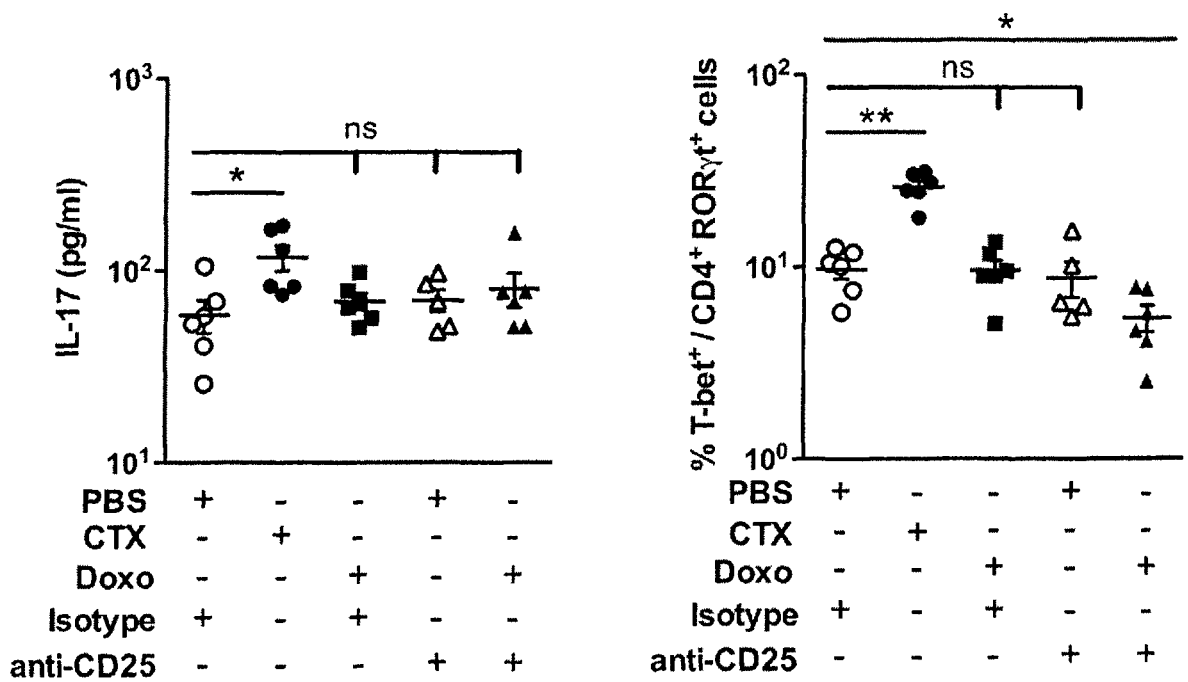
Figure 8C:
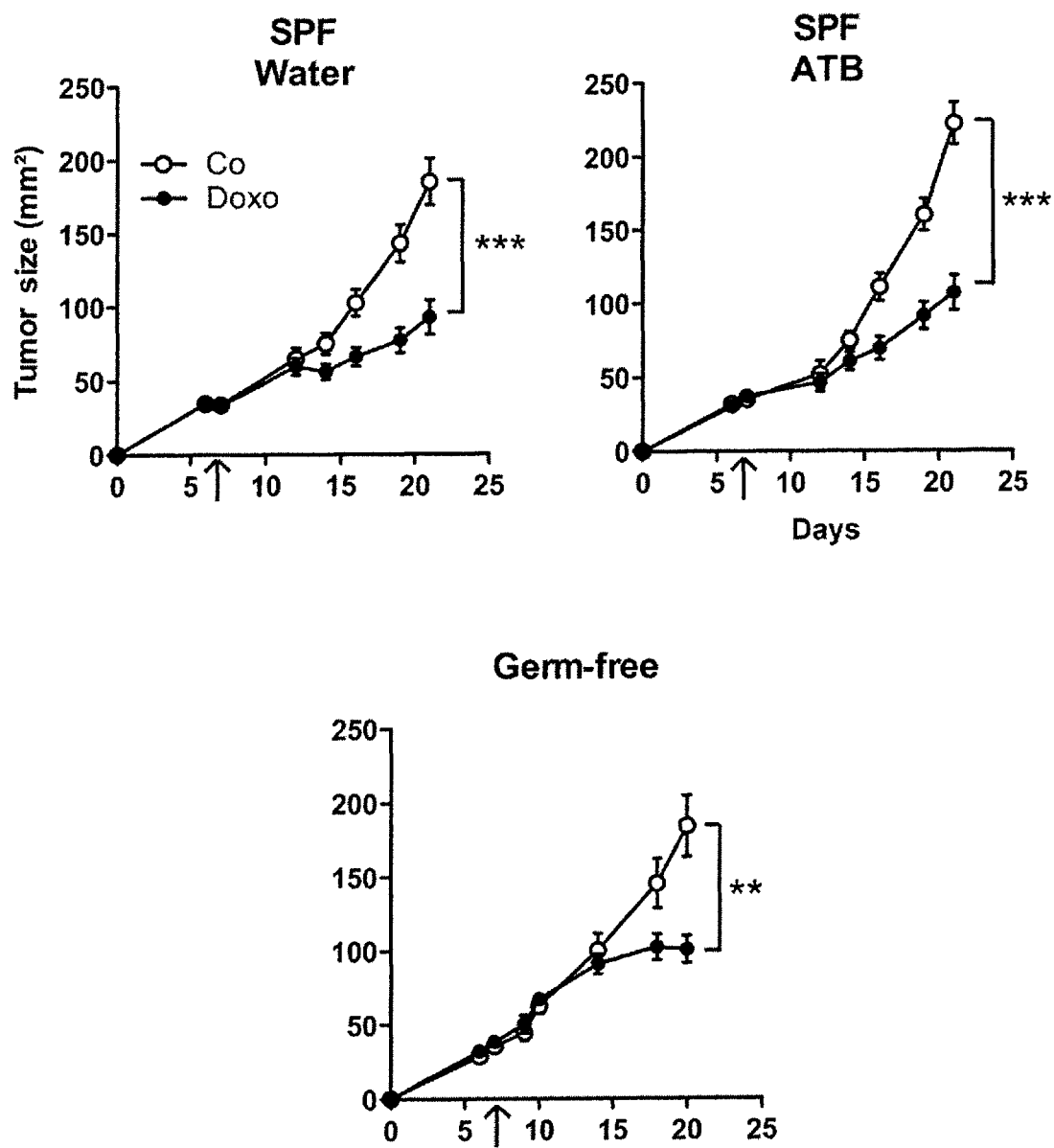

FIG. 8: Doxorubicin failed to induce pTh17 cells in the spleen and does not require gut commensals for reducing tumor growth.

(A-B). Failure of doxorubicin (Doxo) to induce splenic IL-17 producing CD4$^+$ T cells. Doxo was injected i.p. into mice at the indicated doses (A) or at a fixed dose of 50 μl at 2 mM (being 3 mg/kg for a mouse weighing 20 g) (B), and splenocytes were recovered 7 days later to evaluate the production of IL-17 in response to 48 hours anti-CD3/anti-CD28 cross-linking (A, B) or the frequency of cells with a CD4$^+$ T-bet$^+$RORγt$^+$ phenotype was determined by flow cytometry (B). Cyclophosphamide (CTX) used at a dose of 100 mg/kg was used as a positive control. Optionally, regulatory T cells were depleted by injections (250 μg, 1 and 3 days before Doxo administration) of anti-CD25 Ab and an irrelevant isotype-matched control Ab was used as control. (C). Antitumor effects of doxorubicin against established MCA205 in specific pathogen-free (SPF), antibiotic (ATB)-treated and germ-free mice. Kinetics of tumor growth (mean size±SEM) are depicted in 2 to 3 pooled experiments including 4-6 animals/group. Data were analyzed with the t-test, linear model or generalized linear model. *, $p<0.05$, , $p<0.01$, *, $p<0.001$, ns, not significant.

Figure 9:
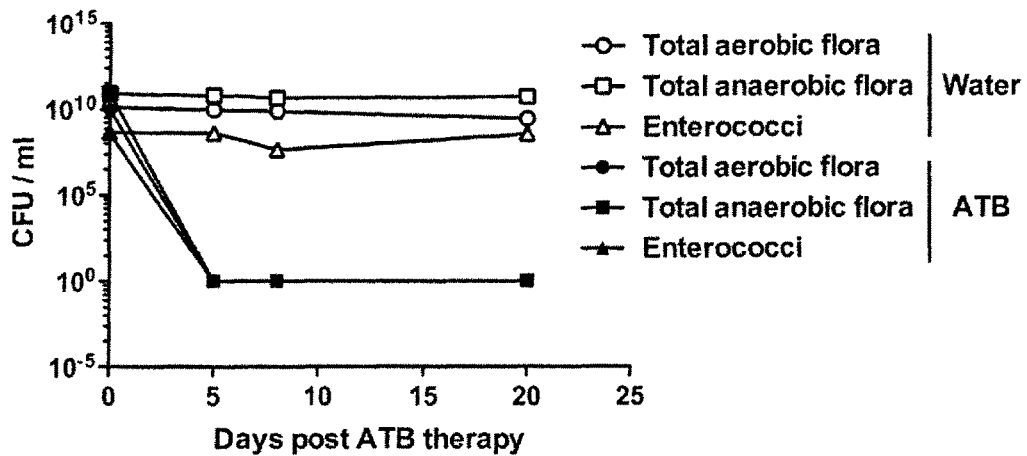

FIG. 9: Efficacy of broad spectrum ATB in bacterial depletion from the feces of naïve or tumor-bearing mice.

Feces were freshly harvested from mice that were left untreated or were treated with broad spectrum ATB at various time points and plated onto blood agar plates for aerobic and anaerobic conditions, as well as onto DCO agar plates (BioMérieux) for the specific growth of enterococci. After 48 h of culture, isolated colonies were enumerated. All the mice of each distinct experiment have been monitored and scored in this manner. One representative monitoring is shown.

Figure 10:
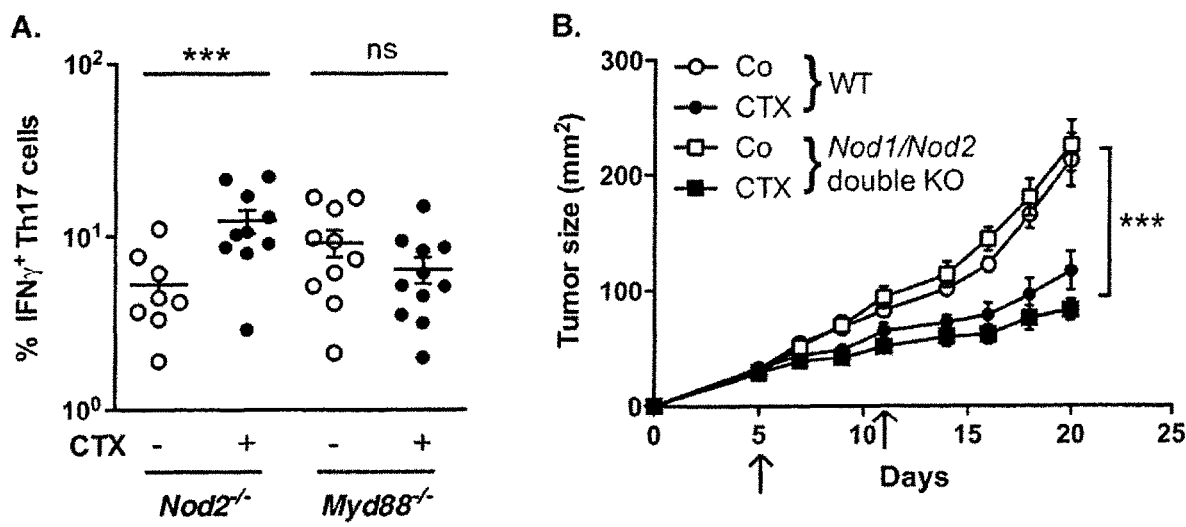

FIG. 10: CTX-induced pTh17 differentiation depends on Myd88 but not Nod1/2.

(A). Flow cytometry analyses of lymphocytes harvested from NaCl versus CTX-treated WT (as in FIG. 3C) or Nod2$^{-/-}$ versus Myd88$^{-/-}$ mice restimulated 4 hours with PMA/ionomycin (using intra- and extra-cellular stainings with anti-CD3, CD8, IFNγ and IL-17 Abs). The graph depicts the mean percentages of IFNγ$^+$ positive cells among IL-17$^+$CD4$^+$ T cells from two independent experiments, each dot representing one mouse. (B). Nod1 and Nod2 are dispensable for tumor growth reduction induced by CTX MCA205 tumors were established in WT or Nod1$^{-/-}$ Nod2$^{-/-}$ mice before administration, at day 5 and 12, of CTX. The tumor growth kinetics (means±SEM) were monitored in 5 animals/group. Two independent experiments yielded similar results. Data were analyzed with the t-test, linear model or generalized linear model. ***, $p<0.001$, ns, not significant FIG. 11: Immunization against commensal bacteria post-CTX.

(A-C). Recovery of CBir Tg T cells in congenic mice after CTX One million naïve B6.CD45.1$^+$ CBir1 TCR Tg CD4$^+$ T cells were adoptively transferred i.v. in naïve CD45.2 WT recipient congenic mice that were treated, one day later, with NaCl or CTX and sacrificed 7 days later for FACS analysis of splenocytes and ex vivo restimulation with CBir1 specific peptides. Gating of CD45.1 cells allowed to analyze the percentages of recovery or proliferation of CBir1 Tg T cells (A, means±SEM for 5 animals) and to analyze IL-17 and IFNγ production using intracellular staining after 6 h PMA/ionomycin activation. A representative dot plot is shown for one animal in B. Splenocytes were restimulated for 24 h with the CBir1 specific peptide or a control irrelevant peptide. Commercial ELISA monitored the concentrations of IFNγ in the supernatants (C). Three experiments were performed encompassing 4-5 animals/group. Mann Whitney t-test: **, $p<0.01$.

Figure 12:
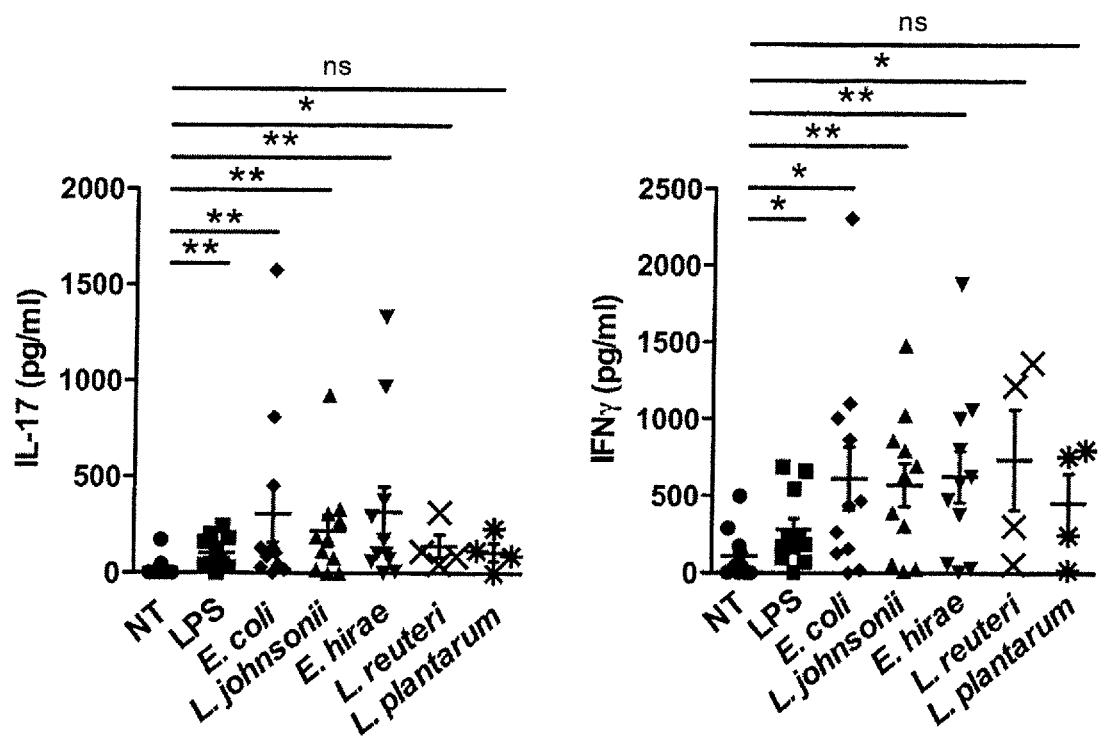

FIG. 12: Translocated bacteria processed and presented by dendritic cells lead to the polarization of naïve CD4$^+$ T cells in vitro. Ex vivo differentiation of Th17/Th1 cells with translocated bacteria. Cross-talk between BMDCs loaded with various bacteria and naïve CD4$^+$T for 4 days. Monitoring of IL-17 (left) or IFNγ (right) cytokine concentrations by commercial ELISA. Each dot represents one in vitro experiment performed in triplicate wells. Eleven experiments were performed and are depicted. t-test: *, $p<0.5$, **, $p<0.01$, ns, non significant.

Figure 13:
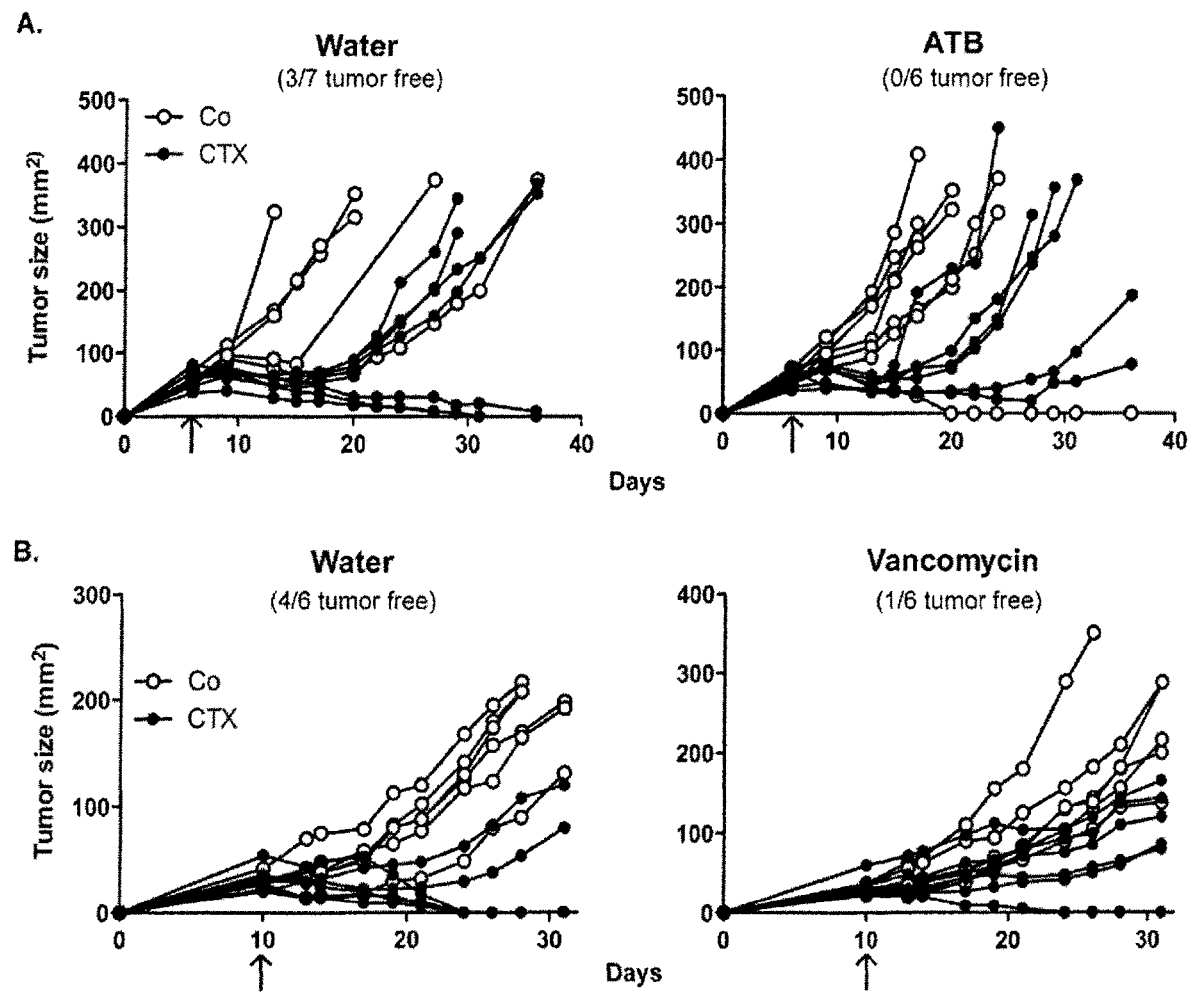

FIG. 13: Gut microbiota affects chemotherapy efficacy.

(A). Bacterial depletion by ATB reduced chemosensitivity of established mastocytomas. Day 6 P815 bearing DBA2 mice pretreated or not for 3 weeks with broad spectrum ATB were inoculated i.p. with 100 mg/kg of CTX and tumor growth was monitored until sacrifice. Growth kinetics are shown for each individual mouse in water versus ATB-treated mice in a representative experiment out of three. (B). Vancomycin reduced the efficacy of CTX against MCA205 sarcomas. Day 10 MCA205-bearing C57BL/6 mice pretreated or not for 3 weeks with vancomycin were inoculated i.p. with 100 mg/kg of CTX and tumor surfaces as well as tumor rejection rates were monitored over one month. Growth kinetics are shown for each individual mouse in water versus vancomycin-treated mice in a representative experiment out of two while the percentages of tumor free mice are indicated in parentheses.

Figure 14:
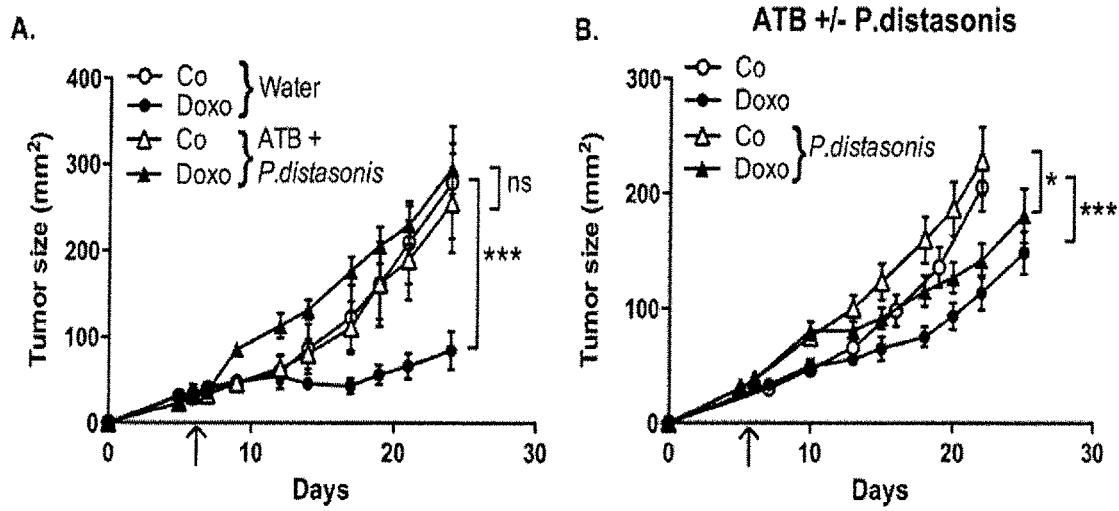

FIG. 14: *Parabacteroides distasonis* and chemoresistance.

(A). Monoassociation with *Parabacteroides distasonis* induced chemoresistance of established sarcomas. Conventionally reared mice were treated for 2 weeks with broad spectrum antibiotics (ATB), inoculated with MCA205 for 7 days and then treated with doxorubicin. In this particular experiment, feces were contaminated by one single bacterial species identified as *P. distasonis* by means of VITEK® automated system and MALDI-TOF. Tumor growth kinetics (means±SEM) revealed that ATB combined with *P. distasonis* contamination induced a cancer chemoresistance status in vivo (n=4-5 mice/group) (B). Conventionally reared mice were treated for 3-4 weeks with ATB, implanted 4 days with MCA205 and then orally inoculated with *P. distasonis* that monocolonized feces. At day 6 post-tumor inoculation, mice were treated with doxorubicin. The tumor growth kinetics between *P. distasonis* reconstituted or unreconstituted ATB treated-mice post-doxorubicin (means±SEM) were monitored in 8-12 mice/group. Data were analyzed with the linear model or generalized linear model. *p<0.05, ***p<0.001.

Figure 15:
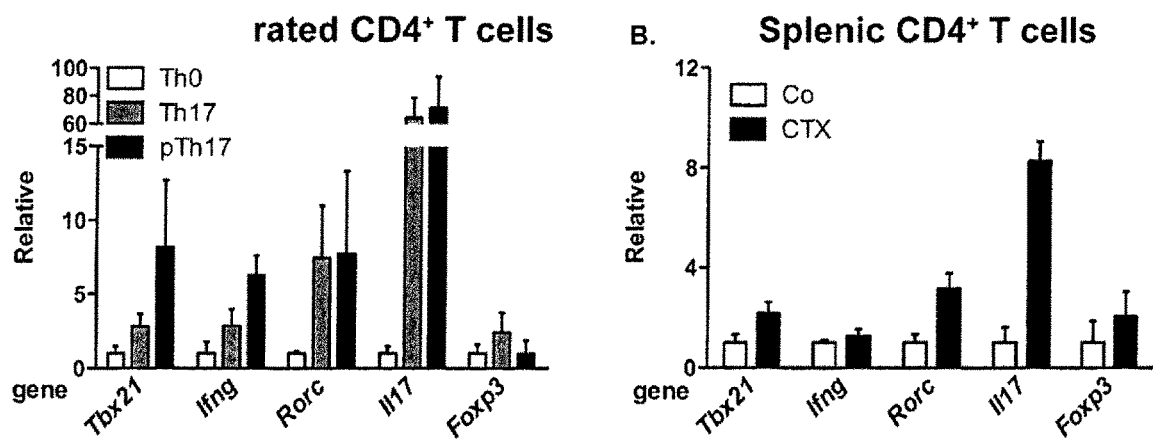

FIG. 15: Transcriptional profiling of ex vivo generated Th17 and pTh17 compared with CTX-induced spleen CD4$^+$ T cells.

Naive T cells were stimulated with plate-bound antibodies against anti-CD3 and anti-CD28 Abs in the absence (Th0) or presence of either recombinant mouse IL-1β (10 ng/ml)+IL-6 (10 ng/ml)+IL-23 (20 ng/ml) (as for "pTh17" cells) or with rTGF-β (2.5 ng/ml)+IL-6 (as for "Th17" cells). The transcriptional profile of in vitro generated pTh17, Th17 cells (A) as well as ex vivo harvested splenic derived CD4$^+$ T cells post-NaCl or CTX (B) is shown. Quantitative RT-PCR were performed with specific probes detecting transcription factors and cytokines defining Th1 versus Th17 polarization.

Figure 16:
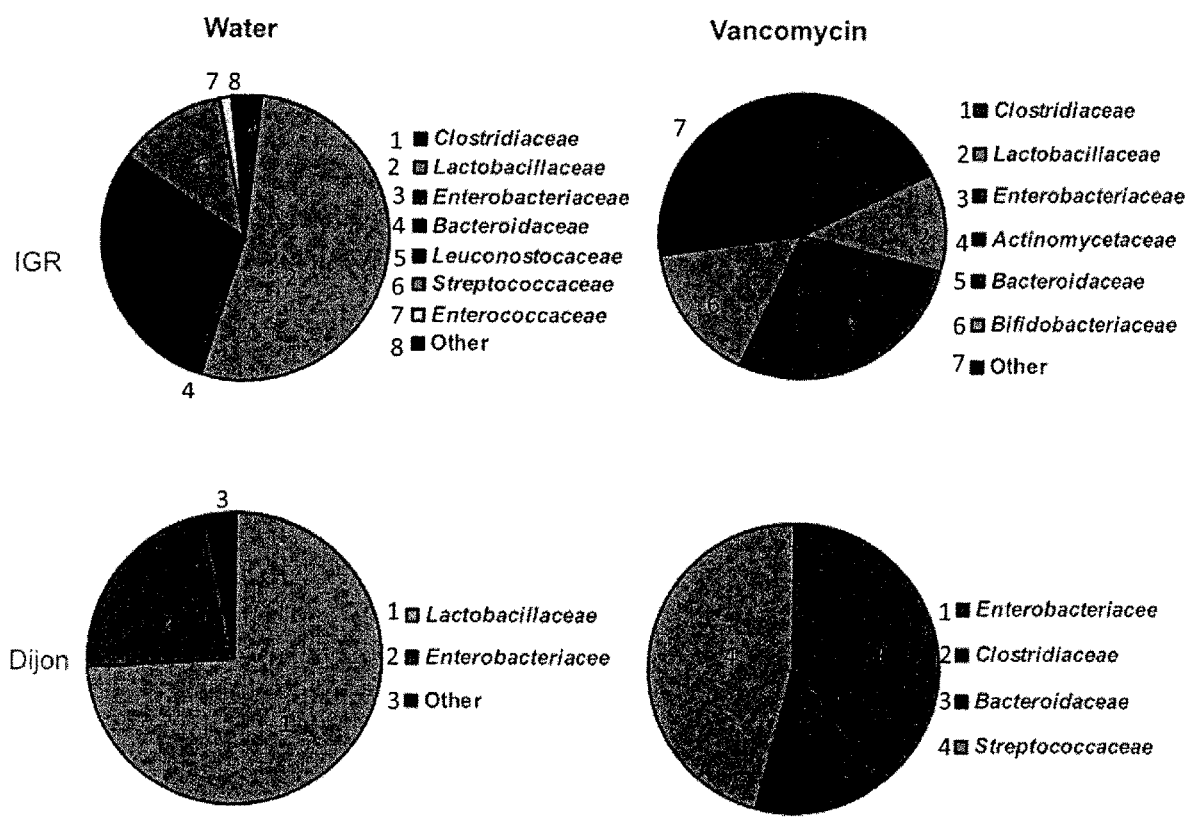

FIG. 16: Vancomycin-resistant microbial microbiota.

Fecal commensals from tumor bearers that were left untreated or were treated with vancomycin were plated, enumerated and identified as specified in Materials and Methods to analyze the number of resistant colonies. The results of two independent experiments run in two different animal facilities (CGFL, Dijon versus IGR, Villejuif) are depicted.

Figure 17:
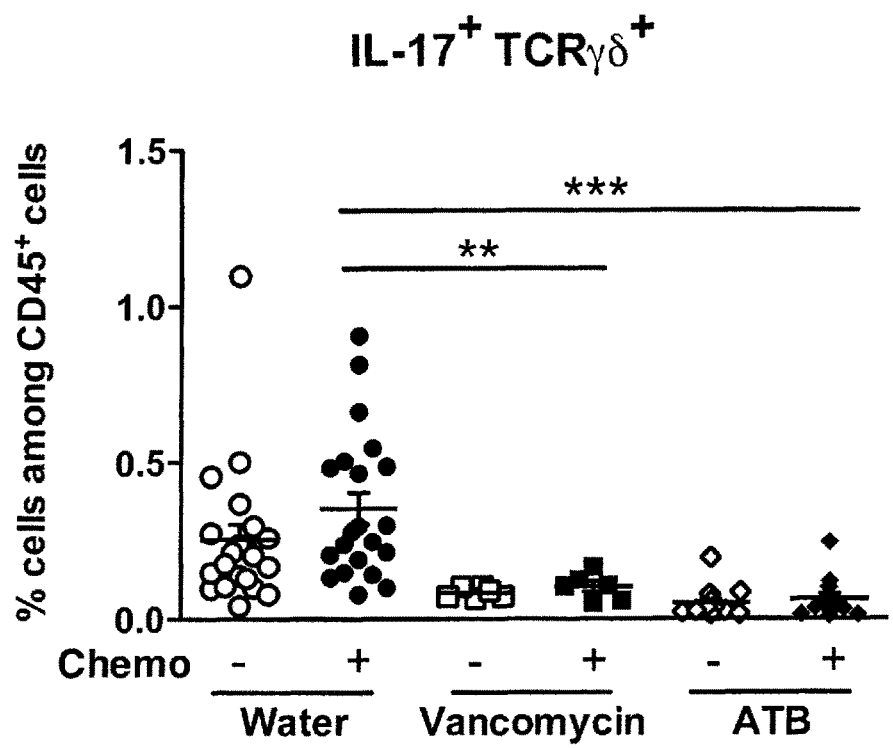

FIG. 17. Antibiotics affect the chemotherapy-induced accumulation of γδT17 tumor infiltrating lymphocytes. MCA205 sarcomas were treated with chemotherapy at day 10 and harvested at day 18 for flow cytometry phenotyping of tumor-infiltrating γγT cells producing IL-17. The percentages of TCRγδ$^+$IL-17$^+$ among CD45$^+$ live leukocytes are depicted in each group treated or not with vancomycin or broad spectrum ATB. Each group contained 6-21 mice. Student t' test: , p<0.01, *, p<0.001.

Figure 18:
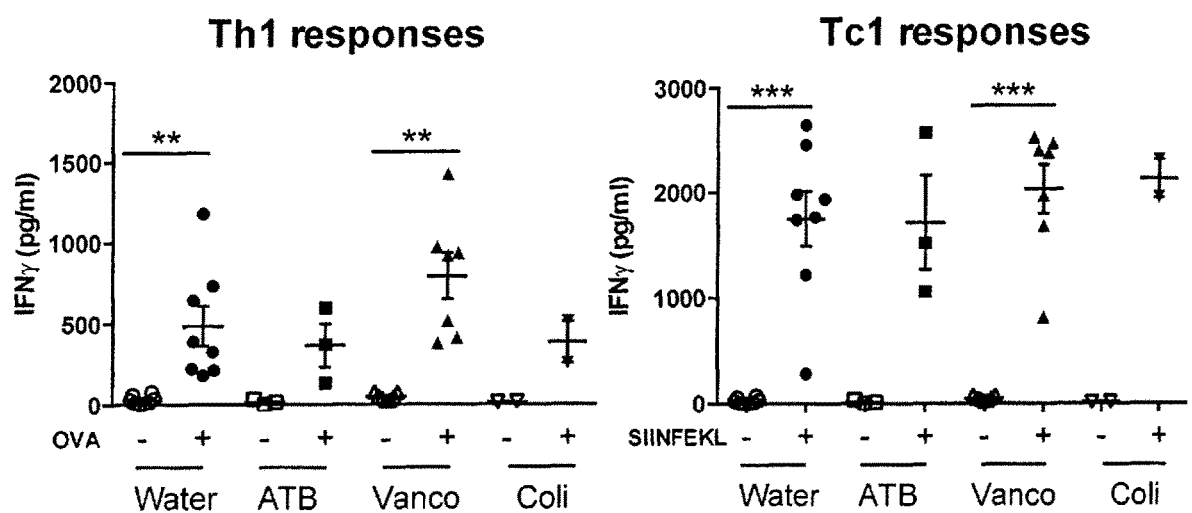

FIG. 18: Primary cellular Th1 and Tc1 immune responses against chicken OVA are not affected by antibiotics regimen in wild type naïve mice. C571Bl/6 mice were pre-treated for 8-10 days with various antibiotic regimens, including large spectrum antibiotics (ATB), colistin (*Coli*) or vancomycin (Vanco), monitored by culturing feces at various time points and then, immunized in the footpad with 1 mg of OVA admixed with 50 µg of Poly (LC) three days after i.p. CTX administration. At day 5 post-vaccine, popliteal and inguinal draining lymph nodes were harvested and restimulated with OVA protein (left panel) or SIINFEKL (SEQ ID No: 33) peptides (right panel) at 1 mg and 10 µg/ml respectively. IFNγ release was monitored at 72 hours in the supernatants by ELISA. Each dot represents one mouse, and the means of triplicate wells of in vitro restimulation. The statistical analyses have been performed in a paired t test comparing with versus without antigen restimulation to capture Ag specific effector/memory responses. , p<0.01, *, p<0.001, ns: not significant.

Figure 19:
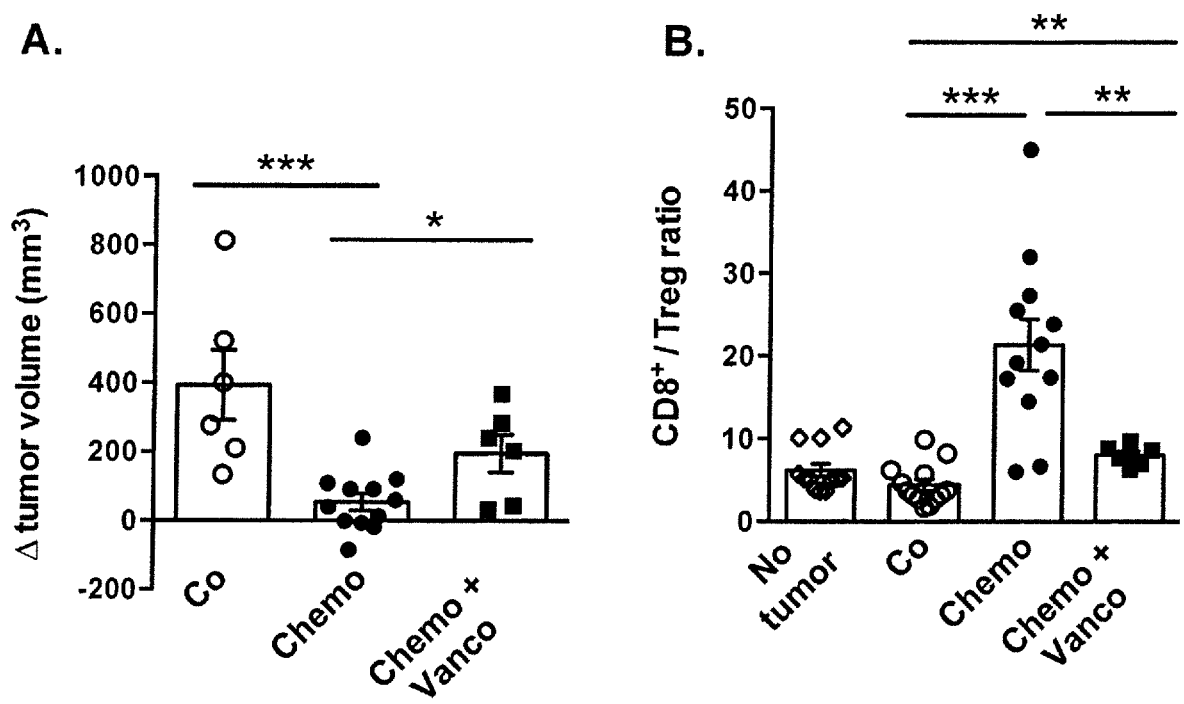
Figure 20A:
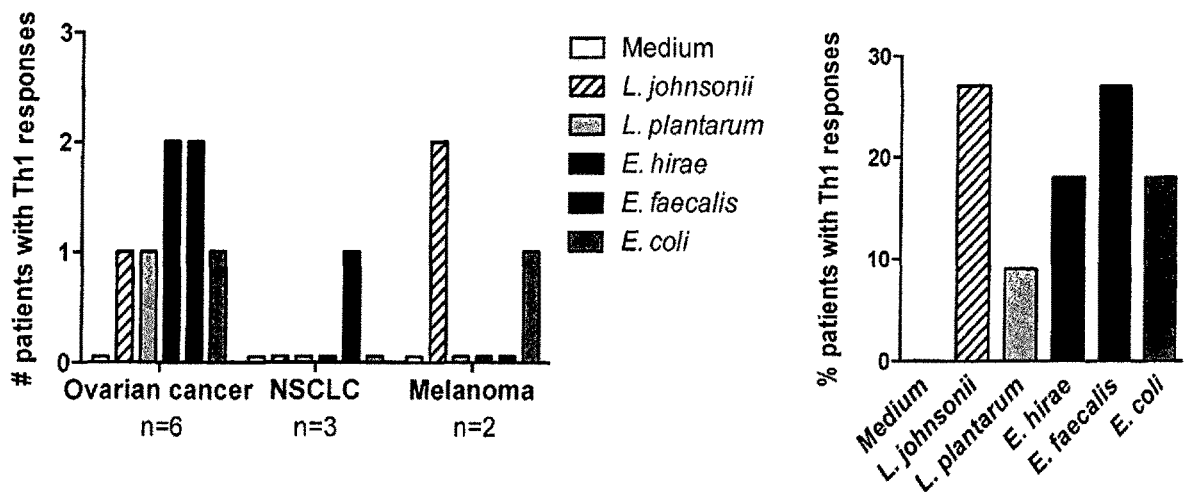
Figure 20B:
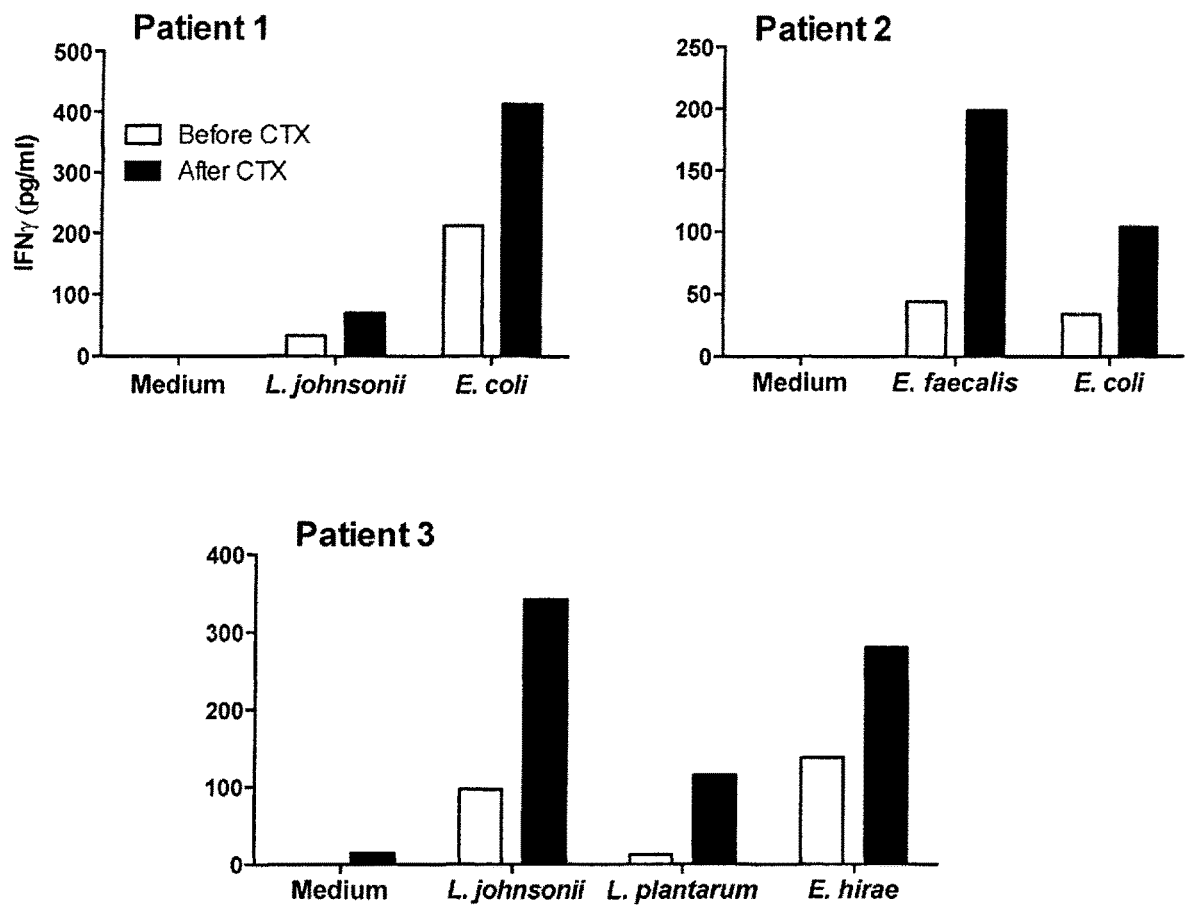
Figure 20C:
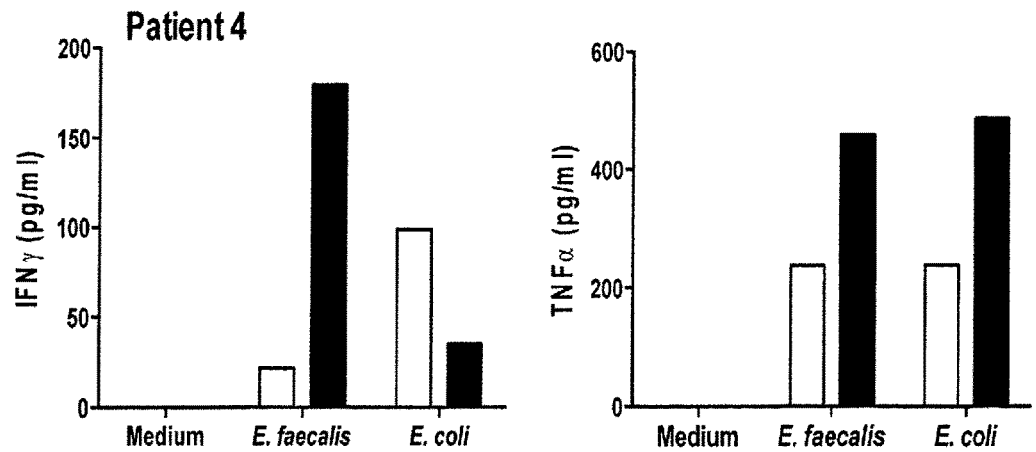
Figure 20D:
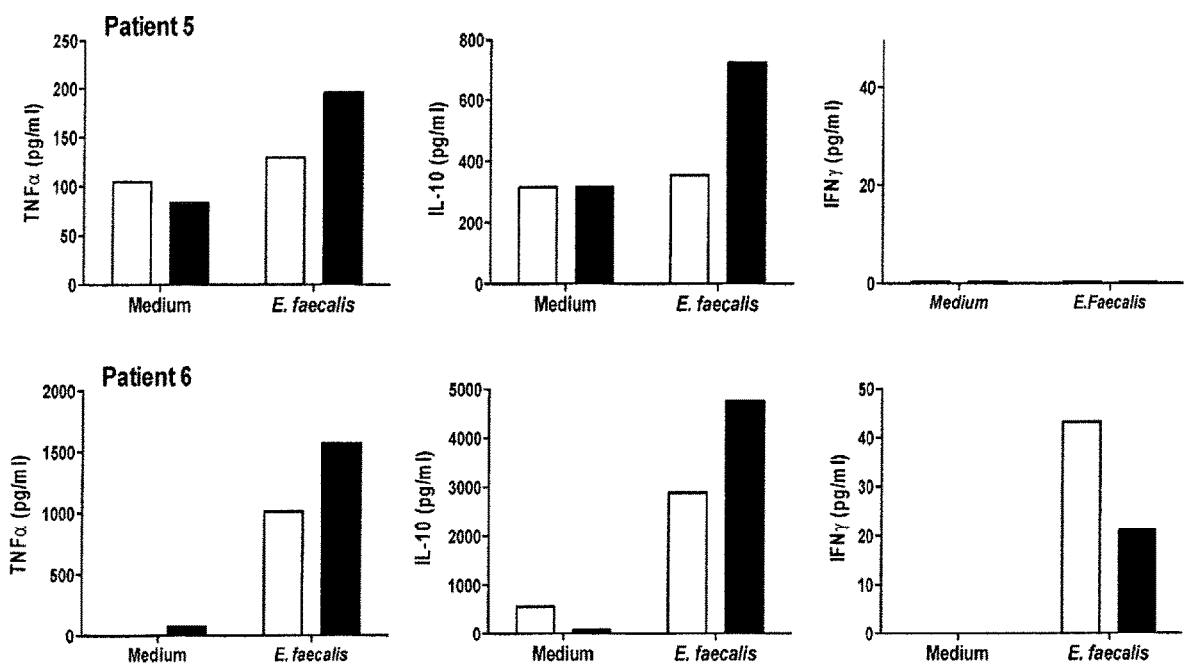

FIG. 19: Treatment of lung adenocarcinoma-bearing KP mice using chemotherapy. Eight week-old KP (KrasLSL-G12D/WT; p53$^{Flox/Flox}$) mice received an adenovirus expressing Cre recombinase (Ad-cre) by intranasal instillation to initiate lung adenocarcinoma (d0). Mice were either left untreated («Co») or received chemotherapy (d84, d91 and d98) in absence («Chemo») or presence of 0.25 mg/ml vancomycin («Chemo+Vanco») (mixed into drinking water starting on d77 post Ad-cre and until the end of the experiment; antibiotic-containing water was replaced biweekly). A. Tumor volumes were quantified on d73 and 100 (equivalent of 'pre' and 'post' chemotherapy) in anesthetized mice by noninvasive imaging as described before (Cortez-Retamozo et al., Immunity, 2012). Data show absolute changes in total lung tumor volumes (mean±SEM) between the two time points. Of note, antibiotics had no impact on the natural progression of this disease (not shown). B. The CD8/Treg ratio was determined by flow cytometry measurements on dissociated lung tissue samples derived from the respective groups. A group of tumor free mice («No tumor») was also investigated. n>6 mice for each group; *, p<0.05, **, p<0.01 (two-tailed unpaired t test).

FIG. 20: CTX-induced Th1 and Th10 immune responses directed against commensal bacteria in cancer patients.

Ex vivo restimulation assays using patients' autologous monocytes loaded with defined bacteria for 3 hours, neutralized with antibiotics, then cultured in GM-CSF+IL-4 (to differentiate into DC) and incubated for 3 days with CD4$^+$CD45RO$^+$ T cells (at a 1:2 ratio) purified from autologous blood at various time points (Day 0: before CTX, Day 12-46: after CTX, NSCLC: non small cell lung cancer). A. Cytokine release (IFNγ, TNF, IL-10) was monitored using ELISA. Numbers (A, left panel) and percentages (A, right panel) of patients exhibiting at least a 2 fold increase of IFNγ secretion between the pre- and post-CTX time points. B. Exemplification of 3 cases with a developing Th1 immune response; patient 3 developing a strong Th1 immunity elicited against *L. johnsonii+E. hirae*. C. One case with a strong Th1 immunity against *E. faecalis*. D. Two cases with a contrasting Th1/TH10 specific responses. B-D show the cytokine levels in the 40 h supernatants of 250.000 memory CD4$^+$ T cells for each individual patient pre- and post-CTX administration.

Figure 21:
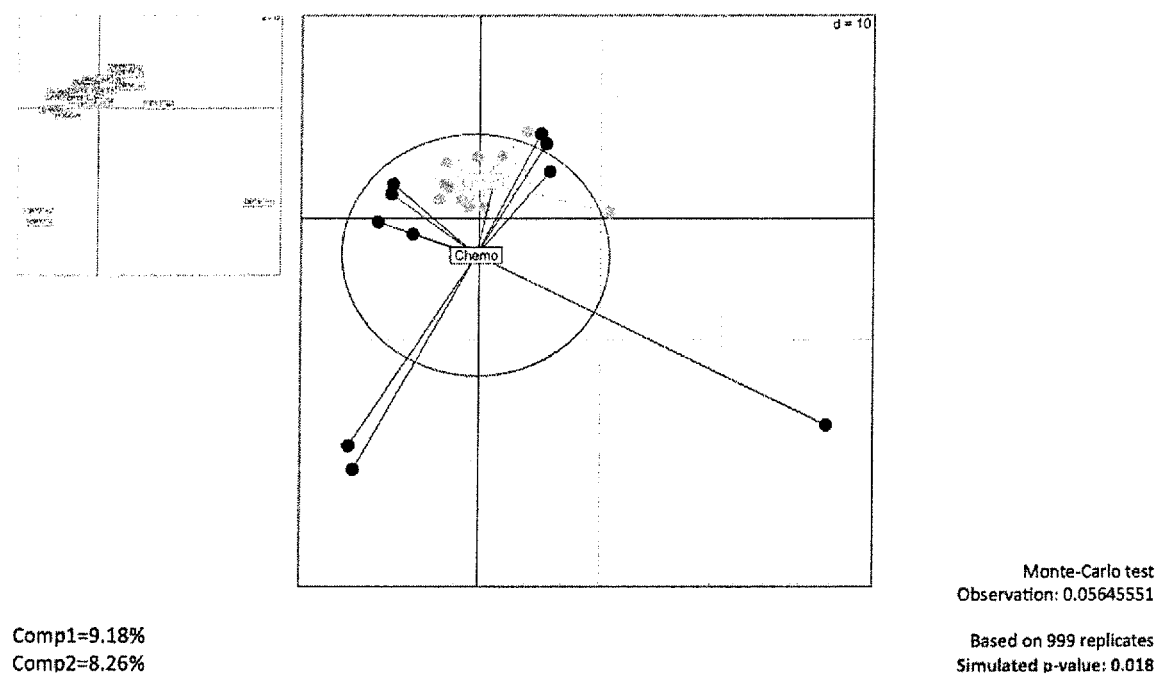

FIG. 21: Principal component analysis on the isolate levels of all patients' ileum after 16SrRNA pyrosequencing, comparing controls (no chemotherapy) versus post-neoadjuvant chemotherapy.

Figure 22:
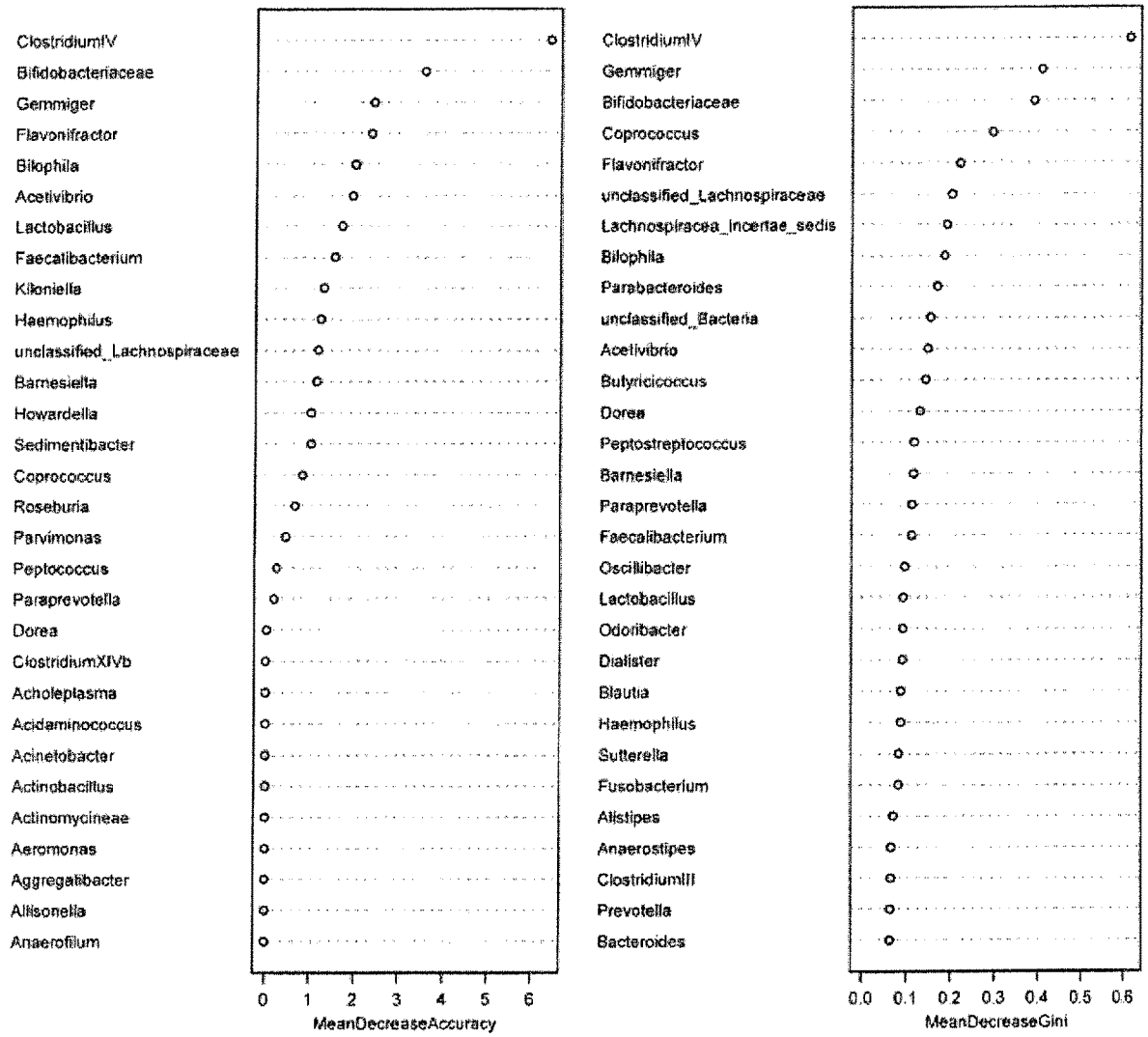

FIG. 22: Random forest analysis: Main discriminative genera between patients receiving or not chemotherapy and bearing a colon cancer.

Analysis from 6 patients in neoadjuvant oxaliplatine-based chemotherapy and 7 patients prior to therapy.

Figure 23:
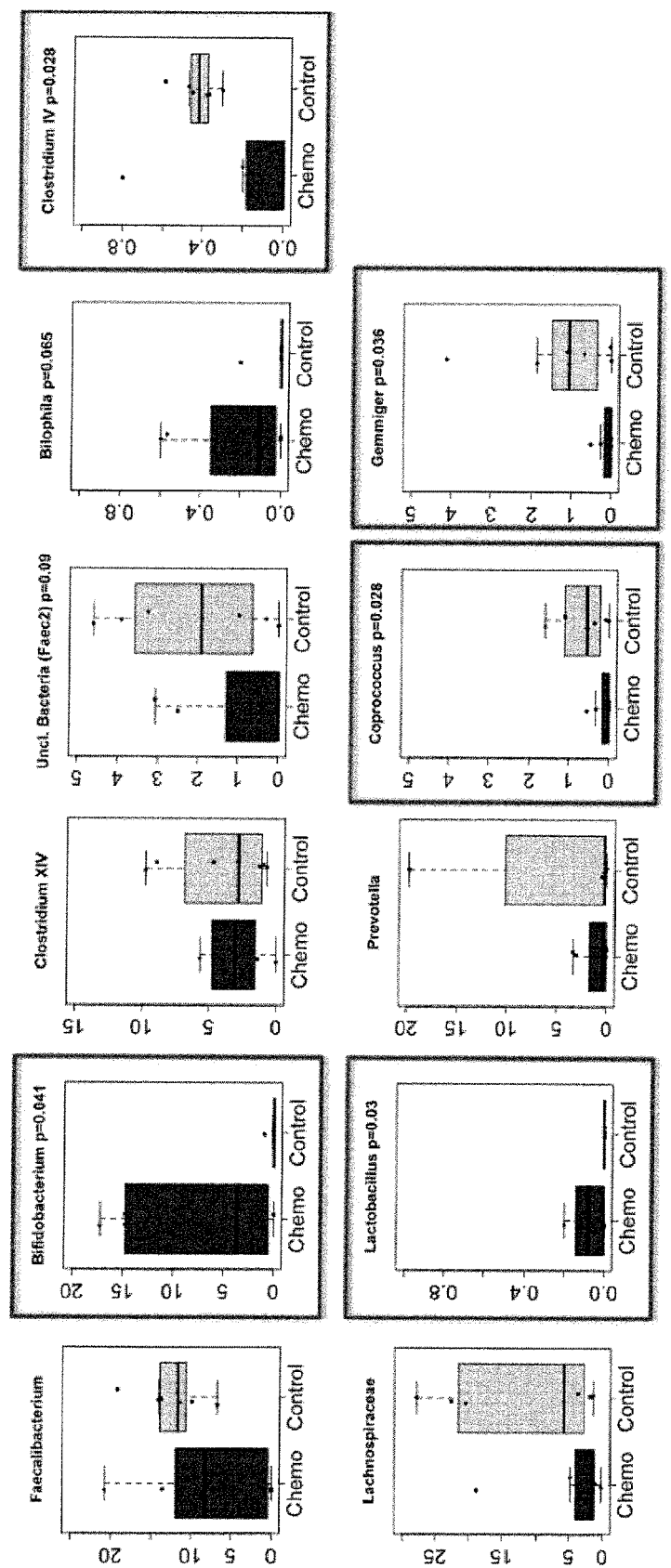

FIG. 23: Main genera that are significantly different between controls (no chemotherapy) versus post-neoadjuvant chemotherapy.

Figure 24:
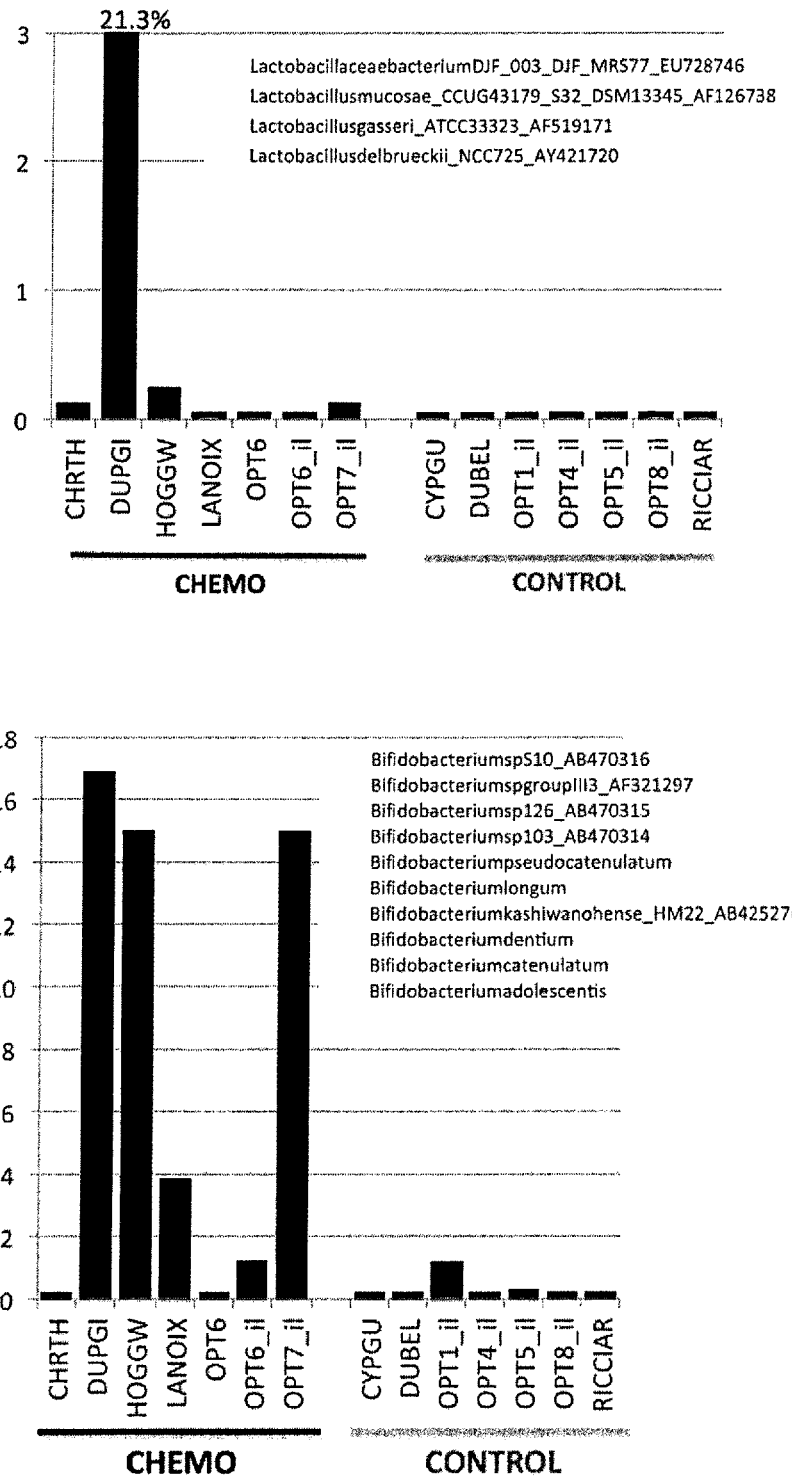

FIG. 24: Distribution of lactobacilli, *Bifidobacterium* and *Clostridium* group IV. In the ileum among colon cancer patients treated or not with chemotherapy.

Figure 25:
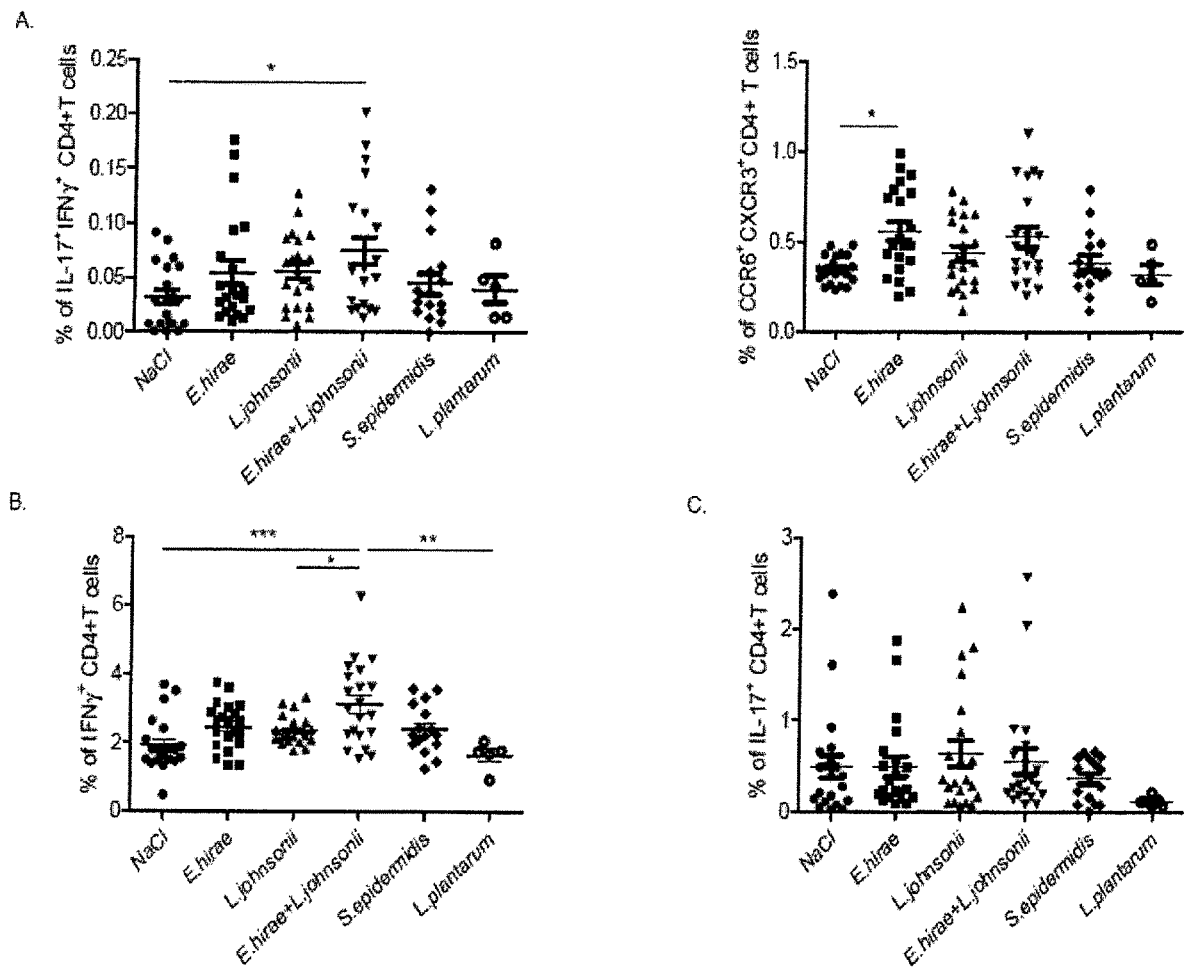

FIG. 25: TH1 and pTH17 immune responses following monoassociation with *E. hirae*. C57BL/6 mice were treated with vancomycine, streptomycine, ampicilline and colistine (broad spectrum ATB regimen) for 14 days, followed by one ip injection of 100 mg/kg of CTX on day 15 and oral feeding with $10^9$ bacteria (as illustrated on the graph) on day 16 prior to flow cytometric analyses of the splenocytes at day 22. A-C. Flow cytometric analyses of pTH17 cells. CD4+ T cells expressing or co-expressing IFNγ and IL-17 (left panel) or CXCR3 and CCR6 (right panel) in the gate of live splenocytes. Concatenated data from 3 individual experiments including 5 mice/group. Anova statistical analyses: *p<0.05, p<0.01, *p<0.001.

Figure 26:
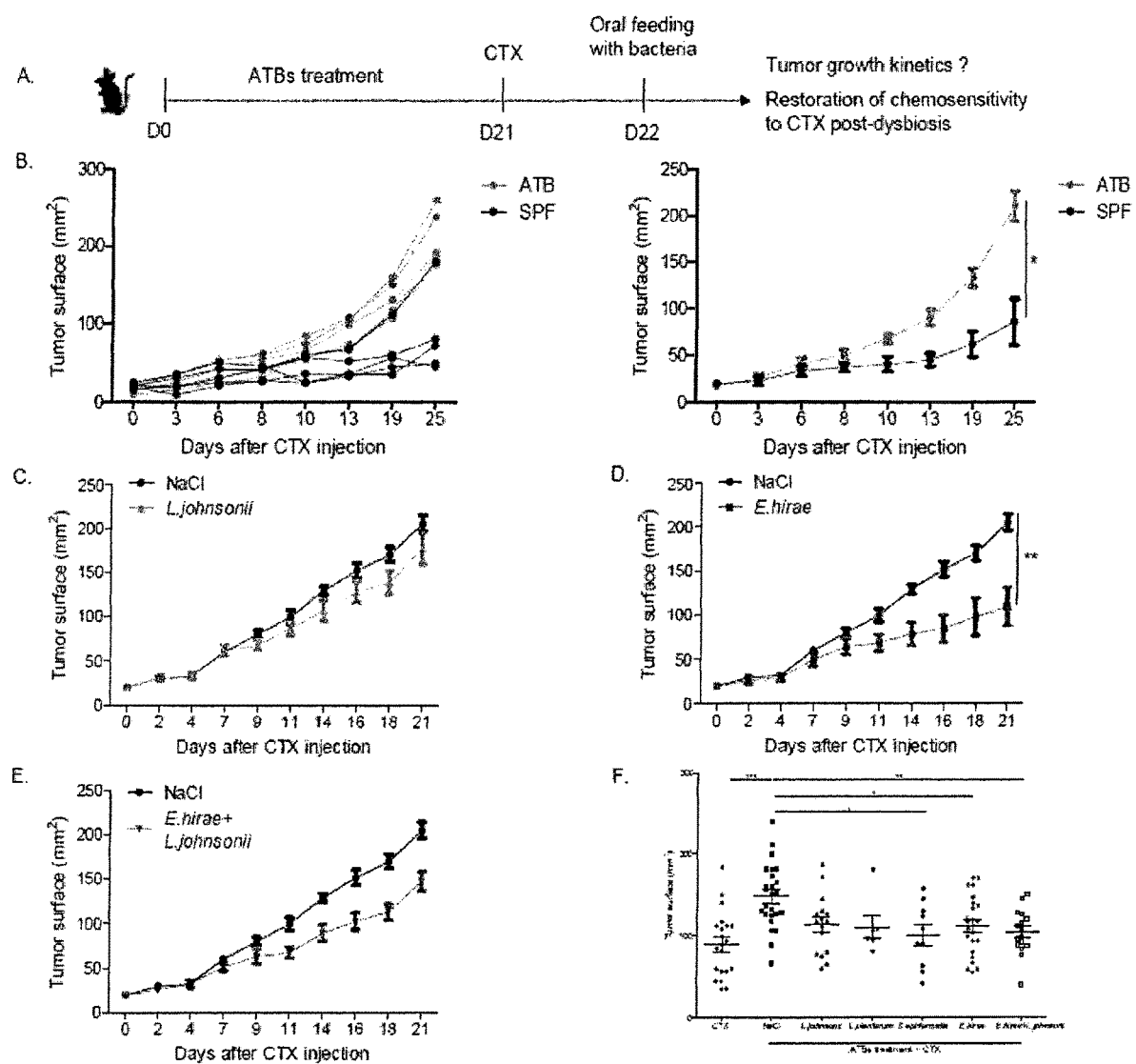

FIG. 26: Anticancer probiotics active against MCA205 treated with CTX. C57BL/6 mice were treated with vancomycine, streptomycine, ampicilline and colistine (broad spectrum ATB regimen) for 14 days, then inoculated sc. with MCA205 sarcoma, then treated with one ip. injection of 100 mg/kg of CTX on day 21 and oral feeding with $10^9$ bacteria (as illustrated on the graph) on day 22. Tumor growth kinetics were monitored biweekly for 1 month. A. Experimental setting. B. Tumor growth for the positive (CTX without ATB) and negative control (CTX with ATB) groups. C-F. Tumor growth kinetics in the presence of oral gavage with *E. hirae*, or *L. johnsonii* or both of them (cocktail). F. Concatenated data from 3 experiments including 5 mice/group. Anova statistical analyses: *p<0.05, p<0.01, *p<0.001.

Figure 27:
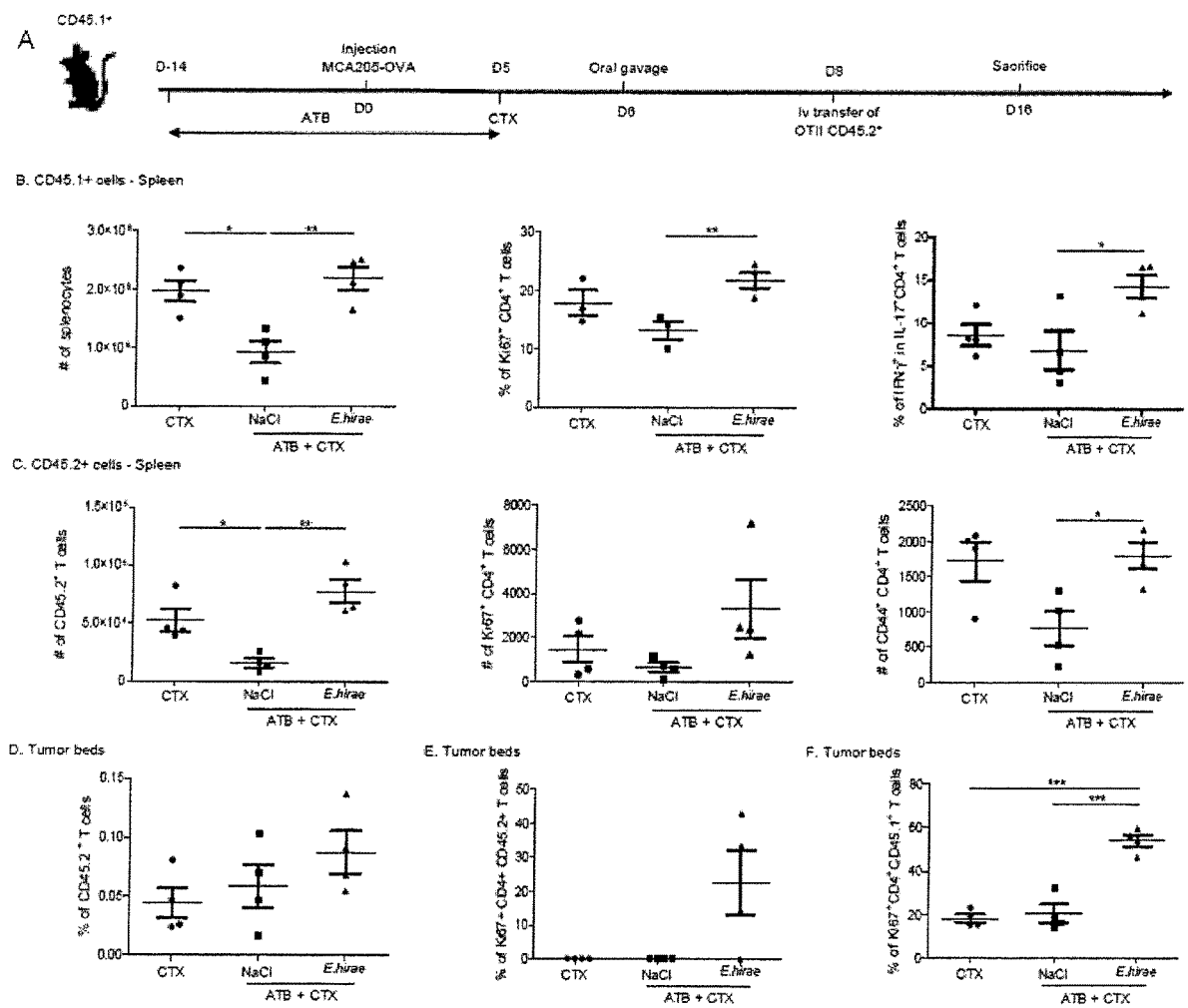

FIG. 27: *E. hirae* induces OVA-specific antitumor-immune responses. CD45.1+ C57BL/6 mice were treated with vancomycine, streptomycine, ampicilline and colistine (broad spectrum ATB regimen) for 14 days, then inoculated sc with MCA205-OVA sarcoma, then treated with one ip injection of 100 mg/kg of CTX on day 21 and oral feeding with $10^9$ *E. hirae* (as illustrated on the graph A) on day 22. On day 24, $10^6$ CD45.2+ OTII transgenic T cells were transferred iv and mice were sacrificed 8 days later for flow cytometric analyses of recipient (CD45.1, B) or donor (CD45.2) CD4+ T lymphocytes. B. Splenocytes counts (left panel), determination of percentages of Ki67+ CD4+ T cells (middle panel), and pTH17 in the host post-CTX with or without ATB. C. Recovery of donor T cells examined through CD45.2+, Ki67+ or CD44+ expression in the spleen. D. Idem as in C but in the tumor bed by enumerating absolute numbers. A representative experiment is shown with Student t'test for statistical analyses. *p<0.05.

Figure 28:
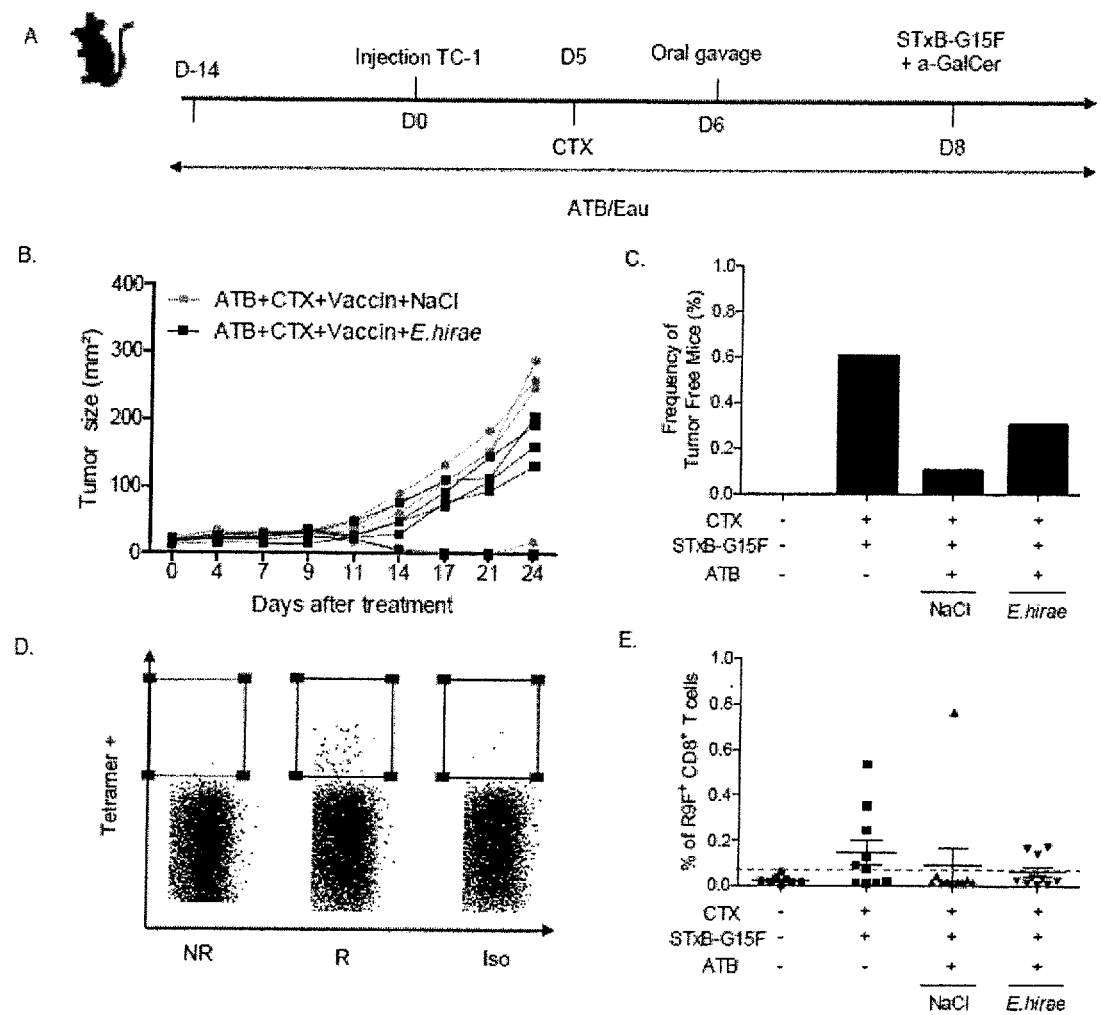

FIG. 28: *E. hirae* induces E7-specific antitumor-immune responses. A. Experimental setting. Subcutaneous TC1 inoculation in mice pretreated with broad spectrum ATB and therapy at day 7 post-tumor implantation using a combination of SBxT-E7 and CTX (+/− monoassociation with *E. hirae*). B-C. Representative tumor growth kinetics and percentages of complete tumor eradication in two experiments. D. Monitoring of $D^b_{-E739-47}$ tetramer binding CD8+T cells in the spleens. Results from two experiments are presented. Anova test for statistical analyses. *p<0.05.

Figure 29:
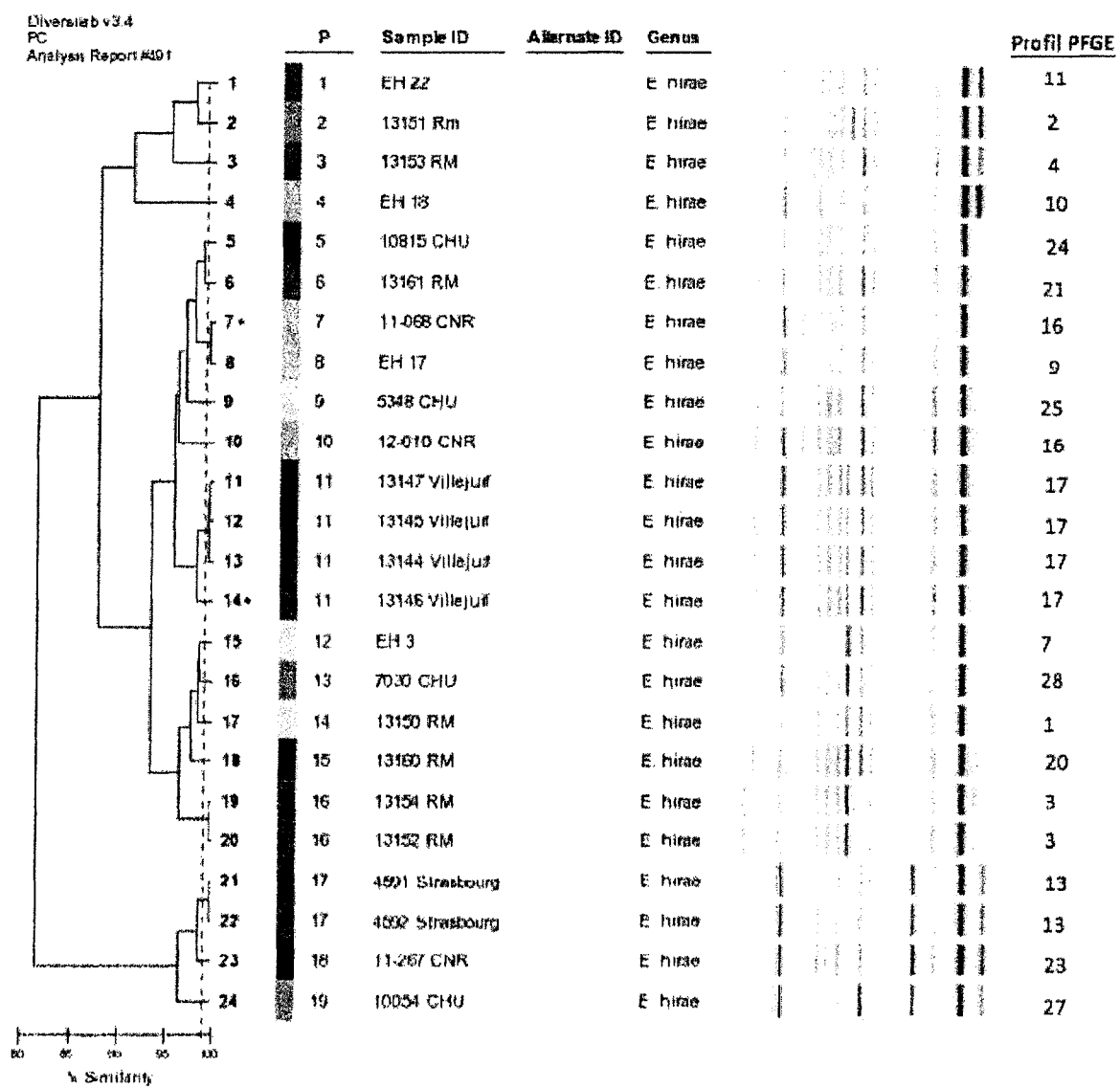

FIG. 29: Pulsed field gel electrophoresis of a series of *E. hirae* isolates from different public libraries. Non supervised hierarchical clustering of the sequence similarities among these clones. Clone 13144-13147 have been isolated in the Gustave Roussy animal facility from mice splenocytes after different kind of therapies (CTLA4 blockade, CTX). The one isolate that has been used henceforth or above is noted "13144 Villejuif" in this Figure, and corresponds to the *Enterococcus hirae* strain deposited on Nov. 7, 2013 at the Collection Nationale de Cultures de Microorganismes (CNCM), under the number I-4815.

Figure 30:
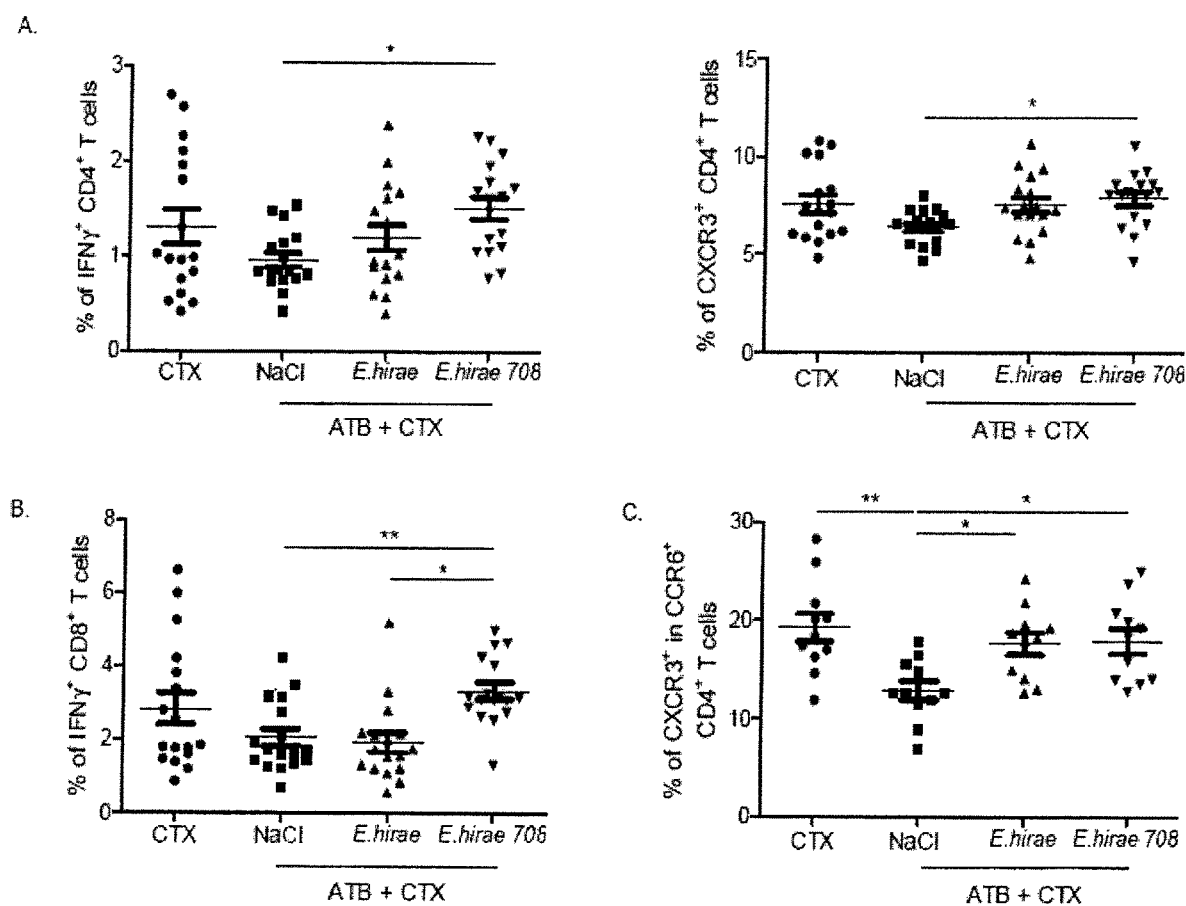

FIG. 30: Differential immunogenicity of various *E. hirae* isolates in vivo. C57BL/6 mice were treated with vancomycine, streptomycine, ampicilline and colistine (broad spectrum ATB regimen) for 14 days, followed by one ip. injection of 100 mg/kg of CTX on day 15 and oral feeding with $10^9$ bacteria (clone 708 versus clone CNCM I-4815) on day 16 prior to flow cytometric analyses of the splenocytes at day 22. The positive controls are represented by mice treated with CTX without prior ATB. A-C. Flow cytometric analyses of TH1, Tc1 or pTH17 cells. CD4+ TH1 cells expressing IFNγ or CXCR3 (A, left and right panel), CD8+ Tc1 expressing IFNγ (B) or CD4+ pTH17 cells expressing CXCR3 in the gate of live CCR6+ CD4+ T splenocytes (C). Concatenated data from 3 individual experiments including 5 mice/group. Anova statistical analyses: *p<0.05, p<0.01, *p<0.001.

Figure 31:
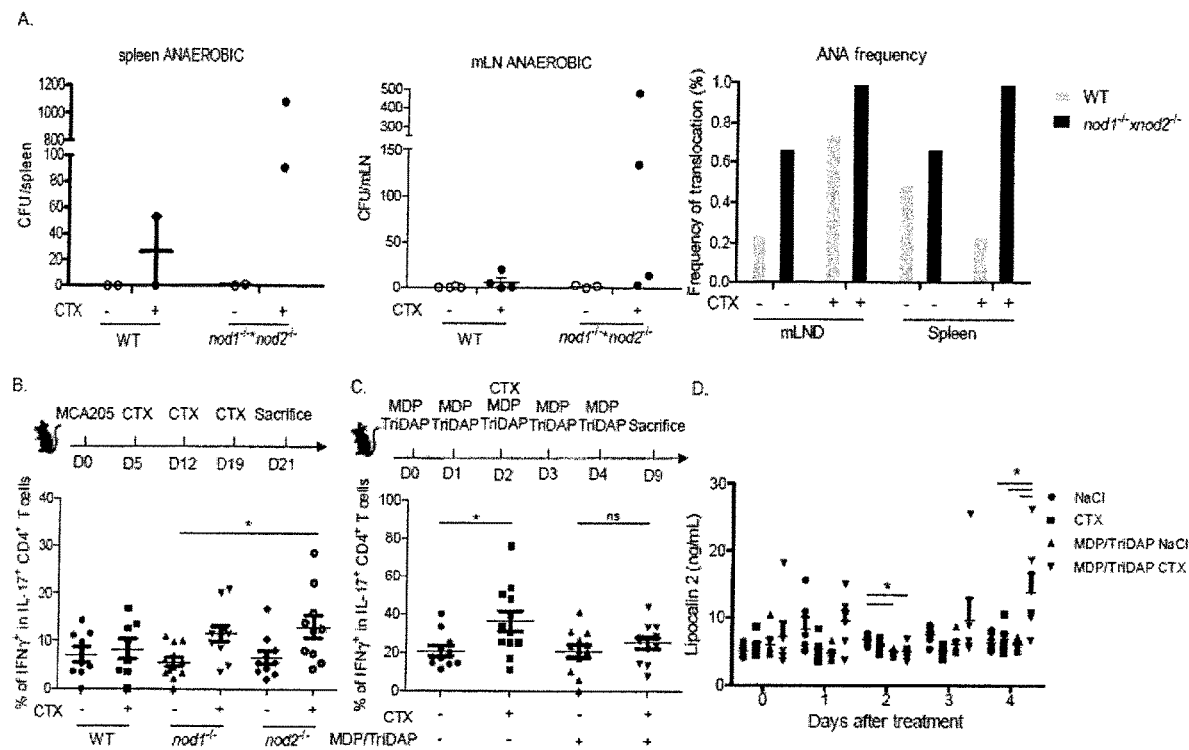

FIG. 31: Triggering of NOD receptors hampered bacterial translocation and priming of pTH17 cells by promoting the release of antimicrobial peptides. A. Enumeration of bacterial colonies in splenocytes 48 hrs post-CTX therapy in various mouse backgrounds. Splenic cells (left panel) and mesenteric LN (middle panel) harvested from C57BL/6 WT or NOD1$^{-/-}$×NOD2$^{-/-}$ mice were cultured in anaerobic conditions for 48 hours. Bacterial outgrowth was enumerated (number of colonies/plate and frequencies of positive plates/animal (right panel)) and eventually characterized by mass spectrometry for bacterial identification. B. Flow cytometric analyses of pTH17 cells. CD4+ T cells co-expressing IFN☐γ in the gate of live IL-17+ T splenocytes in WT versus NOD1 or NOD2 deficient mice C. Idem as in B. but experiment performed in WT animals treated with NOD agonists (MDP and TriDAP) according to the experimental setting aligned in the upper part of the graph. D. ELISA monitoring of lipocalin-2 in the feces of mice according to the experimental setting aligned in C. A representative experiment is shown for A and D. Concatenated data from 2-3 individual experiments including 3 mice/group are depicted in B-C. Anova statistical analyses: *p<0.05, p<0.01, *p<0.001.

Figure 32:
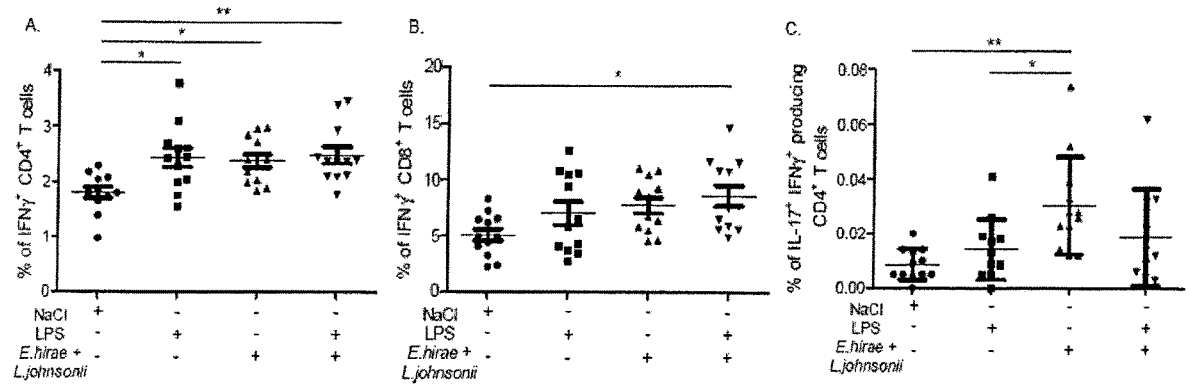

FIG. 32: LPS plays an inhibitory role on the capacity of *E. hirae*+*L. johnsonii* to elicit pTH17 cells. A-C. Comparisons between a TLR4 agonist and Gram positive bacteria for the elicitation of TH1 (A), Tc1 (B) and pTH17 (C) cells in the spleen. Experimental setting described in FIG. 25. but adding or not oral administration of LPS at a dosing of 500 ug/mouse repeated twice. Flow cytometric analysis of CD4+ T cells co-expressing IFNγ and IL-17 in the gate of live splenocytes. Concatenated data from 3 individual experiments including 5 mice/group. Anova statistical analyses: *p<0.05, p<0.01, *p<0.001.

Figure 33:
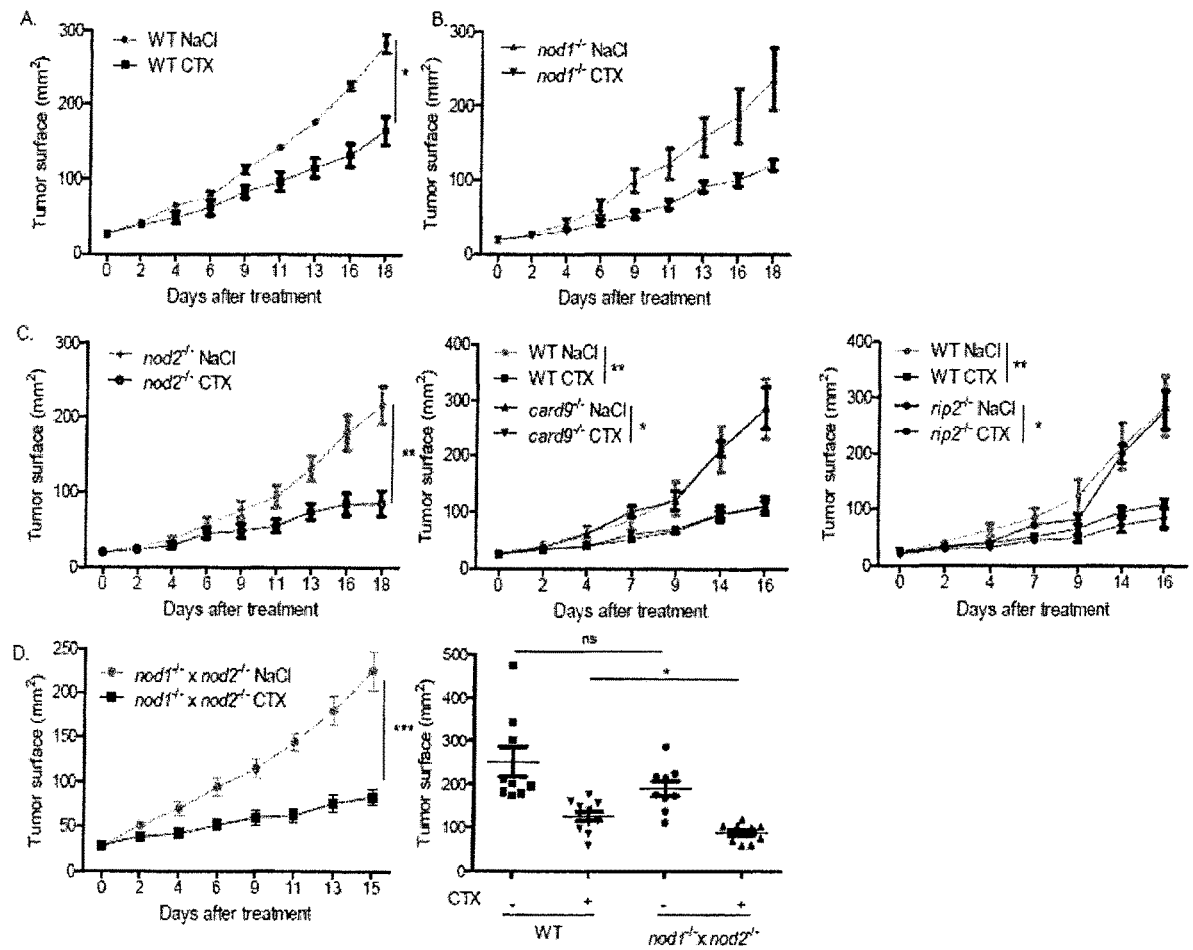

FIG. 33: Relative efficacy of CTX against sarcomas growing in various gene deficient-hosts. CTX was administered every other 7 days at 100 mg/kg ip. in WT (A), NOD1 (B), NOD2 (C, left panel), CARD9 (C, middle panel), RIP2 (C, right panel), NOD1×NOD2 (D, left panel and right panel)-deficient mice. Each graph depicts the means of 5 tumors/group in one representative growth kinetics. Student t'test: *p<0.05.

Figure 34:
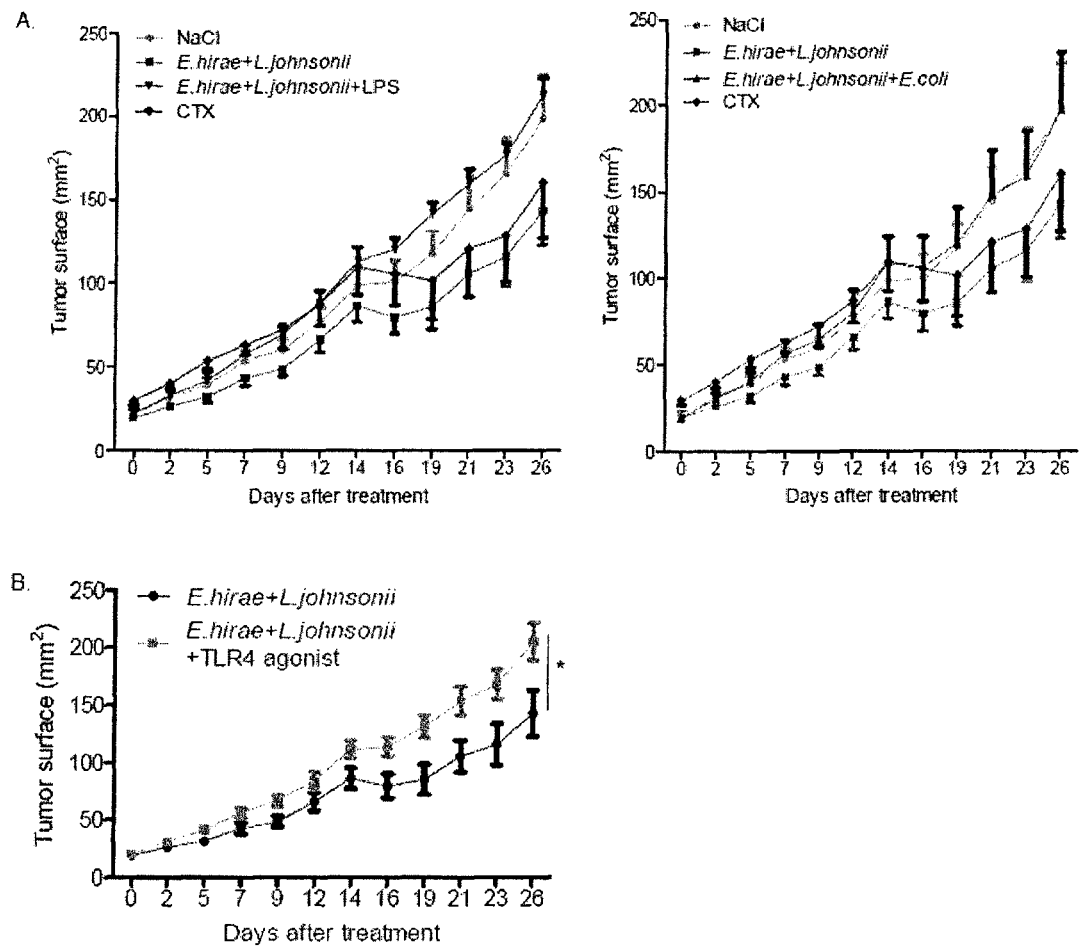

FIG. 34: Inhibitory effects of TLR4 agonists in the anticancer probiotic activity of the association of *E. hirae*+*L. johnsonii*. C57BL/6 mice were treated with vancomycine, streptomycine, ampicilline and colistine (broad spectrum ATB regimen) for 14 days, then inoculated sc. with MCA205 sarcoma, then treated with one ip. injection of 100 mg/kg of CTX on day 21 (and day 29) and oral feeding with LPS (A) 500 ug/mouse or $10^9$ bacteria (*E. coli*) (B) on day 22. Tumor growth kinetics were monitored biweekly for 1 month. The positive (CTX without ATB) and negative (PBS in ATB) controls are indicated. Means of tumor growth kinetics/5 mice/group in the presence of oral gavage with *E. hirae*+*L. johnsonii*+/−*E. coli* or LPS. A representative graph is shown in A and B and concatenated data for *E. coli*+LPS from 2 experiments including 5 mice/group are shown in C. Student t'test: *p<0.05.

FIG. 35: Principle component analysis of the pyrosequencing of 16srRNA of gene amplicons from stools of WT versus NOD1×NOD2 deficient mice treated or not with CTX. A. PCA. Stools have been harvested at day 7 post-CTX inoculation in naive C57BL/6 non tumor bearers. Feces from 4-5 animals/groups have been sequenced. The p value showing significant results between PBS and CTX therapies for gene deficient mice is indicated on the graph. B. Details of the families overrepresented post-CTX therapy in double KO mice. Analysis of most of the family members in the Bacteroidetes phylum. Heat map representation of the diversity and differences between the 4 groups (left panel) highlighting the enrichment in Porphyromonadaceae at the expense of Lachnospiraceae with CTX therapy as shown in statistical analyses presented on the right panel. C. Details of OTU post-CTX therapy in double KO mice, for *Barnesiella, Holdemania* and *Porphyromonas*.

Figure 36A:
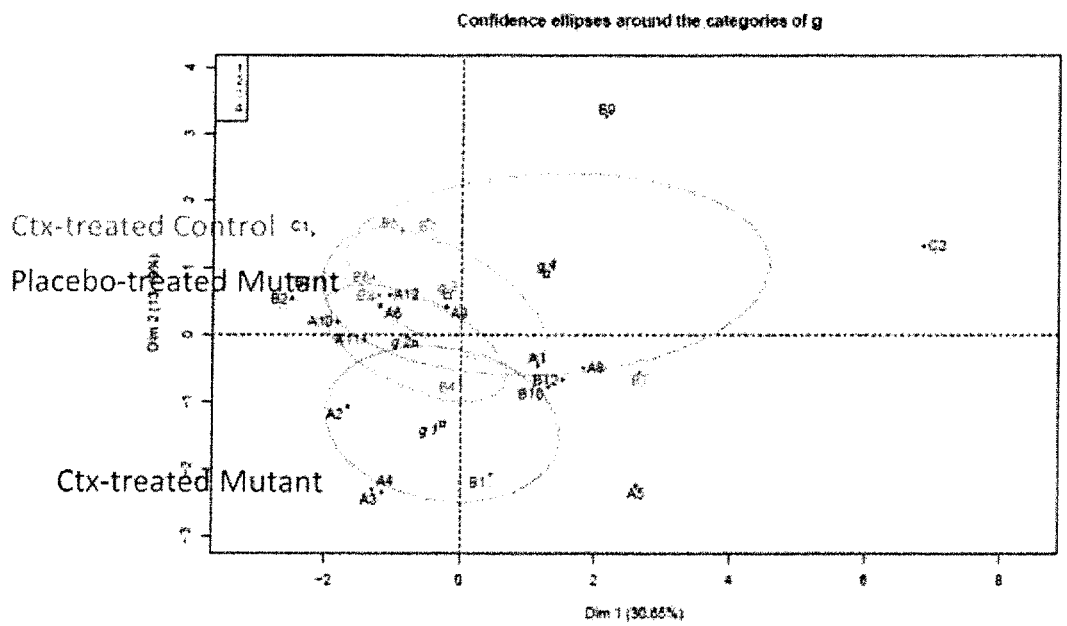
Figure 36B:
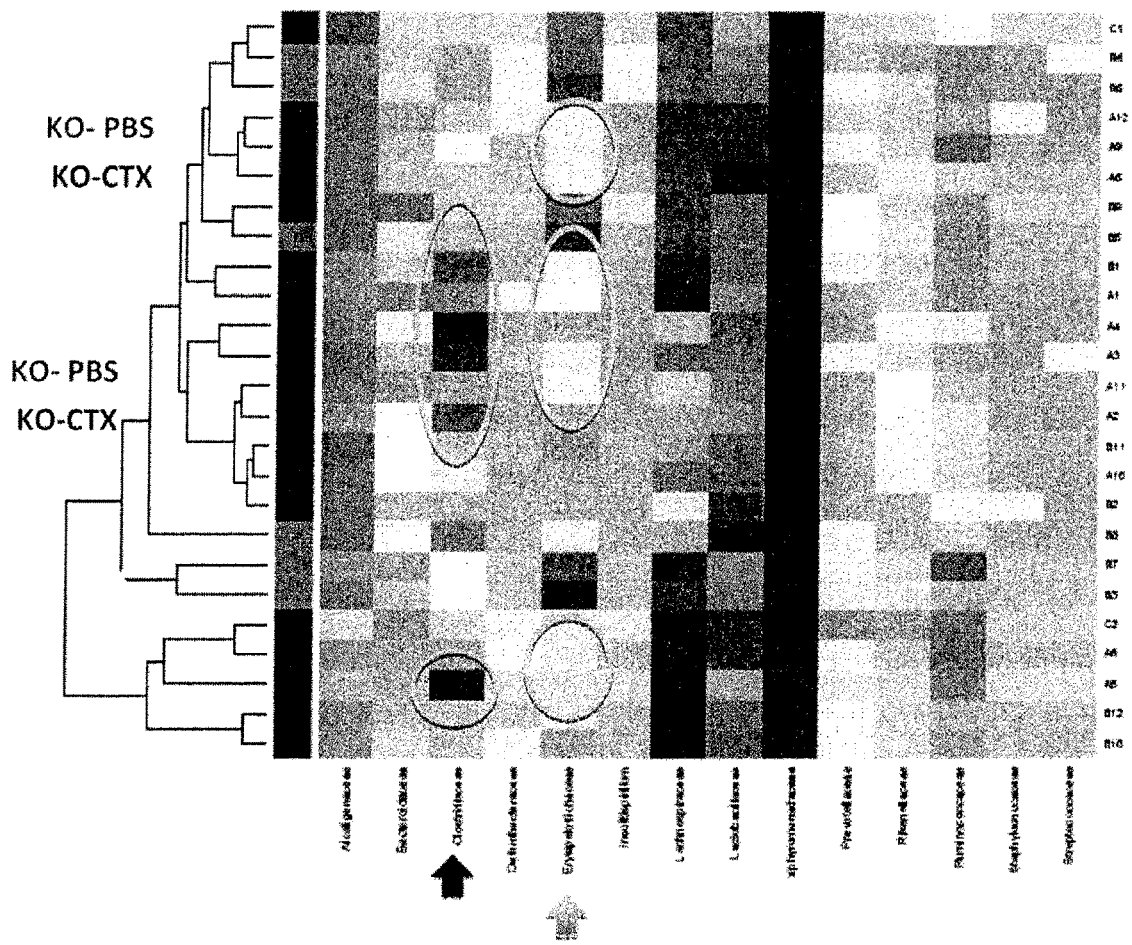

FIG. 36: Principle component analysis of the pyrosequencing of 16srRNA of gene amplicons of biofilms of small intestines from WT versus NOD1×NOD2 deficient mice treated or not with CTX. A. PCA. Biofilms of ilei have been harvested at day 7 post-CTX inoculation in naive C57BL/6 non tumor bearers. Small intestines from 4-5 animals/groups have been sequenced. The p value showing significant results between PBS and CTX therapies for gene deficient mice is indicated on the graph. B. Heat map representation of the diversity and differences between the 4 groups highlighting the enrichment in Clostridiaceae (mostly SFB, FIG. 40) at the expense of Erysipelotrichaceae with CTX therapy as shown in statistical analyses presented in Table 1.

Figure 37:
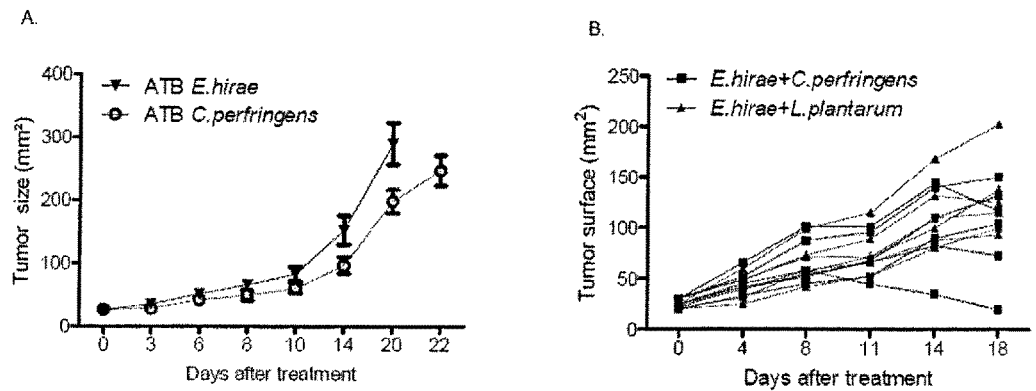

FIG. 37: Combination of the commensal *E. hirae* and the pathobiont *Clostridium perfringens*. Same experimental setting as in FIG. 26 but *C. perfringens* has been introduced by oral gavage as well. Tumor growth kinetics were monitored biweekly for 1 month, A. Tumor growth for the two groups *E. hirae* versus *C. perfringens*. B. Tumor growth kinetics in the presence of oral gavage with *E. hirae*+*L. plantarum* versus *E. hirae*+*Clostridium perfringens*. Two experiments including 5 mice/group are shown. Anova statistical analyses: *p<0.05.

Figure 38:
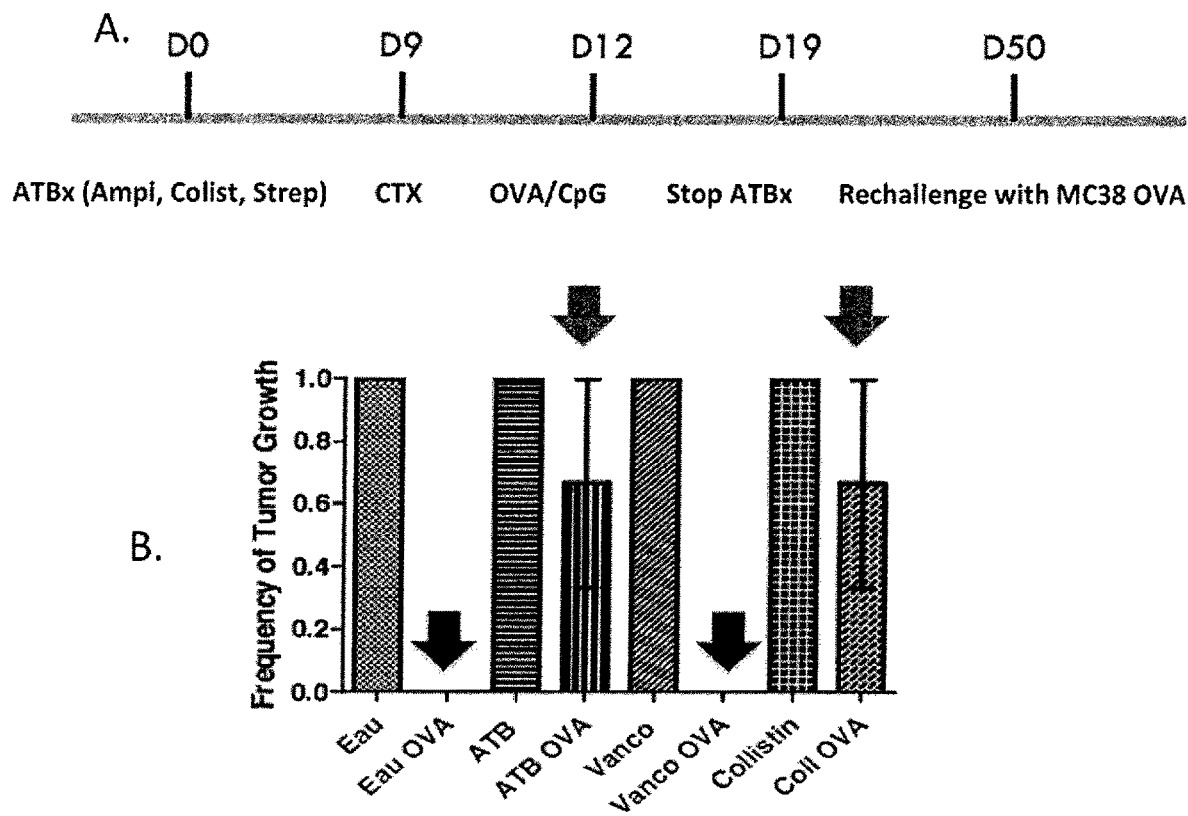

FIG. 38: Anticancer vaccines combined with CTX promote a long lasting anticancer immunity which depends on gut Gram negative bacteria. A. Experimental setting. C56BL/6 mice were treated with broad spectrum ATB (ampicilline, colistine, streptomycine) or vancomycine (which only kills Gram+ bacteria) or colistine (which only kills Gram− bacteria) for 9 days, received one ip, injection of CTX (100 mg/kg), followed 3 days later by vaccination with OVA protein in CpG adjuvants (or mock vaccines). ATB were stopped after 20 days and animals were left untreated under observation for 1 month. At day 50, all mice were rechallenged with a lethal dose of 10× times the MTD of MC38-OVA$^{dim}$ tumor cells sc. B. Animals were scored on the basis of tumor outgrowth (featuring no or weak memory T cell response). The percentages of tumor-free mice was recorded for 2 experiments comprising 5 mice/group.*Anova test: p<0.05.

Figure 39:
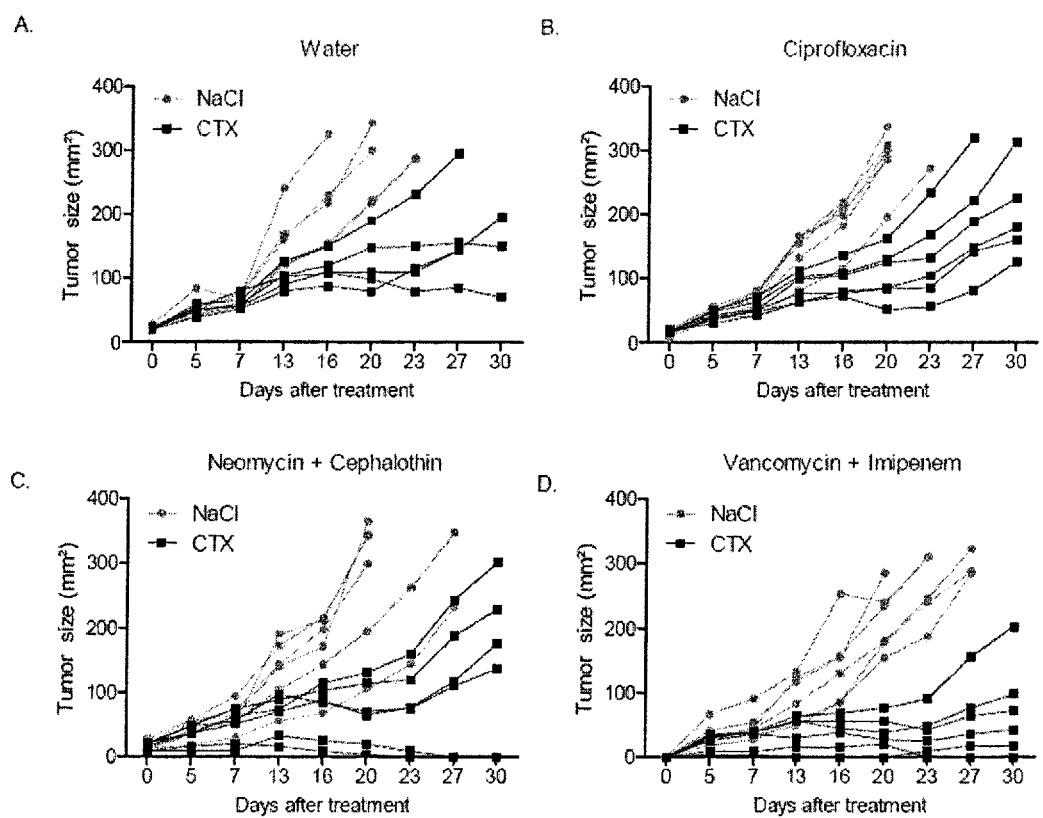

FIG. 39: Effects of ATB regimen on the efficacy of CTX. Distinct ATB regimen (Zhang Y et al. Toxicology and Applied Pharmacology 277 (2014) 138-145) were administered for 15 days prior to tumor inoculation and CTX therapy every other 13 days. Tumor outgrowth was monitored with a caliper twice a week. Protocols reported to reduce Firmicutes, most specifically Clostridiae eventually decreasing the *Firmicutes/Bacteroides* ratio (such as the combination of neomycine+cephalothin or vancomycine+imipenem) (panel C-D) could improve the CTX-induced antitumor effects while cifloxacin (which, in contrast, induced a marked suppression of Bacteroidetes) was not efficient (panel B). Of note, the combination of neomycine+cephalothin could augment SFB representativity while vanco+imipenem increased that of *Porphyromonas*. Each experiment contains several groups of 5 mice. *Anova test: p<0.05.

FIG. 39: Table of data relating to Example 9. The table is presented on four drawing sheets, organized sequentially so that FIG. 40 (cont.) is to the right of FIG. 40, FIG. 40 (cont. 1) is to the right of FIG. 40 (cont.), and FIG. 40 (cont. 2) is to the right of FIG. 40 (cont. 1). The rows are presented in the same order on each sheet.

DETAILED DESCRIPTION OF THE PREFERRED EMBODIMENTS

In the present text, the following general definitions are used:

Gut Microbiota

The "gut microbiota" (formerly called gut flora or microflora) designates the population of microorganisms living in the intestine of any organism belonging to the animal kingdom (human, animal, insect, etc.). While each individual has a unique microbiota composition (60 to 80 bacterial species are shared by more than 50% of a sampled population on a total of 400-500 different bacterial species/individual), it always fulfils similar main physiological functions and has a direct impact on the individual's health:

- it contributes to the digestion of certain foods that the stomach and small intestine are not able to digest (mainly non-digestible fibers);
- it contributes to the production of some vitamins (B and K);
- it protects against aggressions from other microorganisms, maintaining the integrity of the intestinal mucosa;
- it plays an important role in the development of a proper immune system;
- a healthy, diverse and balanced gut microbiota is key to ensuring proper intestinal functioning.

Taking into account the major role gut microbiota plays in the normal functioning of the body and the different functions it accomplishes, it is nowadays considered as an "organ". However, it is an "acquired" organ, as babies are born sterile; that is, intestine colonisation starts right after birth and evolves afterwards.

The development of gut microbiota starts at birth. Sterile inside the uterus, the newborn's digestive tract is quickly colonized by microorganisms from the mother (vaginal, skin, breast, etc.), the environment in which the delivery takes place, the air, etc. From the third day, the composition of the intestinal microbiota is directly dependent on how the infant is fed: breastfed babies' gut microbiota, for example, is mainly dominated by *Bifidobacteria*, compared to babies nourished with infant formulas.

The composition of the gut microbiota evolves throughout the entire life, from birth to old age, and is the result of different environmental influences. Gut microbiota's balance can be affected during the ageing process and, consequently, the elderly have substantially different microbiota than younger adults.

While the general composition of the dominant intestinal microbiota is similar in most healthy people (4 main phyla, i.e., Firmicutes, Bacteroidetes, Actinobacteria and Proteobacteria), composition at a species level is highly personalised and largely determined by the individuals' genetic, environment and diet. The composition of gut microbiota may become accustomed to dietary components, either temporarily or permanently. Japanese people, for example, can digest seaweeds (part of their daily diet) thanks to specific enzymes that their microbiota has acquired from marine bacteria.

Dysbiosis

Although it can adapt to change and has a high resilience capacity, a loss of balance in gut microbiota composition may arise in some specific situations. This is called "dysbiosis", a disequilibrium between potentially "detrimental" and known "beneficial" bacteria in the gut or any deviation to what is considered a "healthy" microbiota in terms of main bacterial groups composition and diversity. Dysbiosis may be linked to health problems such as functional bowel disorders, inflammatory bowel diseases, allergies, obesity and diabetes. It can also be the consequence of a treatment, such as a cytotoxic treatment or an antibiotic treatment.

A specific dysbiosis can be highlighted depending on the pathogenic condition. For instance, patients with Crohn's disease, a chronic inflammatory bowel disease, present a microbiota with reduced percentages and diversity of bacteria belonging to the Firmicutes phylum, and mostly from the *Clostridium leptum* (cluster IV) group (Manichanh et al., 2006; Sokol et al., 2006). Generally, decreased percentages of bacteria from the Lachnospiraceae family can be observed. Moreover mucosa-associated microbiota of these patients is depleted in bacteria from the *Bifidobacterium* and *Lactobacillus* genera toward increased levels of potentially pathogenic bacteria such as specific strains of *Escherichia coli* with adherent and invasive phenotypes (AIEC) (Darfeuille-Michaud et al. 2011, 2004; Joossens et al., 2011).

To the contrary, patients with obesity and metabolic disorders have higher proportions of bacteria belonging to the Firmicutes phylum and lower levels of *Escherichia coli* in their feces (Ley et al., 2005; Turnbaugh et al., 2009). An increased in proportions of *E. coli* in these patients has been associated with weight loss following bariatric surgery and lower levels of serum leptin (Furet et al., 2010).

In patients with colorectal cancer (CRC), however, gut microbial dysbiosis relates to enrichment in bacterial species from the *Bacteroides* genus and decrease of *Faecalibacterium* and *Roseburia* genera belonging species (Sobhani et al., 2011; Wu et al., 2013). Specifically, *Fusobacterium* and *Campylobacter* genera were found to be consistently increased in both feces and mucosa of CRC patients.

In the context of cancer, "beneficial or "favorable" bacteria are essentially *Lactobacillus* and *Bifidobacterium*, and "detrimental" or "unfavorable" bacteria are essentially the species *Parabacteroides distasonis* and *Faecalibacterium prausnitzii*, the genera *Gemmiger, Alistipes* and *Clostridium* Cluster IV. (*Clostridium leptum* group).

Antineoplastic Treatments

"Antineoplastic treatments" herein designate any treatment for cancer except surgery. They include chemotherapy, hormonal and biological therapies, and radiotherapy.

Chemotherapy

"Chemotherapy" is defined herein as the treatment of cancer with one or more "chemotherapeutic agents". Chemotherapeutic agents are chemical molecules which act by killing cells that divide rapidly, one of the main properties of most cancer cells. Several categories of chemical agents exist:

alkylating agents (further defined below);
spindle poisons such as mebendazole, colchicine;
mitotic inhibitors (including taxanes (paclitaxel (Taxol®), docetaxel (Taxotere®)) and vinca alkaloids (e.g.: vincristine, vinblastine, vinorelbine, vindesine)),
cytotoxic/antitumor antibiotics: such as anthracyclines (e.g.: doxorubicin, daunorubicin, adriamycine, idarubicin, epirubicin and mitoxantrone, valrubicin), *streptomyces* (e.g.: actinomycin, bleomycin, mitomycin, plicamycin)
anti-metabolites (such as pyrimidine analogues (e.g.: fluoropyrimidines analogs, 5-fluorouracil (5-FU), floxuridine (FUDR), Cytosine arabinoside (Cytarabine), Gemcitabine (Gemzar®), capecitabine; purine analogues (e.g.: azathioprine, mercaptopurine, thioguanine, fludarabine, pentostatin, cladribine, capecitabine, clofarabine); folic acid analogues (e.g.: methotrexate, folic acid, pemetrexed, aminopterin, raltitrexed, trimethoprim, pyrimethamine),
topoisomerase inhibitors (e.g.: camptothecins: irinotecan, topotecan, amsacrine, etoposide, etoposide phosphate, teniposide);
DNA methyltransferase inhibitors: 2'-deoxy-5-azacytidine (DAC), 5-azacytidine, 5-aza-2'-deoxycytidine, 1-[beta]-D-arabinofuranosyl-5-azacytosine, dihydro-5-azacytidine;
vascular disrupting agents, such as flavone acetic acid derivatives, 5,6-dimethylxanthenone-4-acetic acid (DMXAA) and flavone acetic acid (FAA);
also other chemotherapeutic drugs such as aprepitant, bortezomib (Velcade®, Millenium Pharmaceuticals), imatinib mesylate (Gleevec®), carmustine (BCNU), lomustine (CCNU), tamoxifen, gefitinib, erlotinib, carboxyamidotriazole, efaproxiral, tirapazamine, xcytrin, thymalfasin, vinflunine.

Alkylating Agents

"Alkylating agents" are so named because of their ability to alkylate many molecules, including proteins, RNA and DNA. This ability to bind covalently to DNA via their alkyl group is the primary cause for their anti-cancer effects, since it provokes cell apoptosis. Alkylating agents are cell cycle-independent drugs, and their effects are usually dose dependent.

The subtypes of alkylating agents are the nitrogen mustards, nitrosoureas, tetrazines, aziridines, and non-classical alkylating agents. Nitrogen mustards include mechlorethamine, cyclophosphamide, melphalan, chlorambucil, ifosfamide and busulfan. Nitrosoureas include N-Nitroso-N-methylurea (MNU), carmustine (BCNU), lomustine (CCNU) and semustine (MeCCNU), fotemustine and streptozotocin. Tetrazines include dacarbazine, mitozolomide and temozolomide. Aziridines include thiotepa, mytomycin and diaziquone (AZQ). Non-classical alkylating agents include procarbazine and hexamethylmelamine.

Throughout the present application, "alkylating-like agents", which are platinum-based chemotherapeutic drugs (also termed "platinum analogues") and act in a similar manner as alkylating agents, will be included in the category of "alkylating agents". These agents do not have an alkyl group, but nevertheless damage DNA. They permanently coordinate to DNA to interfere with DNA repair. Example of this subcategory of alkylating agents as herein defined are platinum, cisplatin, carboplatin, nedaplatin, oxaliplatin, satraplatin and triplatin tetranitrate.

Biological Therapies

Anti cancer "biological therapies" involve the use of living organisms, substances derived from living organisms, or laboratory-produced versions of such substances to treat cancer, by targeting either the cancer cells directly, or by stimulating the body's immune system to act against cancer cells ("immunotherapy"). Biological therapies include monoclonal antibodies (including those targeting cancer cell surface, e.g. rituximab and alemtuzumab; anti-CTLA4 Mabs, such as ipilimumab; targeting growth factors, e.g.: bevacizumab, cetuximab, panitumumab and trastuzumab; anti-PD-1 Mabs; anti-Tim3 Mabs; anti-ICOS Mabs), immunoconjugates (e.g.: $^{90}$Y-ibritumomab tiuxetan, $^{131}$I-tositumomab, and ado-trastuzumab emtansine), cytokines (including interferons such as IFNα; interleukins such as IL-2, IL-11, G-CSM, GM-CSF), therapeutic vaccines (e.g.: Sipuleucel-T (Provenge®)), the bacterium bacillus Calmette-Guérin, cancer-killing viruses, gene therapy, and adoptive T-cell transfer.

Prebiotics, Probiotics and Synbiotics

"Prebiotics" are non-digestible food ingredients that stimulate the growth and/or activity of bacteria in the digestive system in ways claimed to be beneficial to health. They usually are selectively fermented ingredients that allow specific changes, both in the composition and/or activity of the gut microbiota.

"Probiotics" are micro-organisms that have claimed health benefits when consumed. Probiotics are commonly consumed as part of fermented foods with specially added active live cultures, such as in yogurt, soy yogurt, or as dietary supplements. Generally, probiotics help gut microbiota keep (or re-find) its balance, integrity and diversity. The effects of probiotics are usually strain-dependent.

"Synbiotics" refer to nutritional supplements combining probiotics and prebiotics in a form of synergism, hence synbiotics. Using prebiotics and probiotics in combination is often described as synbiotic, but the United Nations Food & Agriculture Organization (FAO) recommends that the term "synbiotic" be used only if the net health benefit is synergistic.

Cancer, Treatment, Etc.

As used herein, "cancer" means all types of cancers. In particular, the cancers can be solid or non solid cancers. Non limitative examples of cancers are carcinomas or adenocarcinomas such as breast, prostate, ovary, lung, pancreas or colon cancer, sarcomas, lymphomas, melanomas, leukemias, germ cell cancers and blastomas.

As used herein, the terms "treat", "treatment" and "treating" refer to any reduction or amelioration of the progression, severity, and/or duration of cancer, particularly a solid tumor; for example in a breast cancer, reduction of one or more symptoms thereof that results from the administration of one or more therapies.

Other definitions will be specified below, when necessary.

According to a first aspect, the present invention pertains to a probiotic composition comprising bacteria selected from the group consisting of *Enterococcus* hirae, *Lactobacillus johnsonii*, segmented filamentous bacteria (SFB), *Porphyromonas, Barnesiella, Holdemania* and mixtures thereof, for use as an adjuvant to an antineoplastic treatment administered to a cancer patient. According to a preferred embodiment of the probiotic composition of the invention, said composition comprises *Enterococcus hirae* and at least one strain selected amongst *Porphyromonas, Barnesiella* and *Holdemania*. A preferred strain of *Enterococcus hirae* for the above compositions is the strain deposited on Nov. 7, 2013 at the Collection Nationale de Cultures de Microorganismes (CNCM), under the number I-4815. Such a composition can advantageously further comprise a *Lactobacillus johnsonii* strain such as *Lactobacillus johnsonii* strain LJFS001B, deposited on Nov. 15, 2013 at the Collection Nationale de Cultures de Microorganismes (CNCM), under the number I-4823.

The above probiotic compositions can advantageously be formulated for oral administration and administered either as food supplements or as functional food. The skilled artisan knows a variety of formulas which can encompass living or killed microorganisms and which can present as food supplements (e.g., pills, tablets and the like) or as functional food such as drinks, fermented yoghurts, etc.

According to a preferred embodiment, the probiotic composition according to the invention is administered to a patient in need thereof after the administration of an antineoplastic treatment, for example a chemotherapeutic agent such as cyclophosphamide (CTX) to said patient. For example, the probiotic composition can be administered the same day as a CTX dose, or after a few days of treatment. In case of metronomic CTX administration, the probiotic composition can be administered daily, after each CTX uptake or even at the same time. Alternatively, the probiotic composition according to the invention is administered to a patient in need thereof before the administration of an antineoplastic treatment.

Some chemotherapeutic agents, especially CTX, have been described as efficacious adjuvants to anticancer vaccines. A particularly useful application of the probiotic compositions according to the present invention is their use in combination with such a chemotherapeutic agent, for further increasing the efficacy of cancer vaccination.

A method for treating a cancer patient, comprising administering a probiotic bacterial composition such as above-described, prior to and/or after administering a chemotherapeutic agent, either alone or combined to an anticancer vaccine, to said patient, is also part of the present invention.

Although the above compositions can be appropriately administered to any patient treated with and antineoplastic treatment such as chemotherapy (alone or in combination with an antitumor vaccine), they are particularly useful for patients who have a dysbiosis with an under-representation of species present in said probiotic composition.

Another aspect of the present invention is the use of a combination of a chemotherapeutic agent and of an antibiotic composition which decreases the firmicutes/bacteroidetes ratio, specifically augments SFB and/or Porphyromonadaceae and/or decreases *Clostridium* group IV in the gut microbiota of an individual when administered to said individual, for treating a cancer. According to a particular embodiment, the antibiotic composition comprises or consists of a combination of vancomycin and imipenem. According to another particular embodiment, the antibiotic composition comprises or consists of a combination of neomycin and cephalothin. Advantageously, the chemotherapeutic agent used in combination with an antibiotic composition as described above is cyclophosphamide (CTX).

As used herein, the term "combination" refers to the use of more than one agent (e.g., vancomycin+imipenem and CTX). The use of the term "combination" does not restrict the order in which the therapeutic agents are administered to the patient, although it is preferable to administer the antibiotic cocktail prior to or simultaneously with the chemotherapeutic agent. For example, vancomycin and imipenem can be administered prior to CTX (e.g., 24 hours, 48 hours, 72 hours, 96 hours, 1 week, 2 weeks, 3 weeks, 4 weeks before), either punctually or several times (for example, each day), preferably for 3 to 7 days before the antineoplastic treatment is administered. Advantageously, the antibiotic composition is administered before administration of a chemotherapeutic drug, in order to modulate the patient's gut microbiota to optimize the effect of said chemotherapeutic drug (such as CTX). The present invention hence provides a method for treating a cancer patient, comprising administering an antibiotic composition which decreases the firmicutes/bacteroidetes ratio, specifically augments SFB and/or Porphyromonadaceae and/or decreases *Clostridium* group IV in the gut microbiota of an individual when administered to said individual, prior to administering a chemotherapeutic drug (either alone or in combination with an anticancer vaccine).

The present invention also pertains to the use of an antibiotic composition which decreases the firmicutes/bacteroidetes ratio, specifically augments SFB and/or Porphyromonadaceae and/or decreases *Clostridium* group IV in the gut microbiota of an individual when administered to said individual, as an adjuvant therapy to potentiate the anticancer effects of a chemotherapeutic agent administered to said patient. Indeed, as illustrated in the experimental part below, it can be useful to modulate the gut microbiota of a patient, through the use of antibiotics and/or probiotics, for increasing the anticancer effects of a chemotherapeutic agent such as, for example, CTX. Antibiotic compositions such as vancomycin+imipenem and neomycin+cephalothin are particularly useful to this aim.

Another object of the present invention is an immunogenic composition comprising fragments of bacteria selected from the group consisting of *Enterococcus hirae, Lactobacillus johnsonii, Enterococcus faecalis*, segmented filamentous bacteria (SFB), *Porphyromonas, Barnesiella, Holdemania* and mixtures thereof, for use as an adjuvant to an antineoplastic treatment administered to a cancer patient. According to a preferred embodiment, the immunogenic composition, comprises fragments of *Enterococcus hirae*, more preferably fragments of the strain CNCM I-4815, together with fragments of at least one strain selected from the group consisting of *Porphyromonas, Barnesiella* and *Holdemania*.

The immunogenic compositions according to the invention are preferably formulated for subcutaneous or intramuscular administration. They can advantageously be administered before, at the same time or after administration of a chemotherapeutic agent such as CTX, in order to indice an immune response which will have an adjuvant effect to the treatment.

The invention further pertains to cell compositions and their use in adoptive cell transfer in combination with a chemotherapeutic agent. Techniques for obtaining various immune cell types from a patient and ex vivo pulse or educate such cells are well known by the skilled artisan. Such techniques were described, inter allia, by Caux et al. (1996), Sallust (1994), Palucka (2013), Vanlint (2014), Arrntzen (2008), and Lesterhuis (2008). A first cell composition according to the invention is a cell composition comprising antigen presenting cells (APC) such as dendritic cells (DC) which have been pulsed ex vivo with a probiotic composition or with an immunogenic composition as above-described. According to a preferred embodiment, the antigen presenting cells present in the cell composition have also been pulsed ex vivo with a tumor antigen.

The cell compositions according to the present invention are particularly useful for treating a cancer, by combining adoptive cell transfer with an antineoplastic treatment. Depending on the clinical context, the physician will decide how to administer such a cell composition. In particular, these compositions can be administered by intra-nodal injection, intravenous injection or subcutaneous injection.

According to another adoptive transfer method of the present invention, the above APC compositions can be used to ex vivo "educate" T cells obtained from the patient, before re-injecting these educated T cells, especially memory T cells, to the patient. A cell composition comprising memory T cells obtained by a process comprising ex vivo contacting T cells from a cancer patient with an APC composition as above-described, is hence also part of the present invention. Such a T cell composition can advantageously be used in adoptive cell transfer as an adjuvant to potentiate the effects of an antineoplastic treatment such as a chemotherapy (especially CTX administration), administered alone or in combination with an antitumoral vaccination. As for the dendritic cells, the T cells can be administered by intra-nodal injection, intravenous injection or subcutaneous injection, depending on the cinical context.

The present invention also relates to a method for ex vivo obtaining T cells able to improve the anticancer activity of a chemotherapeutic drug, comprising ex vivo expanding a polyclonal T cell line or bulk autologous T cells with dendritic cells (DC) presenting peptides from *Enterococcus hirae, Lactobacillus johnsonii*, segmented filamentous bacteria (SFB), *Porphyromonas, Barnesiella* and/or *Holdemania*.

Another aspect of the present invention is an in vitro method of identifying a patient likely to be a good responder to a chemotherapy, comprising determining the functionality of TLR 4, NOD1 and NOD2 in said patient, wherein if said patient lacks a functional TLR 4 and/or NOD1/CARD4 (rs2006847, rs2066844, rs2066845, rs2066842, ND(1)+ 32656, rs2075820, . . . ) and/or NOD2/CARD15 (such as p.R702W, p.G908R, p.Leu1007fsX1008), the patient is identified as a good responder to a chemotherapy (all except anthracyclines and oxaplatin and radiotherapy). Two cosegregating single nucleotide polymorphisms (SNPs)—Asp299Gly and Thr399Ile—have been identified within the gene encoding TLR4. These SNPs are present in approximately 10% of white individuals, and have been found to be positively correlated with several infectious diseases. In a particular embodiment of this method, the presence or absence of one or both of these SNPs is determined, for example by PCR or by any other method known by the skilled artisan.

According to another embodiment, the present invention pertains to a method for in vitro determining whether a cancer patient can benefit from an antineoplastic treatment, comprising the following steps:

(i) from an appropriate biological sample from said patient, determining the relative abundance of "unfavorable" bacteria in the specific context of cancer and chemotherapy, for example bacteria from a group comprising or consisting of the species *Parabacteroides distasonis* and *Faecalibacterium prausnitzii*, bacteria from the genera *Gemmiger, Alistipes* and *Clostridium* cluster IV (group *Clostridium leptum*; as described in the taxonomic description of *Clostridium* bacteria by Collins et al) in said patient's gut microbiota; Optionally, in the same biological sample, the relative abundance of "favorable" bacteria in the specific context of cancer and chemotherapy, for example bacteria from the genera *Lactobacillus* and *Bifidobacterium*, is also determined; for example if a decreased ratio of Firmicutes/Bacteroidales is observed, the presence of bacteria from the family Porphyromonadaceae, SFB, is also determined;

(ii) determining the presence or absence of an intestinal dysbiosis;

wherein an intestinal dysbiosis with an over-representation of "unfavorable" bacteria from the taxons recited in step (i) indicates that the patient will not be a good responder to antineoplastic treatment.

In what precedes, the "relative abundance" is defined as the number of bacteria of a particular taxonomic level (from phylum to species) as a percentage of the total number of bacteria in the biological sample. This relative abundance can be assessed, for example, by measuring the percentage of 16S rRNA gene sequences present in the sample which are assigned to these bacteria. It can be measured by any appropriate technique known by the skilled artisan, such as 454 pyrosequencing and quantitative PCR of these specific bacterial 16S rRNA gene markers, as described in the experimental part below, or quantitative PCR of any gene specific for a bacterial group.

In the present text, a "good responder to a treatment", also called a "responder" or "responsive" patient or in other words a patient who "benefits from" this treatment, refers to a patient who is affected with a cancer and who shows or will show a clinically significant relief in the cancer after receiving this treatment. The disease clinical data may be assessed according to the standards recognized in the art, such as immune-related response criteria (irRC), WHO or RECIST criteria.

According to a particular embodiment, the biological sample is a biofilm of a biopsy (preferably of a large biopsy) of duodenum or ileum mucosae obtained from the patient. For example, this biopsy can have been obtained during a specific surgery in pancreatic, stomach, biliary tract or colon cancers.

According to another embodiment, which concerns any type of cancer, the biological sample is a sample of feces obtained from the patient. This sample can have been collected at diagnosis, for example, or at any moment before deciding the beginning of the treatment.

When an intestinal dysbiosis with an over-representation of "unfavorable" bacteria as defined above is observed, this shows that the patient requires a treatment to balance the gut microbiota prior to starting the antineoplastic treatment, or as an adjuvant of said treatment (e.g.: prebiotics or probiotics administration before/when starting a chemotherapy). Hence, decision can be made to adapt the patient's regimen (providing pre- or probiotics) during a period of time (for example, a few weeks) before beginning the antineoplastic treatment.

According to another aspect, the present invention pertains to a method for in vitro determining whether an antineoplastic treatment is to be continued or stopped for a cancer patient, comprising the following steps:

(i) from a biological sample from said patient, obtained at least 3 weeks after the beginning of the antineoplastic treatment, preferably 6-9 weeks after the beginning of the antineoplastic treatment (corresponding to three cycles of chemotherapy), analyzing memory $CD4^+$ T cell response directed against at least one commensal species of bacteria (preferably at least 2 and more preferably at least 3, 4 or more commensals);

(ii) for each commensal species against which the $CD4^+$ T cell response is analyzed, classifying the response in one of the following categories:
no memory $CD4^+$ T cell response;
memory response of a Th10:Tr1/Treg phenotype;
memory response of a Th1 phenotype,
wherein if a memory response of a Th1 phenotype is observed for at least one commensal species, the antineoplastic treatment is continued, and in absence of such a response, the antineoplastic treatment is stopped or compensated with appropriate probiotics (see below).

This pharmacodynamic assay is particularly useful to predict, after 3-9 weeks of a chemotherapy (1-3 cycles of chemotherapy), preferably after 6-9 weeks (2-3 cycles) of chemotherapy, whether this chemotherapy is likely to trigger an adjuvant immune response and a clinical benefit.

In order to classify the responses, the secretions of IL-2, TNFα, IFNγ and IL-10 are measured in ex vivo restimulation assays. In a preferred embodiment, a first assay is done before the beginning of the treatment, in order to compare the cytokine secretion profile after a few weeks of treatment to that observed pre-treatment. These assays can be performed, for example, using patients' autologous monocytes loaded with defined bacteria and incubated with $CD4^+$ $CD45RO^+$ T cells purified from autologous blood. The response will be classified in the third (favourable) category if it is of a Th1 phenotype, i.e., if restimulation triggers a significant secretion of IL-2, TNFα and IFNγ, and a low secretion of IL-10, especially when comparing the results obtained post- to pre-treatment. Typically, for a patient having a response of the Th1 phenotype, at least a 2-fold increase of IFNγ secretion is observed post-treatment (compared to pre-treatment). The first category (no memory $CD4^+$ T cell response) corresponds to the absence of significant cytokine secretion in restimulation assays post-treatment, whereas the second category corresponds to a response in which the IL-10 secretion in a restimulation assay post-treatment is superior to that observed pre-treatment.

According to a particular embodiment of the above method, the memory $CD4^+$ T cell responses directed against at least two species selected amongst *Lactobacillus johnsonii, Enterococcus hirae* and *Enterococcus faecalis* are analyzed. Preferably, the responses directed against 2 of these, and more preferably against all of these, are assessed.

One particularly advantageous aspect of this pharmacodynamic method is that it can be performed using a blood sample. Of course, it can be done for patients having any kind of cancers.

According to a third aspect, the present invention pertains to a method for in vitro determining the biological effects of a neoadjuvant antineoplastic treatment which has been administered to a patient, comprising the following steps:

(i) from an appropriate biological sample from said patient, determining the relative abundance of "favorable" bacteria in said microbiota;

(ii) from the same biological sample, determining the relative abundance of "unfavorable" bacteria in said gut microbiota;

(iii) calculating the ratio between the abundance of favorable bacteria and the abundance of unfavorable bacteria, wherein if said ratio is above a predetermined threshold, the result indicates that the neoadjuvant antineoplastic treatment induced a T-bet/Th1 local and systemic immune response.

To perform the above method, the "favorable" bacteria can be those from a group comprising or consisting of the genera *Lactobacillus* and *Bifidobacterium*, and the "unfavorable" bacteria can be those from a group comprising or consisting of the species *Parabacteroides distasonis* and *Faecalibacterium prausnitzii* and the genera *Gemmiger, Alistipes* and *Clostridium* Cluster IV (*Clostridium leptum* group).

The skilled artisan will determine the appropriate threshold depending on the technique which is used to determine the relative abundance of bacteria from each group (for example, pyrosequencing or quantitative PCR) and depending on the definition of each group of patients. Indeed, a unique threshold cannot be determined for all cancer patients, and the ratio must be appreciated having regard to several factors, including the patient's health and food habits.

For performing the above method, the biological sample preferably is a biofilm from a biopsy (preferably from a large biopsy) of duodenum or ileum mucosae obtained from the patient. For example, this biopsy can have been obtained during a specific surgery in pancreatic, stomach, biliary tract or colon cancers.

Importantly, the methods described above can be performed to prognosticate or diagnose the responsiveness of a cancer patient to any antineoplastic treatment as defined above, including chemotherapies, biological therapies, radiotherapies, hormone therapies, etc. In particular, these methods can be advantageously used to assess the (potential) benefit, for a cancer patient, of a chemotherapy, more particularly with an alkylating agent or a platinum salt such as any of those cited above, and/or an anti-tumor vaccine. The experimental data below clearly describe the role of microbiota on the immune response induced by cyclophosphamide (Examples 1, 3 and 4), doxorubicine (see at least FIG. 14) and oxaliplatine (Example 2). Interestingly, Examples 3 to 5 show that the results obtained in mice can be extrapolated to humans. The experimental data show that a "beneficial" microbiota also has a positive impact on the efficiency of a treatment by anthracyclins (FIG. 8) and obviously, if bacterium species having an immunomodulatory role, such as *Faecalibacterium prausnitzii*, are too abundant in the gut microbiota, these bacteria will negatively impact the drug efficiency.

The present invention also relates to a probiotic bacterial strain selected from the group consisting of *Lactobacillus johnsonii*, *Enterococcus hirae* and *Enterococcus faecalis*, for use in combination with an antineoplastic agent for inducing a T-bet/Th1 local and systemic immune response, for treating a cancer.

Examples of probiotics according to the present invention are the *Lactobacillus johnsonii* strain LJFS001B, deposited on Nov. 15, 2013 at the Collection Nationale de Cultures de Microorganismes (CNCM), under the number I-4823, and the *Enterococcus hirae* strain EHFS001, deposited on Nov. 7, 2013 at the Collection Nationale de Cultures de Microorganismes (CNCM), under the number I-4815.

According to a preferred embodiment, the probiotic bacterial strain according to the invention is formulated for oral administration. The skilled artisan knows a variety of formulas which can encompass living or killed microorganisms and which can present as food supplements (e.g., pills, tablets and the like) or as functional food such as drinks, fermented yoghurts, etc.

The present invention still relates to the use of such probiotics, in combination with an antineoplastic treatment, for treating a cancer patient.

As used herein, the term "in combination" refers to the use of more than one agents (e.g., a probiotic strain and a chemotherapeutic drug). The use of the term "in combination" does not restrict the order in which therapies are administered to the patient, although it is preferable to administer the probiotic strain prior to or simultaneously with the antineoplastic treatment. For example, the probiotic strain can be administered prior to the antineoplastic agent (e.g., 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), either punctually or several times (for example, each day) before the antineoplastic treatment is administered.

According to a preferred embodiment, the probiotic bacterial strain according to the invention is used in combination with a chemotherapeutic agent or an biological immunotherapy, for example in combination with a treatment by an alkylating agent or by immunotherapy.

A composition comprising at least the *Lactobacillus johnsonii* strain LJFS001B, (FIG. 26A) deposited on Nov. 15, 2013 at the Collection Nationale de Cultures de Microorganismes (CNCM), under the number I-4823, and/or the *Enterococcus hirae* strain EHFS001 (FIG. 26B), deposited on Nov. 7, 2013 at the Collection Nationale de Cultures de Microorganismes (CNCM), under the number I-4815, is also part of the present invention. The compositions according to the invention can be in the form of food supplements (e.g., pills, tablets, syrups and the like) or in the form of functional food such as drinks, fermented yoghurts, etc. The probiotics are preferentially alive in these compositions.

According to another aspect, the present invention relates to adoptive cell transfer of "pathogenic" Th17 (pTh17) cells derived from CD4+ T cells from a cancer patient, preferentially in combination with an antineoplastic treatment such as a chemotherapy (e.g., with an alkylating agent) or an immunotherapy (e.g., antitumor vaccine, . . . ), for treating said patient. For example, CD4+ naive T cells can be obtained from blood, then amplified and stimulated ex vivo in the presence of cytokines favouring the pTh17 phenotype (for example in the presence of IL-1β, IL-6, IL-21 and IL-23 and optionally IL-1b+IL-9) as well as TCR cross-linking (such as beads coated with anti-CD3/anti-CD28 Ab). As described above, pTh17 cells share hallmarks of Th1 cells (nuclear expression of the transcription factor T-bet, cytoplasmic expression of IFNγ and surface exposure of the chemokine receptor CXCR3) and Th17 cells (expression of RORγt, IL-17 and CCR6). The phenotype of the cells is controlled before their transfer to the patient. If necessary, cells obtained ex vivo are sorted to retain only those exhibiting the pTh17 phenotype.

Other characteristics of the invention will also become apparent in the course of the description which follows of the biological assays which have been performed in the framework of the invention and which provide it with the required experimental support, without limiting its scope.

EXAMPLES

Example 1: The Intestinal Microbiota Modulates the Anticancer Immune Effects of Cyclophosphamide—Mouse Study Materials and Methods N.b.: absent contrary indication, the materials and method which are described in the present example are those which have also been used in the other examples.

Animals and Tumor Models.

All animal experiments were carried out in compliance with French and European laws and regulations. Mice were used between 7 and 14 weeks of age. WT SPF C57BL/6J and DBA2/J mice were obtained from Harlan, Charles River or Janvier and kept in specific pathogen-free conditions (SPF). Nod1$^{-/-}$Nod2$^{-/-}$ and Nod2$^{-/-}$ C57BL/6J mice were provided by I. Gomperts Boneca (Institut Pasteur, France), Myd88$^{-/-}$ C57BL/6J mice by B. Ryffel (CNRS, France) and C57BL/6J germ-free mice were obtained from CDTA (Orléans, France) or Institut Pasteur and maintained in sterile isolators. MCA205, B16F10 (syngeneic from C57BL/6J mice) and P815 (syngeneic from DBA2/J mice) were cultured at 37° C. under 5% $CO_2$ in RPMI 1640 containing 10% FCS, 2 mM L-glutamine, 100 IU/ml penicillin/streptomycin, 1 mM sodium pyruvate and MEM non-essential amino acids (Invitrogen). $0.5-1 \times 10^6$ MCA205, $0.3 \times 10^6$ B16F10 or $0.8 \times 10^6$ P815 tumor cells were inoculated s.c. in the right flank. Chemotherapy was performed by intratumoral injection of doxorubicin (Doxo) (2 mM, 50 or intraperitoneal inoculation of CTX (100 mg/kg of body weight) when tumors reached 35-60 $mm^2$.

Treatment of Lung Adenocarcinoma-Bearing KP Mice Using Chemotherapy.

Eight week-old KrasLSL-G12D/WT; $p53^{Flox/Flox}$ mice received an adenovirus expressing Cre recombinase by intranasal instillation (defined as d0). The Cre recombinase system activates oncogenic Kras (KrasG12D) and deactivates p53 in a few somatic cells of the lung; grade 3 and 4 adenocarcinomas become visible at ~d70 (Cortez-Retamozo et al., 2013). Mice were either left untreated or received chemotherapy (d84, d91 and d98) in absence or presence of 0.25 mg/ml vancomycin (mixed into drinking water starting on d77 and until the end of the experiment; antibiotic-containing water was replaced biweekly). Tumor volumes were quantified on d73 and 100 (equivalent of 'pre' and 'post' chemotherapy) in anesthetized mice by noninvasive imaging as described before (Cortez-Retamozo et al., 2013). Data show absolute changes in total lung tumor volumes (means±SEM) between the two time points.

Reagents.

Cyclophosphamide (CTX) (Endoxan, Baxter) was provided by Institut Gustave Roussy. Doxorubicin hydrochloride (D1515) and Fluorescein isothiocyanate-dextran (FITC-dextran) (46944, 4 kDa) were obtained from Sigma-Aldrich. Anti-mouse antibodies for CD3ε, CXCR3 (CXCR3-173), CD4 (GK1.5), CD8α (53-6.7), γδ TCR (GL-3), IL-17 (eBio17B7), IFNγ (XMG1.2), T-bet (4B10), RORγt (AFKJS-9), CD45, CCR6 (140706) were obtained from BioLegend, eBioscience and R&D. LIVE/DEAD fixable yellow stain fluorescence for viability staining was purchased from Invitrogen/Molecular Probes. All cells were analyzed on a Cyan (Beckman Coulter) or a FACSCANTO II (BD) flow cytometer with FloJo (Tree Star) software.

Antibiotics Protocols.

Mice were treated with antibiotics 2-3 weeks before tumor implantation and continued until the end of the experiment. A mix of ampicillin (1 mg/ml)+streptomycin (5 mg/ml)+colistin (1 mg/ml) (Sigma-Aldrich) or vancomycin (0.25 mg/ml) or colistin alone ($2 \cdot 10^3$ U/ml) were added in sterile drinking water. Solutions and bottles were changed 2-3 times a week. Antibiotic activity was analyzed by macroscopic changes observed at the level of caecum (dilatation) and by cultivating the fecal pellets resuspended in BHI+15% glycerol on blood agar and anaerobic blood agar plates for 48 h at 37° C. with 5% $CO_2$ for aerobic conditions or in anaerobic conditions respectively. In experiments shown in FIG. 4, vancomycin biased the repertoire of commensal bacteria towards distinct commensal species (such as E. coli and different species of Clostridium, FIG. 16) whereas colistin promoted the outgrowth of E. faecalis.

Bacterial Isolation, Cultivation and Identification.

Mesenteric lymph nodes and spleens were aseptically removed, smashed in PBS and plated onto COS agar plates (BioMérieux), for aerobic and anaerobic growth. After 48 h of culture, single colonies were isolated and stocked in glycerol at −80° C.

Serial dilutions of feces from naïve mice or tumor bearers treated with NaCl or CTX, vancomycin or broad spectrum antibiotics (ATB) (ampicillin+streptomycin+colistin), were plated onto COS agar plates and after 48 h, single colonies were isolated and Gram staining was performed. The identification of specific bacteria was accomplished through the combination of morphological tests and the analysis through VITEK® automated system (BioMérieux, France) and verified in mass spectrometry (MALDI-TOF, see below) performed at Pasteur Institute, Paris, France.

P. distasonis used in the experiments was isolated from feces of SPF mice treated with prolonged broad spectrum ATB and identified as described above. For in vitro experiments, E. hirae, E. faecalis and E. coli were grown in BHI medium (Fluka analytical), while L. johnsonii, L. plantarum and L. murinus in MRS broth (BD) at 37° C. until they reach an $OD_{600}=1$ when the growth was exponential. L. reuteri was grown in anaerobic conditions onto COS agar plates for 48 h at 37° C. Serial dilutions of bacteria preparations were plated so that the administered doses could be assessed. E. coli MC1061, E. faecalis JH2-2 and L. plantarum NCIMB8826 were kindly provided by I. Gomperts Boneca, Institut Pasteur, France. P. distasonis was grown onto COS agar plates in anaerobic conditions for 48 h, then colonies were resuspended in PBS to reach an $OD_{600}=1$.

The identification of bacteria was done by MALDI-TOF analysis and 16S rRNA gene sequencing. The MALDI-TOF MS analysis was done on prepared cells as follows. Strains were grown overnight at 37° C. on MRS agar. About 5 to 10 mg of cells were resuspended in 300 μl of sterile ultrapure water and 900 μl of absolute ethanol, homogenized by flicking the tubes, centrifuged for 2 min at 13000 g and the supernatant was discarded. Subsequently, 50 μl of formic acid was added to the pellet and mixed before the addition of 50 μl acetonitrile. The mixture was centrifuged again at 13000 g for 2 min. One microliter of the supernatant was spotted on the MALDI-TOF sample plate and air-dried at room temperature. Each sample was covered with 1 μl of (HCCA) matrix solution (Bruker Daltonics ref 201344: saturated solution of α-cyano-4-hydroxycinnamic acid in 50% acetonitrile-2.5% trifluoroacetic acid) and air dried at room temperature. Measurements were performed with an Autoflex mass spectrometer (Bruker Daltonik GmbH, Germany) using flexcontrol software (version 3.0). Spectra were recorded in the positive linear mode (laser frequency, 200 Hz, ion source I, voltage at 20 kV; ion source 2, voltage at 18.4 kV; lens voltage, 9.1 kV; mass range, 2000-20 000 Da). For automated data analysis, raw spectra were processed using the MALDI BioTyper 2.0 software (Bruker Daltonik GmbH, Germany) with default settings. The 16S rRNA gene from the strains studied was amplified by PCR using the universal primers A, 5'-AGAGTTTGATCATGGCTCAG-3' (SEQ ID No: 1) (position 8 to 27, Escherichia coli numbering) and H, 5'-AAGGAGGTGATCCAACCGCA-3' (SEQ ID No: 2) (position 1541 to 1522) (Bottger, 1989), in a GeneAmp® thermal cycler (Perkin-Elmer, Wellesley, Mass.) and the following parameters: 4 min at 94° C., 25 cycles of 1 min at 94° C., 25 of 1 min at 57° C., 25 of 2 min at 72° C. with a final extension step at 72° C. for 5 min. Sequencing of PCR-generated amplicons was performed by GATC Company using primers A, H, and two other sequencing primers (E. coli numbering system): B, 5'-CTCCTACGGGAGGCAGCAGT-3' (SEQ ID No: 3), position 339 to 358; and G, 5'-GCATGTGGTTTAATTCGA-3' (SEQ ID No: 4), position 947 to 964. The almost-complete sequences of the gene coding for 16S rRNA were obtained after assembling using software BioNumerics version 6.6 (Applied-Maths, Belgium) and then blasted in NCBI BLAST program.

Histology and Immunofluorescence of Gut Tissue.

The whole small intestine (duodenum, jejunum and ileum) was removed, cleaned from fecal content and fixed in 4% of PFA for 1 h. Re-hydration of the tissue was performed in 15% sucrose for 1 h and in 30% sucrose overnight. Depending on the experiment, the small intestine was entirely rolled, or cut into small pieces, then embedded in optimum cutting temperature (OCT) compound (Sakura), snap frozen and longitudinal or transversal 6 sections were prepared.

For histological analyses, the longitudinal sections were counterstained with hematoxilin and eosin. For the histological quantitative analyses, inflammatory foci, altered villi and the thickness of lamina propria were scored for each section, while the number of goblet cells was counted for each villus. For Paneth cells enumeration, the longitudinal sections were permeabilized with 0.5% triton for 15 min, and were blocked with a solution of 0.1% triton, 5% serum and 1% BSA for 1 h. Then, a rabbit polyclonal antibody against the lysozyme protein (1:500 for 1 h, Thermo Scientific) and ALEXA FLUOR 488 Fragment of goat anti-rabbit IgG (1:300 for 1 h, Molecular Probes) were used. All steps were performed at room temperature. Lysozyme-positive areas were quantified on mosaic images using the Histolab software (Microvision Instruments). The quantification of Paneth cells was performed measuring the average area of the Lysozyme-positive clusters (group of Paneth cells) as well as the emission/$\mu m^2$ of those clusters (not shown).

Immunofluorescence Stainings of the Gut Leukocytes.

For the γδ TCR+ and γδ TCR− T cell quantification, transversal sections were blocked with a solution of 0.1% TRITON and 10% goat normal serum for 1 h. Then, the sections were immunostained with hamster anti-γδ TCR (10 µg/ml O/N 4° C., BD Pharmingen) and with goat anti-hamster A488 (7.5 µg/ml for 45 min, Jackson ImmunoResearch) as secondary antibody, or with hamster anti-mouse CD3 A647 (5 µg/mlfor 2 h, Biolegend). For each section, the number of total cells, γδ TCR$^+$ CD3$^+$ and CD3$^+$ cells were counted to determine the percentage of γδ TCR$^+$ and γδ TCR$^-$ T cells.

In Vivo Intestinal Permeability Assay.

Gut barrier integrity was assessed by permeability to FITC-dextran (4 kDa, Sigma Aldrich). Fourteen hours after i.p. injection with NaCl or CTX at 100 or 200 mg/kg, mice were fasted for 4 hours and then orally fed with FITC-dextran at 0.6 mg/g body weight (80 mg/ml in NaCl, 18 h after NaCl/CTX treatment). After 3 to 4 h, the mice were euthanized and exsanguinated by cardiac puncture. Plasma FITC levels were subsequently determined using a fluorescence spectrophotometer ($\lambda_{ex}/\lambda_{em}$=485/535 nm).

Isolation of Lamina Propria Cells from Small Intestine.

Whole duodenum and ileum were harvested, Peyer's patches were removed, as well as all fat residues and fecal content. Small fragments were obtained by cutting them first longitudinally along the length and then transversally into pieces of 1-2 cm length. After removing the intra-epithelial lymphocytes (IELs), the gut pieces were further cut and incubated with 0.25 mg/ml collagenase VIII and 10 U/ml DNase I for 40 min at 37° C. under shaking to isolate lamina propria cells (LPCs). After digestion, intestinal pieces were mashed on a cell strainer. For FACS analysis, cell suspensions were subjected to a percoll gradient for 20 min at 2100 RPM, while for RNA extraction, cells were directly lysed in RLT buffer (Qiagen) and frozen at −80° C.

Analyses of Dendritic Cell Subsets in CTX-Treated Small Intestines.

Cell suspensions from mouse spleen and lymph nodes were prepared by digestion with collagenase and DNase for 60 min and subsequently strained through a 70 µm mesh. Colonic and small intestinal lymphocytes were isolated as previously described (Schlitzer et al., 2013). In brief colon and small intestine were digested in PBS containing 5 mM EDTA and 2 mM DTT shaking at 37° C. After initial digestion colonic and small intestinal tissue pieces were digested in collagenase/Dnase containing RPMI medium for 30 min. Tissue pieces were further strained through a 70 µm mesh. For flow cytometry analyses, cell suspensions were stained with antibodies against the following surface markers: CD11c (N418), CD11b (M1/70), Lytic (HK1.4), MHC class II (M5/114.15.2), CD24 (M1/69), CD64 (X54-5/7.1), CD317 (ebio927), CD45 (30-F11), F4/80 (C1:A3-1), CD8α (53-6.7). DAPI was used for dead cell exclusion. Antibodies were purchased from eBiosciences, BD Biosciences or BioLegend respectively. Cell populations were gated as follows: small intestine (migratory fraction): CD103$^+$ DC (CD45$^+$ CD11c MHC-II$^+$ CD103$^+$ CD24$^+$), CD11b$^+$ CD103$^+$ (CD45$^+$ CD11c MHC-II$^+$ CD103$^+$ CD11b$^+$ CD24$^+$), CD11b$^+$ (CD45$^+$ CD11c$^+$ MHC-II$^+$ CD11b$^+$ CD24$^+$), inflammatory DC (CD45$^+$ CD11c$^+$ MHC-II$^+$ CD11b$^+$ CD64$^+$ Ly6c$^+$), large intestine: CD103$^+$ DC (CD45$^+$ CD11c$^+$ MHC-II$^+$ CD103$^+$ CD24$^+$), CD11b$^+$ (CD45$^+$ CD11c MHC-II$^+$ CD11b$^+$ CD24$^+$), inflammatory DC (CD45$^+$ CD11c$^+$ MHC-II$^+$ CD11b$^+$ CD64$^+$ Ly6c$^+$).

Microbiota Reconstitution.

For inoculation of GF mice with SFB, fecal pellets were collected from SFB-monocolonized mice with sterilized test tubes. Colonization was performed by oral gavage with 200 µl of suspension obtained by homogenizing the fecal pellets in water. Efficient colonization was first checked before tumor inoculation.

E. hirae, L. johnsonii and L. plantarum were grown in BHI (Fluka analytical) and MRS (BD) broth, respectively, overnight at 37° C. Bacteria were centrifuged, washed once and resuspended in sterile PBS at an OD(600 nm) of 1, which corresponds approximately to $1 \times 10^9$ colony-forming units (CFU)/ml. Equal volume of each bacteria suspension was mixed to give a suspension of equal proportion of each type of bacteria at $1 \times 10^9$ bacteria/ml. L. reuteri was grown in anaerobic conditions onto COS agar plates for 48 h at 37° C. For P. distasonis colonization, mice were treated with a mix of ampicillin/streptomycin/colistin (ATB) for 4 weeks and orally inoculated with $10^9$ CFU in 200 µl of PBS 4 days post MCA205 inoculation. For other experiments, after 2-3 weeks of ATB, the treatment was stopped and mice were orally gavaged with $10^9$ CFU of E. hirae+L. johnsonii or L. plantarum or L. reuteri one day after CTX administration and 0 to 3 days post treatment suspension.

TCR and T Cell Assays.

For cross-linking experiment, $2 \times 10^5$ total splenocytes per well (after red cell lysis) were incubated in MaxiSorp plates (Nunc) precoated with anti-CD3ε mAb (145-2C11) (0.5 µg per well; eBioscience) and/or anti-CD28 mAb (37.51) (2 µg/ml; BD). The supernatants were assayed at 48 h by ELISA for mouse IL-17A (eBioscience) and IFNγ (BD). For TIL analyses, tumors were removed, cut into small pieces and digested in Liberase™ (Roche) and DNase I for 30 min at 37° C. Single-cell suspensions were obtained by crushing the digested tissue with a syringe plunger and filtering through a 100 µM cell strainer. For intracellular, cells were incubated for 4 h at 37° C. with 50 ng/ml of PMA, 1 µg/ml of ionomycin and BD Golgi STOP™. After membrane staining, cells were stained with anti-IL-17A, IFNγ, T-bet and RORγt using eBioscience FoxP3/Transcription factor staining buffer set.

T Cell Polarization and Propagation In Vitro.

Adoptive Transfer of Th17 Cells (Pathogenic or Regulatory Th17). Naive CD4+ T cells (CD4+CD62L$^{hi}$) were obtained from spleens and lymph nodes of C57BL/6 WT mice. Cells were then sorted by flow cytometry (BD ARIA III with FACSDiva Software) accordingly. The purity of isolated T cell populations routinely exceeded 95%. Naive T cells were stimulated with plate-bound antibodies against CDR (145-2C11, 2 µg/ml) and CD28 (PV-1, 2 µg/ml) in the presence of either recombinant mouse IL-1β (10 ng/ml), IL-6 (10 ng/ml), and IL-23 (20 ng/ml) (pTh17) or TGF-β (2.5 ng/ml) and IL-6 (Th17) (Miltenyi). Regulatory Th17 (Th17) resulted from a differentiation in TGF-β (2.5 ng/ml) and IL-6 while pathogenic Th17 (pTh17) resulted from incubation in IL-43, IL-6 and IL-23. Mice were intravenously injected with 3×10$^6$ T cells. Priming of T cells in vitro. Bone marrow-derived dendritic cells (BMDCs) were generated from femurs and tibiae of C57BL/6 mice, cultured for 8 days in Iscove's medium (Sigma-Aldrich) with J558 supernatant (containing 40 ng/ml of GM-CSF), 10% FCS, 100 IU/ml penicillin/streptomycin, 2 mM L-glutamin, 50 µM 2-mercaptoethanol (Sigma-Aldrich) and split every 3-4 days. At day 8, BMDCs were infected with the isolated bacterial strains at a MOI (multiplicity of infection) 1:50 for 1 h at 37° C. in the appropriate medium without antibiotics. Then, cells were washed with PBS and incubated in complete medium supplemented with gentamicin (50 mg/ml) to kill extracellular bacteria. After 24 h, BMDCs were cultured together with naive CD4+ CD62L+ T cells, purified from spleen and lymph nodes (Miltenyi), at the ratio 1:1 for 4 days. Culture supernatants were then assayed for IL-17 and IFNγ by ELISA. CD4+ T cell memory response. BMDCs were infected with different doses of bacteria (ratio cells: bacteria 1:2, 1:10 and 1:50) as described above and after 24 h were cultured 1:1 with CD4+ T cells, purified from spleens (Miltenyi) of CTX- or NaCl-treated C57BL/6 mice. After 24 h culture supernatants were assayed for IL-17 and IFNγ by ELISA.

Adoptive T Cell Transfer.

B6.CBir1 TCR transgenic (CBir1 Tg) mice (Cong et al., 2009) were generated and bred in the Animal Facility at the University of Alabama at Birmingham. All experiments were reviewed and approved by the Institutional Animal Care and Use Committee of the University of Alabama at Birmingham. CD4+ T cells were isolated from B6.CBir1 TCR Tg mice using anti-mouse CD4 magnetic beads. Briefly, splenic cells were washed twice and incubated with anti-CD4 magnetic beads at 4° C. for 30 min and then separated by magnetic field. When checked by flow cytometry, over 95% of the cells were CD4+ T cells. One million CBir1 Tg T cells (CD45.1+) were adoptively transferred i.v. into CTX or NaCl treated-naïve congenic (CD45.2+) mice two days after chemotherapy and spleens were harvested at day 5-7 post-transfer for flow cytometry analyses and ex vivo splenocyte restimulations. Flow cytometry analyses gated on CD45.1+ cells to appreciate percentages of intracellular IL-17+ or IFNg+ cells after PMA/ionomycin 5 h restimulation in the presence of monensin. Other splenocytes were incubated in triplicate in 24 well flat bottom plates at 1.0 million/ml, cultured without or with CBir1-peptide 455-475 (DMATEMVKYSNANILSQAGQ) (SEQ ID No: 34) at 1 mg/ml and supernatants were analysed using anti-IFNg specific commercial ELISA.

Quantitative RT-PCR for Antimicrobial Peptide Determination.

Lamina propria cells were isolated from duodenum, ileum and colon 18 h post CTX, and total RNA extraction and genomic DNA removal were performed with the RNeasy Mini Kit (Qiagen, Hilden, Germany), following the manufacturer's instructions. Total RNA extraction and genomic DNA removal of ilea or duodena were performed with the RNeasy Mini Kit (Qiagen, Hilden, Germany), following the manufacturer's instructions. Total RNA was then reverse transcribed into cDNA with the SuperScript III Reverse Transcriptase and the RNaseOUT™ Recombinant Ribonuclease Inhibitor (Life Technologies, Saint Aubin, France), in the presence of random primers (Promega, Charbonnieres, France) and the Deoxynucleoside Triphosphate Set, PCR grade (Roche Diagnostics, Meylan, France). Expression of RegIIIγ (Mm00441127_m1) and LysM (Mm01612741_m1)-related genes was analyzed with Taq-Man® Gene Expression Assays using the Universal Master Mix II on a StepOnePlus™ Real-Time PCR System (Life Technologies, France). Quantitative RT-PCR data were invariably normalized to the expression levels of the housekeeping gene peptidylprolyl isomerase A (Ppia) by means of the $2^{-\Delta Ct}$ method.

Microbial DNA Extraction, 454 Pyrosequencing and Quantitative PCR on Commensal Bacteria.

Total DNA was extracted from mucosal samples (~50-100 µg) as previously described (Lepage et al., 2005; Seksik et al., 2003) using both physical and chemical lysis. DNA concentration and integrity were determined both visually by electrophoresis on a 1% agarose gel containing ethidium bromide and spectrophotometrically by using a Nanodrop instrument (Thermo Scientific).

Microbiota composition was assessed by 454 pyrosequencing (GS FLX Ti technology) targeting the V3-V4 region of the bacterial 16S rRNA gene (V3fwd: 5'TACG-GRAGGCAGCAG3', SEQ ID No: 5; V4rev: 5'GGACTAC-CAGGGTATCTAAT3', SEQ ID No: 6). Sequences were trimmed for barcodes, PCR primers, and binned for a minimal sequence length of 300 pb, a minimal base quality threshold of 27, a maximum homopolymers length of 6. Resulting sequences were assigned to the different taxonomic levels, from phylum to genus using the RDP database (release 10, update 31) (Cole et al., 2009). Sequences were further clustered into OTUs (Operational Taxonomic Units or phylotypes) at 97% of identity using QIIME (Caporaso et al., 2010) and cdhit (Li and Godzik, 2006). OTUs were assigned to closest taxonomic neighbors and relative bacterial species using Seqmatch (RDP) and Blastall (NCBI). Relative abundance of each OTUs and other taxonomic levels (from phylum to genus) was calculated for each sample to account for different levels of sampling across multiple individuals. After trimming, the number of sequences clustered within each OTUs (or other taxonomic levels) was converted to a fraction representing the relative contribution of each feature to each of the individuals. For heatmaps representation, $\log_{10}$-transformation was applied on the relative abundance data matrix, which allowed visualizing similarities or differences between samples that affect members of the community that may make up less than 1% of the relative abundance in a sample. Principal component analyses of the different mice microbiota were computed based on bacterial genus composition. Robustness of each clustering result was assessed using a Monte Carlo rank test (n=10 000 repetitions, p<0.05) (Romesburg, 1985). To gain further insight into bacterial counts, quantitative PCR was applied. Targeted qPCR systems were applied using either Taqman technology (for systems targeting All Bacteria domain, *Clostridium leptum* group (Mayeur et al., 2013) or SybrGreen (for systems targeting *Lactobacillus/Leuconoctoc/Pediococcus* group (Mayeur et al., 2013), *Enterococcus* group (Furet et al., 2009), SFB (Yin et al., 2013) and TM7 (Hugenholtz et al., 2001)). No CTX-specific modulations of the relative amounts of SFB and TM7 or *Clostridium* group XIV was observed at day 7 post-CTX (not shown). Quantitative PCR was performed using an ABI 7000 SequenceDetection System with software version 1.2.3 (Applied-Biosystems). Amplification and detection were carried out with either TaqMan Universal PCR 2_MasterMix (Applied-Biosystems) or SYBR-Green PCR 2_Master Mix (Applied-Biosystems) in duplicate in a final volume of 25 µl with 10 µl of appropriate dilutions of DNA samples as previously described. Amplifications were carried out using the following ramping profile: 1 cycle at 95° C. for 10 min, followed by 40 cycles of 95° C. for 30 s, 60° C. for 1 min. For SYBR-Green amplification, a melting step was added (Yin et al., 2013). For the quantification of bacterial groups, standard curves were generated from serial dilutions of a known concentration of genomic DNA from a representative of each group. Standard curves were generated by plotting threshold cycles (Ct) vs. bacterial quantity (CFU). The total number of bacteria (CFU) was interpolated from the averaged standard curves.

Characterization of Adoptively Transferred Th17 Cells by Quantitative PCR Analysis.

Total RNA from T cells was extracted with Trizol (Invitrogen). 100 to 300 ng of RNA were reverse-transcribed into cDNA by M-MLV reverse transcriptase, Random Primers, and RNaseOUT inhibitor (Invitrogen). cDNA were quantified by real-time PCR with a SYBR Green Real-time PCR kit (Applied Biosystems) on a Fast7500 detection system (Applied Biosystems, France). Relative mRNA levels were determined with the ΔCt method. Values were expressed relative to cyclophilin A. The sequences of the oligonucleotides used are described below.

Bioinformatics and Statistics.

At the exception of proportion and count data that were respectively compared by beta regression and negative binomial regression, linear modeling was applied to evaluate the impact of treatment to the parameters in their original scale or in logarithmic scale. Systematic examination of the model residuals and application of diagnostic tools respective to each method confirmed the appropriate fit of the data. The influence of tumor and CTX treatment on the bacteria content were estimated by maximum likelihood to account for non detected measurements as previously described (Helsel, 2005). Given that non-detects could appear in both parameters, Kendall's tau (Newton and Rudel, 2007) was computed for correlation studies between IL-17/IFNγ and bacteria content with the regression line standard error bands estimated by bootstrapping (B=1999). Similar outcome was obtained by further validation studies including the application of the same procedure to the data were the samples containing non detects are excluded and the determination of the p-values by permutation. Tumor growth modeling was carried by linear mixed effect modeling on log pre-processed tumor surfaces (Demidenko, 2006; Sugar et al., 2012). Reported p-values are obtained from testing jointly that both tumor growth slopes and intercepts (on log scale) are the same between treatment groups of interests. For sake of clarity, the outcome of the test is only given for comparisons found significant at p<0.05. Post-hoc pairwise testing at single sampling time point confirmed the effects reported on the graphs. Note that no significant differences in tumor area were highlighted between treatment groups at time of treatment. "Tumor presence/absence of tumor growth" incidences were compared with Firth's penalized-likelihood logistic regression (Heinze, 2006). All reported tests are two-tailed and were considered significant: *, for a p-value<0.05, , p<0.01,*, p<0.001, ns, non significant.

Results

In the present example, the impact of CTX on the small intestine microbiota and its ensuing effects on the antitumor immune response are described.

TABLE 1 oligonucleotides used for characterizing Th17 cells expression profiles

| Gene | Forward | SEQ ID No | Reverse | SEQ ID No |
|---|---|---|---|---|
| Actin | ATGGAGGGGAATACAGCCC | 7 | TTCTTTGCAGCTCCTTCGTT | 8 |
| Cd3e | CCAGGATACTGAGGGCATGT | 9 | CTTATCAGTTGGCGTTTGGG | 10 |
| Cd4 | CCTGTGCAAGAAGCAGAGTG | 11 | GTTCTGCTGATTCCCCTTCC | 12 |
| Ppia | GGCCGATGACGAGCCC | 13 | TGTCTTTGGAACTTTGTCTGCAA | 14 |
| Eomes | CAGCACCACCTCTACGAACA | 15 | CGCCACCAAACTGAGATGAT | 16 |
| Foxp3 | CTCGTCTGAAGGCAGAGTCA | 17 | TGGCAGAGAGGTATTGAGGG | 18 |
| Gata3 | AGGATGTCCCTGCTCTCCTT | 19 | GCCTGCGGACTCTACCATAA | 20 |
|Ifng | TGAGCTCATTGAATGCTTGG | 21 | ACAGCAAGGCGAAAAAGGAT | 22 |
| Il10 | TGTCAAATTCATTCATGGCCT | 23 | ATCGATTTCTCCCCTGTGAA | 24 |
| Il17a | TGAGCTTCCCAGATCACAGA | 25 | TCCAGAAGGCCCTCAGACTA | 26 |
| Rorc | GGTGATAACCCCGTAGTGGA | 27 | CTGCAAAGAAGACCCACACC | 28 |
| Tbx21 | ATCCTGTAATGGCTTGTGGG | 29 | TCAACCAGCACCAGACAGAG | 30 |
| Tgfb | CAACCCAGGTCCTTCCTAAA | 31 | GGAGAGCCCTGGATACCAAC | 32 |

Figure 1B:
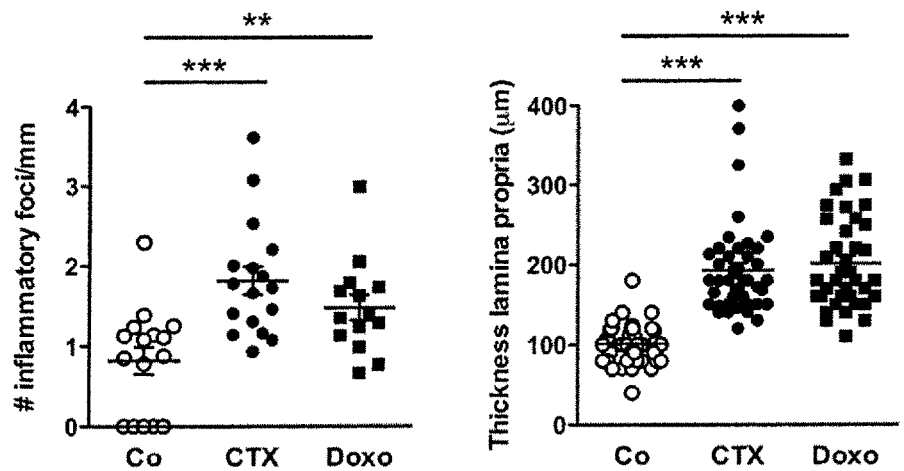
Figure 1B:
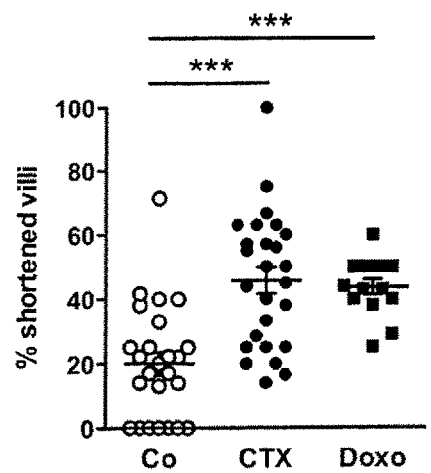
Figure 1C:
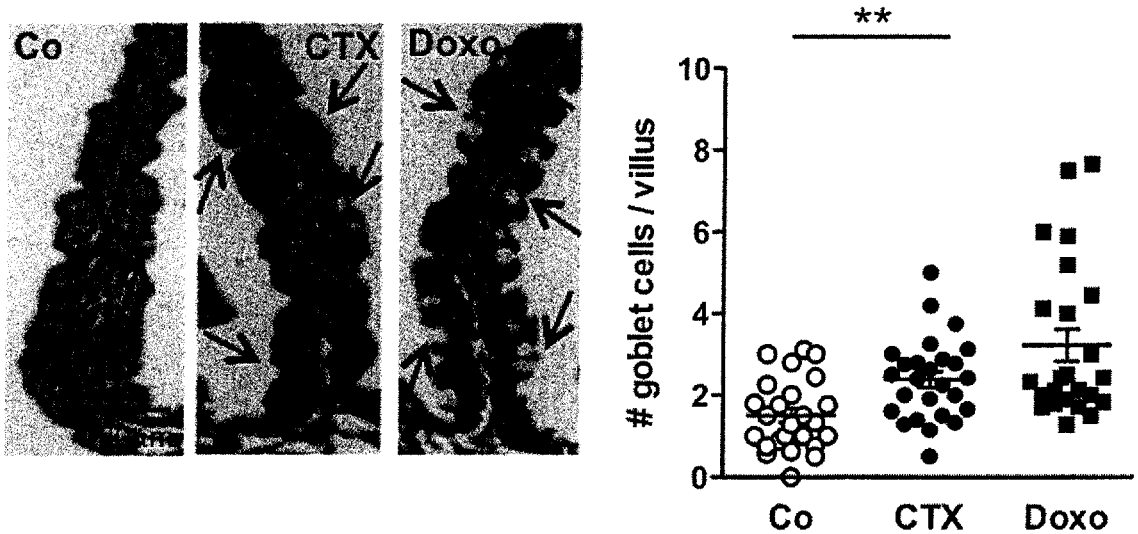
Figure 1D:
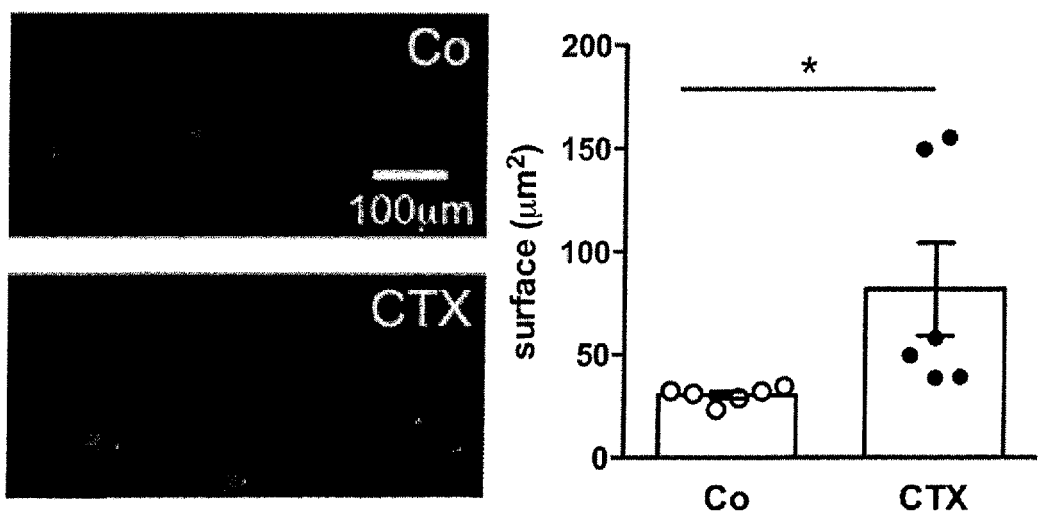
Figure 1E:
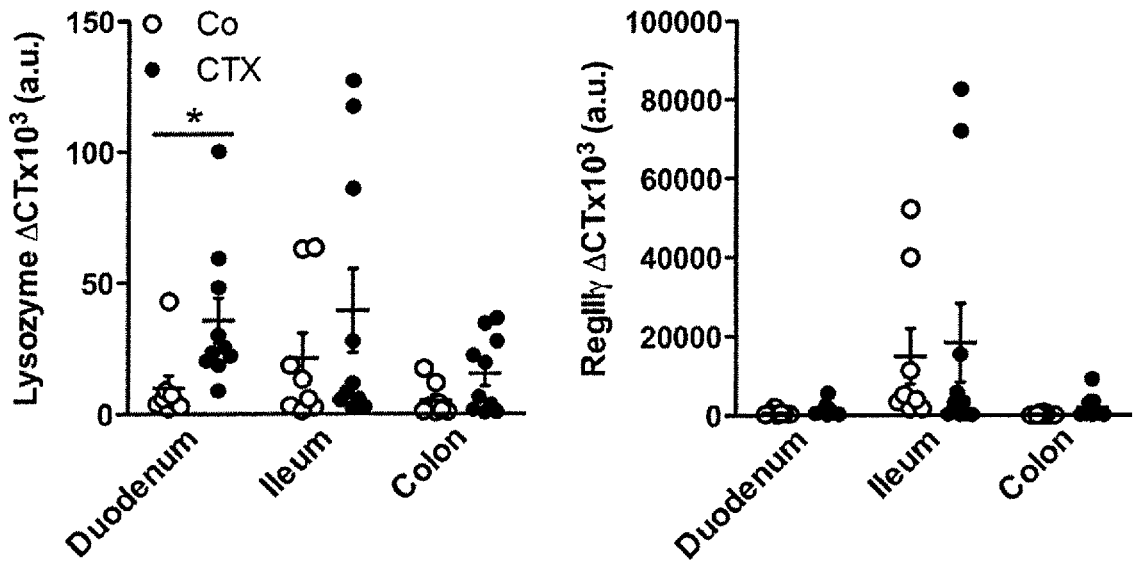
Figure 1F:
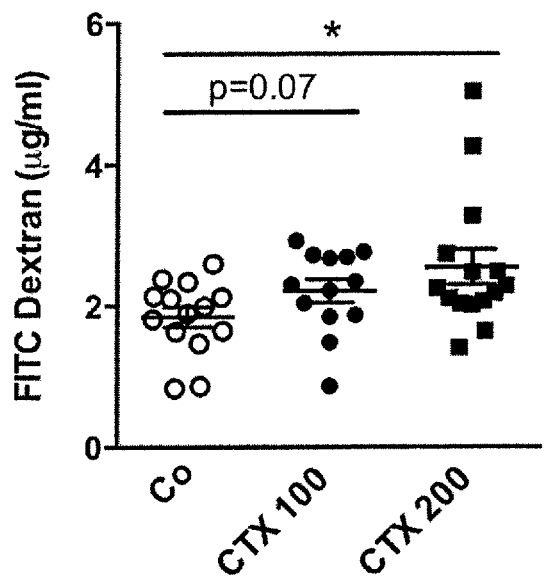

The inflammatory status of the gut epithelial barrier was characterized 48 hours following therapy with non-myeloablative doses of CTX or the anthracycline doxorubicin in naive mice. Both drugs caused shortening of small intestinal villi, discontinuities of the epithelial barrier, interstitial edema and focal accumulation of mononuclear cells in the lamina propria (LP) (FIG. 1A-B). Post-chemotherapy, the numbers of goblet cells and Paneth cells were increased in villi (FIG. 1C) and crypts (FIG. 1D), respectively. The antibacterial enzyme lysozyme (but not the microbicide peptide RegIIIγ) was upregulated in the duodenum of CTX-treated mice (FIG. 1E). Orally administered fluorescein isothiocyanate (FITC)-dextran became detectable in the blood (Yang et al., 2013) 18 h post CTX, confirming an increase in intestinal permeability (FIG. 1F). Disruption of the intestinal barrier was accompanied by a significant translocation of commensal bacteria in >50% mice into mesenteric lymph nodes and spleens that was well detectable 48 h post-CTX, less so after doxorubicin treatment (FIG. 2A). Several Gram$^+$ bacterial species, including *Lactobacillus johnsonii* (growing in >40% cases), *Lactobacillus murinus* and *Enterococcus hirae*, could be cultured from these lymphoid organs (FIG. 2B).

Figure 2C:
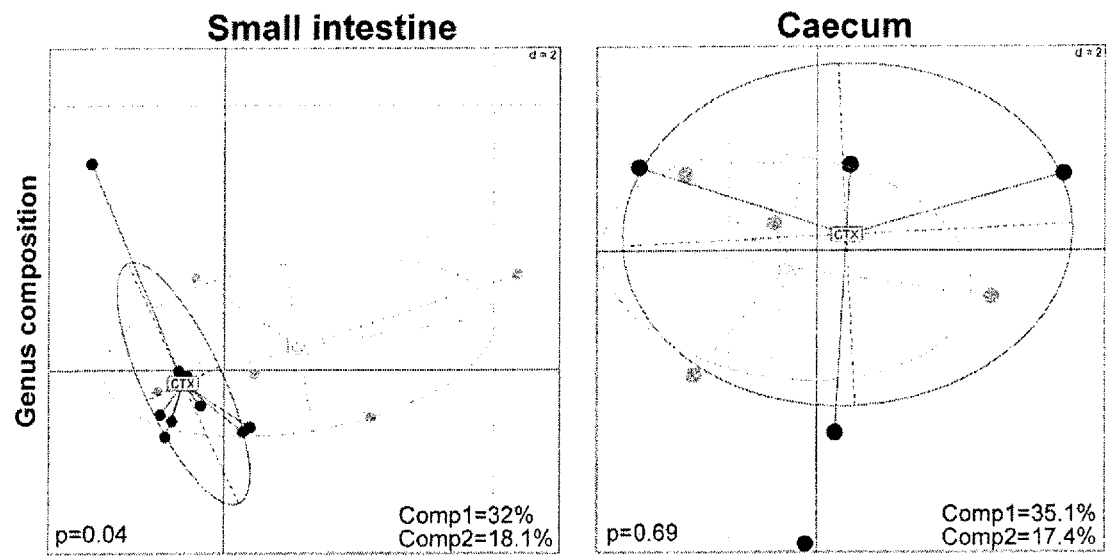

Next, the overall composition of the gut microbiota was analyzed by high-throughput 454 pyrosequencing, followed by quantitative PCR targeting the domain bacteria and specific bacterial groups. Although CTX failed to cause a major dysbiosis at early time points (24-48 h, FIG. 5), CTX significantly altered the microbial composition of the small intestine (but not of the caecum) in mice bearing subcutaneous cancers (namely metastasizing B16F10 melanomas and non-metastasizing MCA205 sarcomas) one week after its administration (FIG. 2C, FIG. 5). Consistent with previous reports on fecal samples from patients (Zwielehner et al., 2011), CTX induced a reduction of bacterial species from the Firmicutes phylum (FIG. 5) distributed within four genera and groups (*Clostridium* cluster XIVa, *Roseburia*, unclassified Lachnospiraceae, *Coprococcus*, Table 2) in the mucosa of CTX-treated animals.

and genus levels). Following phylotype (OTU) determination, phylotype centroids are assigned to their closest relative isolate (RDP Seqmatch database). All animals were compared together and tumor bearers were further distinguished. AN: NCBI Accession Number; Sab_Score: RDP similarity score between the centroid sequence and the referent isolate. Wilcoxon test p-values.

Figure 2D:
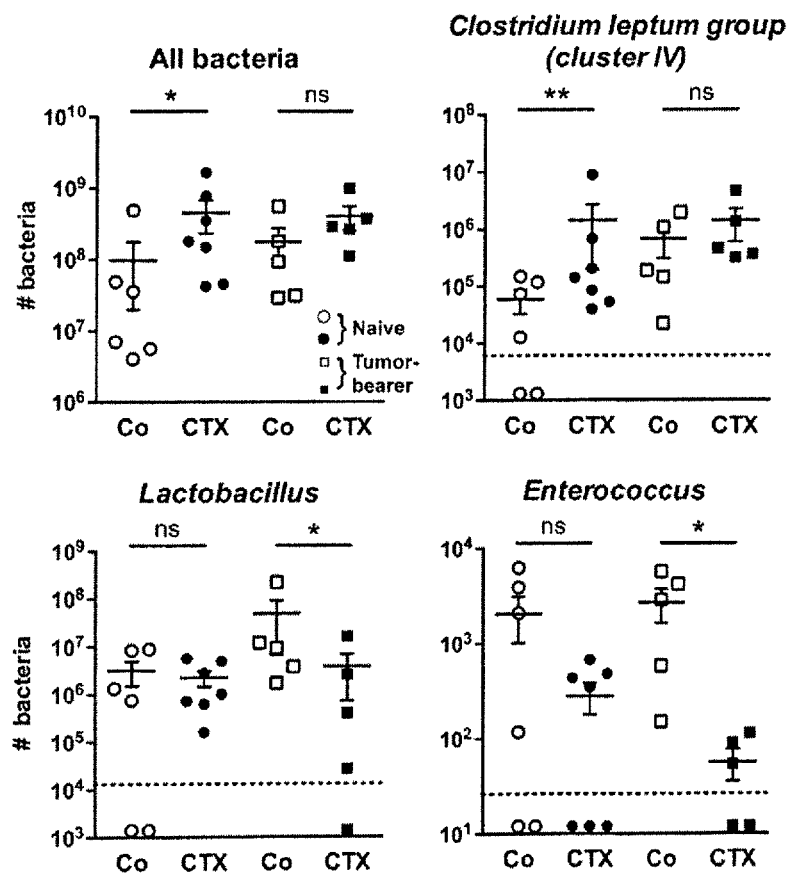

Quantitative PCR was applied to determine the bacterial counts of all bacteria and of targeted groups of bacteria (*Lactobacillus*, *Enterococcus*, *Clostridium leptum* cluster IV group) in the small intestine mucosa from CTX versus vehicle-treated naïve and tumor-bearing mice. In tumor bearers, the total bacterial load of the small intestine at 7 days post-CTX as well as the bacterial counts of the *Clostridium leptum* were not affected (FIG. 2D). However, CTX treatment led to a reduction in the abundance of lactobacilli and enterococci (FIG. 2D). Altogether, these data reveal the capacity of CTX to provoke the selective translocation of distinct Gram$^+$ bacterial species followed by significant changes in the small intestinal microbiome.

Figure 3A:
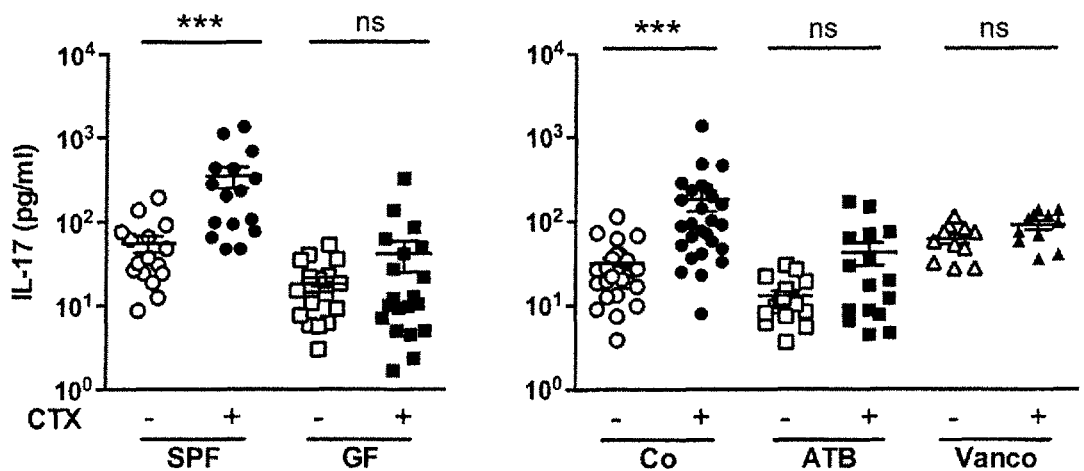
Figure 7A:
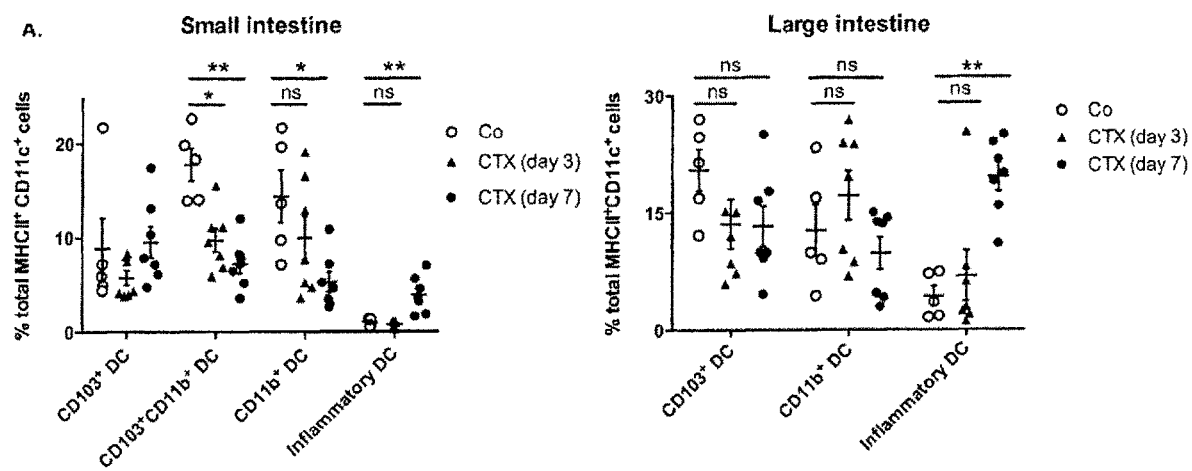
Figure 7B:
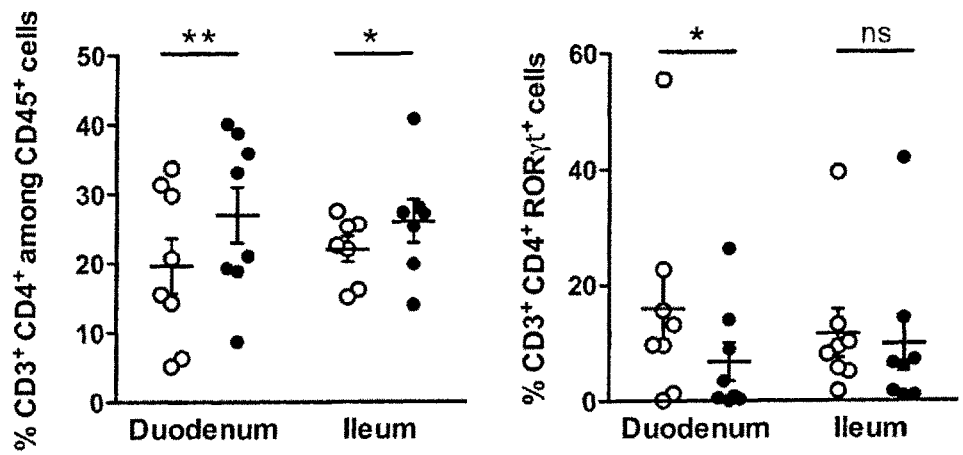
Figure 7C:
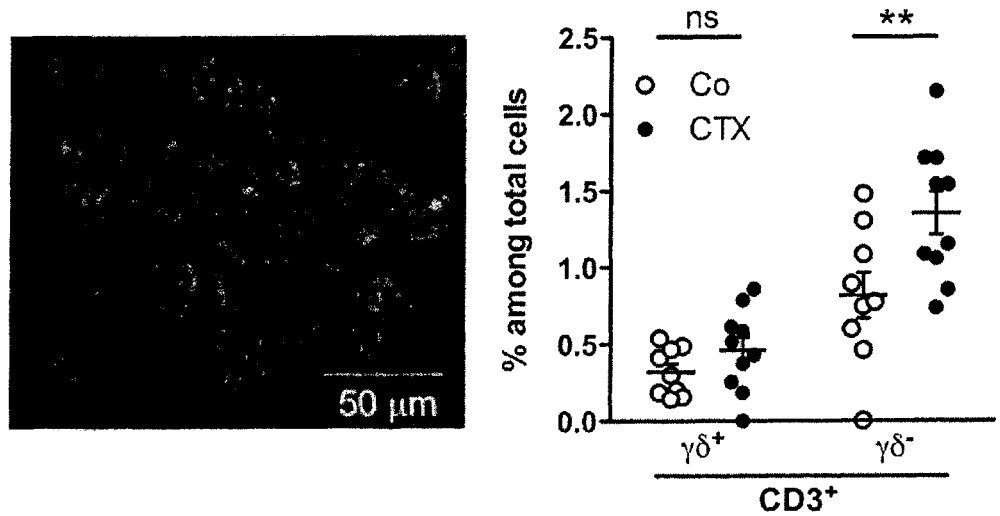
Figure 7D:
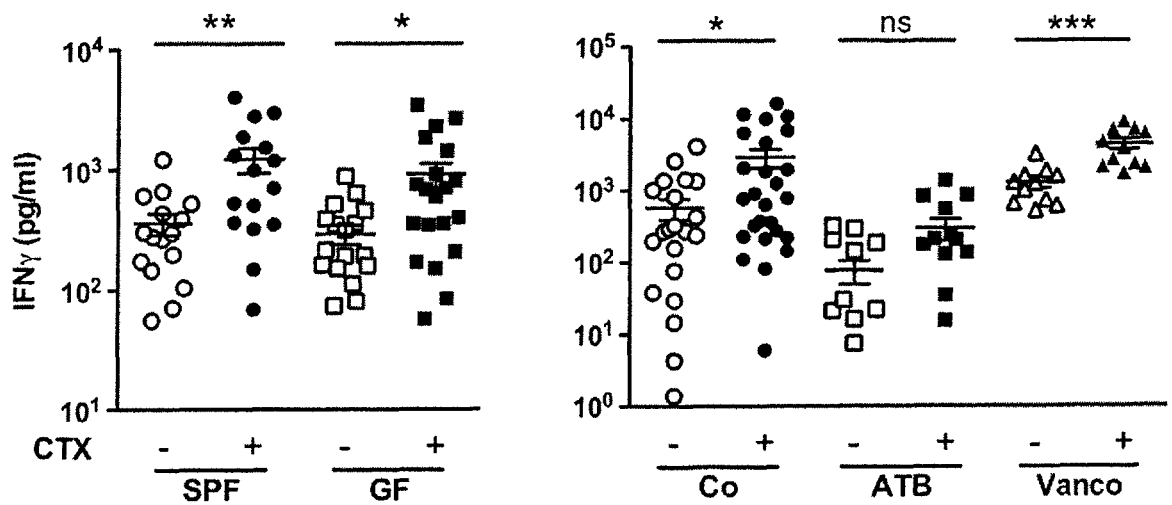
Figure 7E:
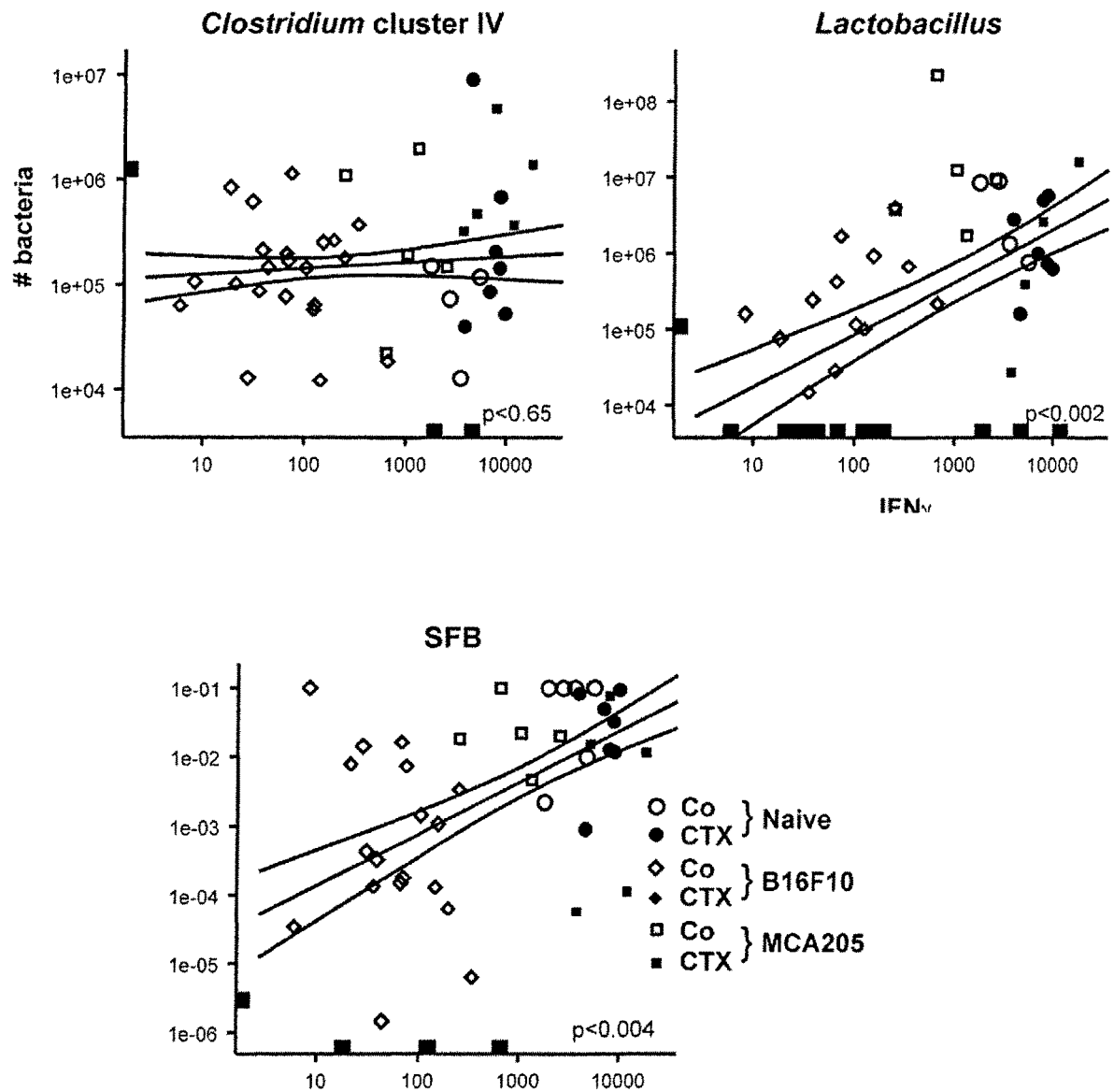

Coinciding with dysbiosis 7 days post-CTX, the frequencies of CD103$^+$CD11b$^+$ dendritic cells (FIG. 7A) and TCRαβ$^+$CD3$^+$ T cells expressing the transcription factor RORγt (FIG. 7B) were significantly decreased in the lamina propria (LP) of the small intestine (but not the colon), as revealed by flow cytometry of dissociated tissues (FIG. 7B) and in situ immunofluorescence staining (FIG. 7C). RORγt is required for the generation of Th17 cells (which produce interleukin-17, IL-17), and strong links between gut-residing and systemic Th17 responses have been established in the context of autoimmune diseases affecting joints, the brain or the pancreas (Ghiringhelli et al., 2004; Lee et al., 2011; Wu et al., 2010). Confirming previous work (Michaud et al., 2011; Viaud et al., 2011), CTX induced the polarization of splenic CD4$^+$ T cells towards a Th1 (interferon-γ [IFNγ]-producing) and Th17 pattern (FIG. 3A, FIG. 7D). This effect was not found for doxorubicin (FIG. 8). The gut microbiota was indispensable for gearing the conversion of naïve CD4$^+$ T cells into IL-17 producers in response to CTX.

TABLE 2

CTX-induced mucosal microbiota dysbiosis at a species level

| | | | | | | All Animals | | | Tumor Bearers | |
|---|---|---|---|---|---|---|---|---|---|---|
| Phylum | Genus | 1st isolate sequence name | AN | S_ab | Co | CT | pvalue | Co | CT | pvalue |
| Firmicutes | Unclassified_Clostridiaceae 1 | Segmented filamentous bacterium | X77814 | 1.000 | 0.83 | 7.95 | 0.083 | 0.58 | 2.55 | |
| Firmicutes | *Lactobacillus* | *Lactobacillus reuteri*; LU3 | AY735406 | 1.000 | 0.13 | 0.24 | | 0.02 | 0.14 | 0.048 |
| Firmicutes | *Clostridium* XIVa | Butyrate-producing bacterium SM4/1 | AY305314 | 0.908 | 1.31 | 0.21 | 0.045 | 1.76 | 0.20 | 0.049 |
| Firmicutes | *Clostridium* XIVa | Butyrate-producing bacterium M62/1 | AY305309 | 0.920 | 0.43 | 0.07 | 0.056 | 0.54 | 0.06 | 0.049 |
| Firmicutes | *Clostridium* XIVa | *Clostridium* sp. Culture-41 | AB622820 | 0.933 | 0.35 | 0.10 | 0.045 | 0.32 | 0.08 | 0.048 |
| Firmicutes | *Clostridium* XIVa | Rumen bacterium NK4A66 | GU124467 | 0.872 | 0.26 | 0.07 | 0.046 | 0.34 | 0.10 | 0.080 |
| Firmicutes | *Roseburia* | *Roseburia intestinalis*; XB6B4 | AM055815 | 0.827 | 0.24 | 0.02 | 0.032 | 0.26 | 0.00 | 0.016 |
| Firmicutes | *Roseburia* | *Roseburia faecis* (T); M7211 | AY305310 | 0.910 | 1.20 | 0.35 | | 2.00 | 0.41 | 0.095 |
| Firmicutes | Unclassified_Lachnospiraceae | *Clostridium* sp. Clone-49 | AB622849 | 0.973 | 1.04 | 0.07 | 0.056 | 1.61 | 0.09 | 0.052 |
| Firmicutes | Unclassified_Lachnospiraceae | *Clostridium* sp. A9 | DQ789119 | 0.942 | 0.70 | 0.23 | 0.045 | 0.96 | 0.27 | 0.024 |
| Firrmicutes | Unclassified_Lachnospiraceae | Lachnospiraceae bacterium 14-2 | DQ789124 | 0.859 | 0.57 | 0.05 | | 0.95 | 0.02 | 0.028 |
| Firmicutes | Unclassified_Lachnospiraceae | *Clostridium* sp. Clone-40 | AB622844 | 0.977 | 0.25 | 0.05 | | 0.42 | 0.02 | 0.026 |
| Firmicutes | Unclassified_Lachnospiraceae | Lachnospiraceae bacterium 607 | AB700365 | 0.900 | 0.06 | 0.08 | | 0.11 | 0.01 | 0.043 |
| Firmicutes | Unclassified_Lachnospiraceae | *Clostridium* sp. Culture-54 | AB622823 | 0.968 | 0.09 | 0.03 | 0.064 | 0.13 | 0.04 | 0.049 |
| Firmicutes | Unclassified_Lachnospiraceae | *Clostridium* sp ASF502 | AF157053 | 0.943 | 0.10 | 0.01 | 0.022 | 0.17 | 0.00 | 0.016 |
| Firmicutes | Unclassified_Lachnospiraceae | *Clostridium* sp. Clone-33 | AB622843 | 0.885 | 0.07 | 0.02 | 0.046 | 0.10 | 0.00 | 0.016 |
| Firmicutes | *Coprococcus* | *Coprococcus catus*; L8 | AB361624 | 0.827 | 0.13 | 0.03 | | 0.20 | 0.03 | 0.052 |
| Bacteroidetes | *Tannerella* | *Tannerella forsythia*; OB071 | JN713185 | 0.581 | 0.06 | 0.02 | | 0.10 | 0.02 | 0.028 |

Figure 3B:
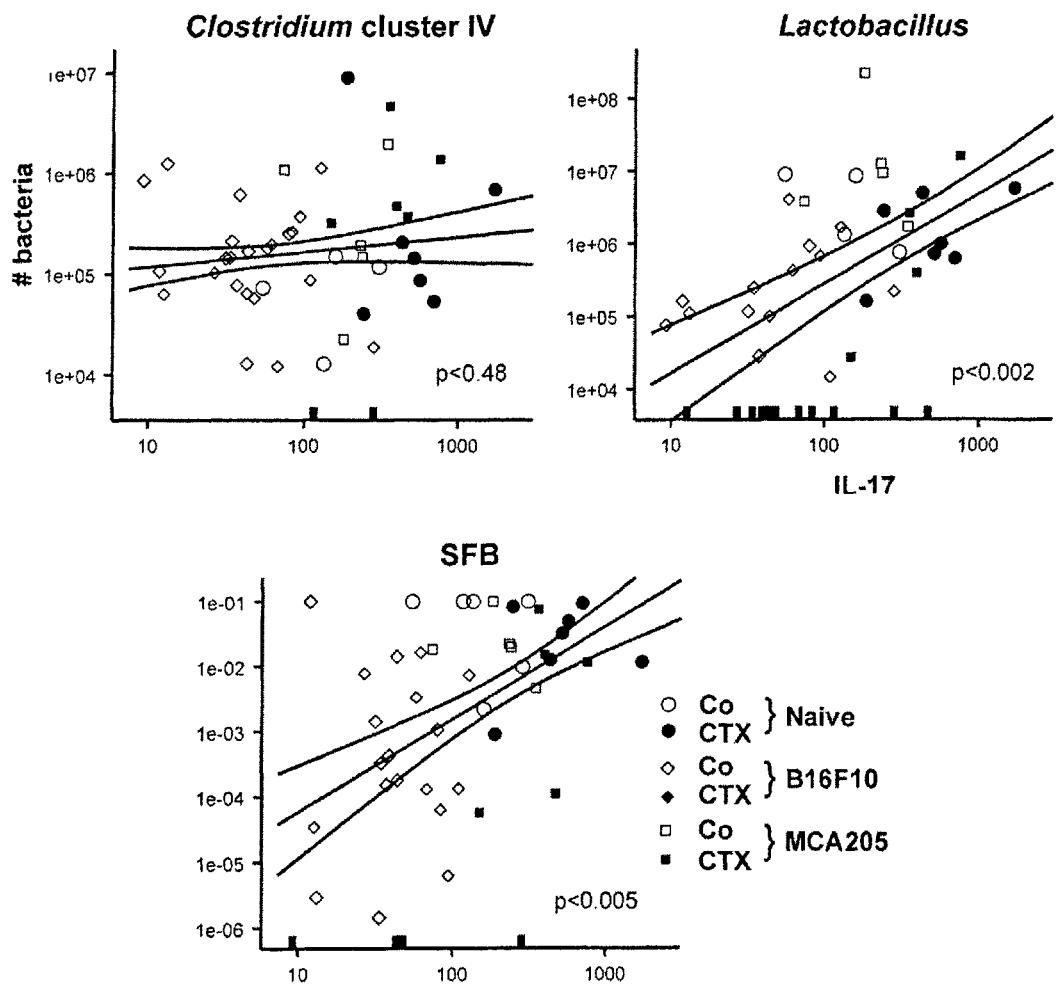

Average relative abundances of bacterial species that are significantly differentially represented between CTX treated (CTX) and NaCl-treated mice (Co) are represented. Taxonomic affiliation of these sequences is also added (phylum Indeed, the ex vivo IL-17 release by TCR-stimulated splenocytes increased upon CTX treatment of specific pathogen-free (SPF) mice, yet failed to do so in germ-free (GF) mice (FIG. 3A, left panel). Sterilization of the gut by broad-spectrum antibiotics (ATB, a combination of colistin, ampicillin and streptomycin, FIG. 9) also suppressed the CTX-stimulated secretion of IL-17 (FIG. 3A, right panel) and IFNγ by TCR-stimulated splenocytes (FIG. 7D). Treatment of mice with vancomycin, an antibiotic specific for Gram$^+$ bacteria (Rice, 2006), also reduced the CTX-induced Th17 conversion (FIG. 3A, right panel). In conventional SPF mice, the counts of lactobacilli and SFB measured in small intestine mucosa (FIG. 2D) positively correlated with the Th1 and Th17 polarization of splenocytes (FIG. 3B, FIG. 7E) whereas that of *Clostridium* cluster IV did not (FIG. 3B). Altogether, these results point to a specific association between particular microbial components present in the gut mucosa (and occasionally in lymphoid organs) and the polarity of Th responses induced by CTX treatment.

Figure 3C:
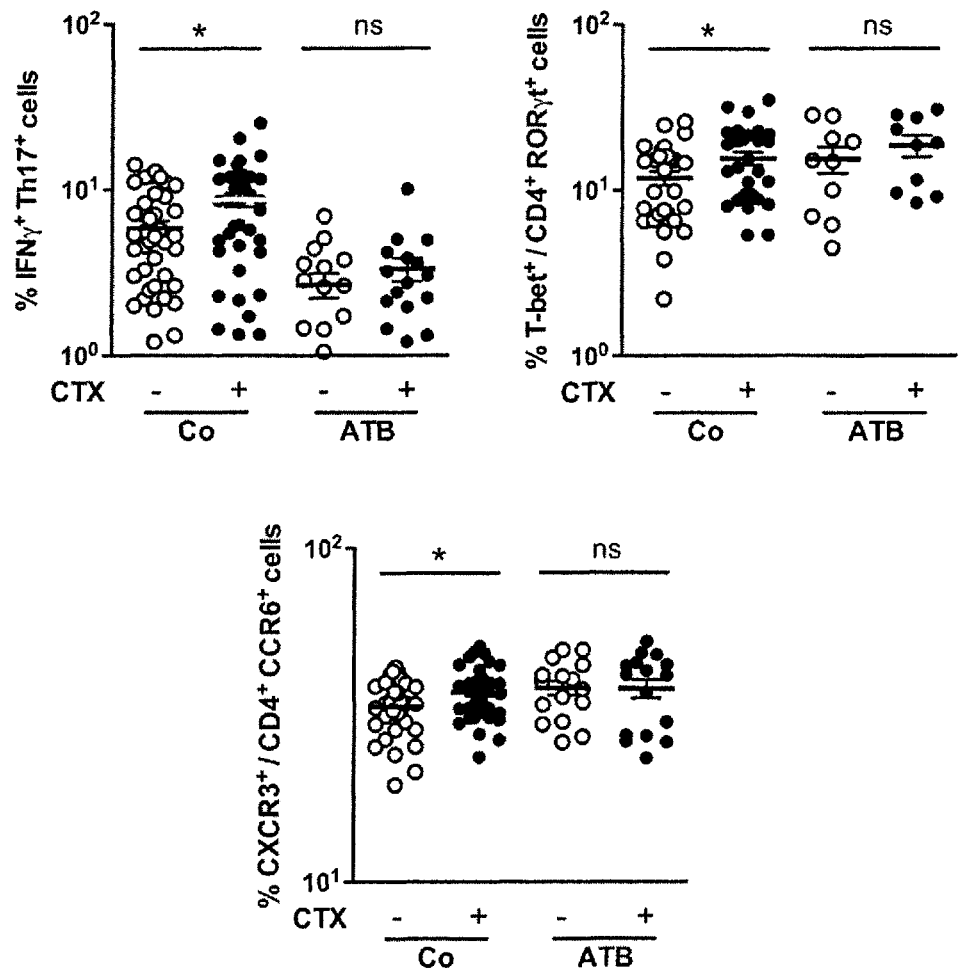
Figure 3D:
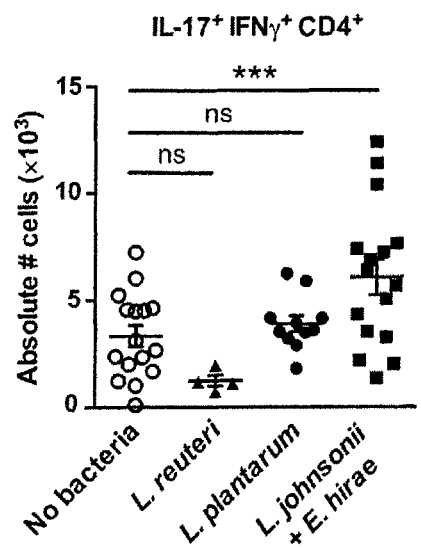
Figure 3E:
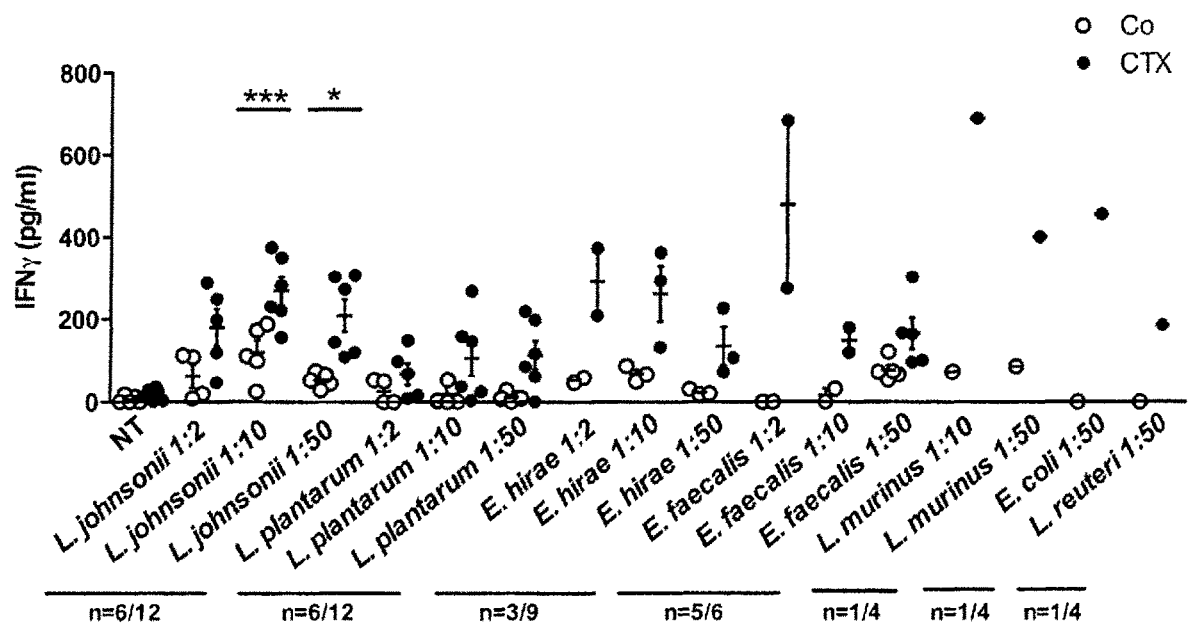
Figure 7F:
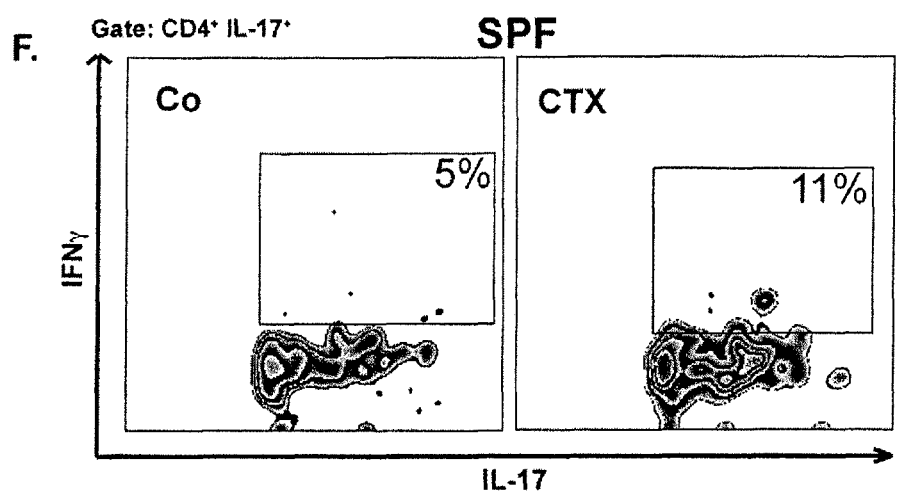
Figure 11:
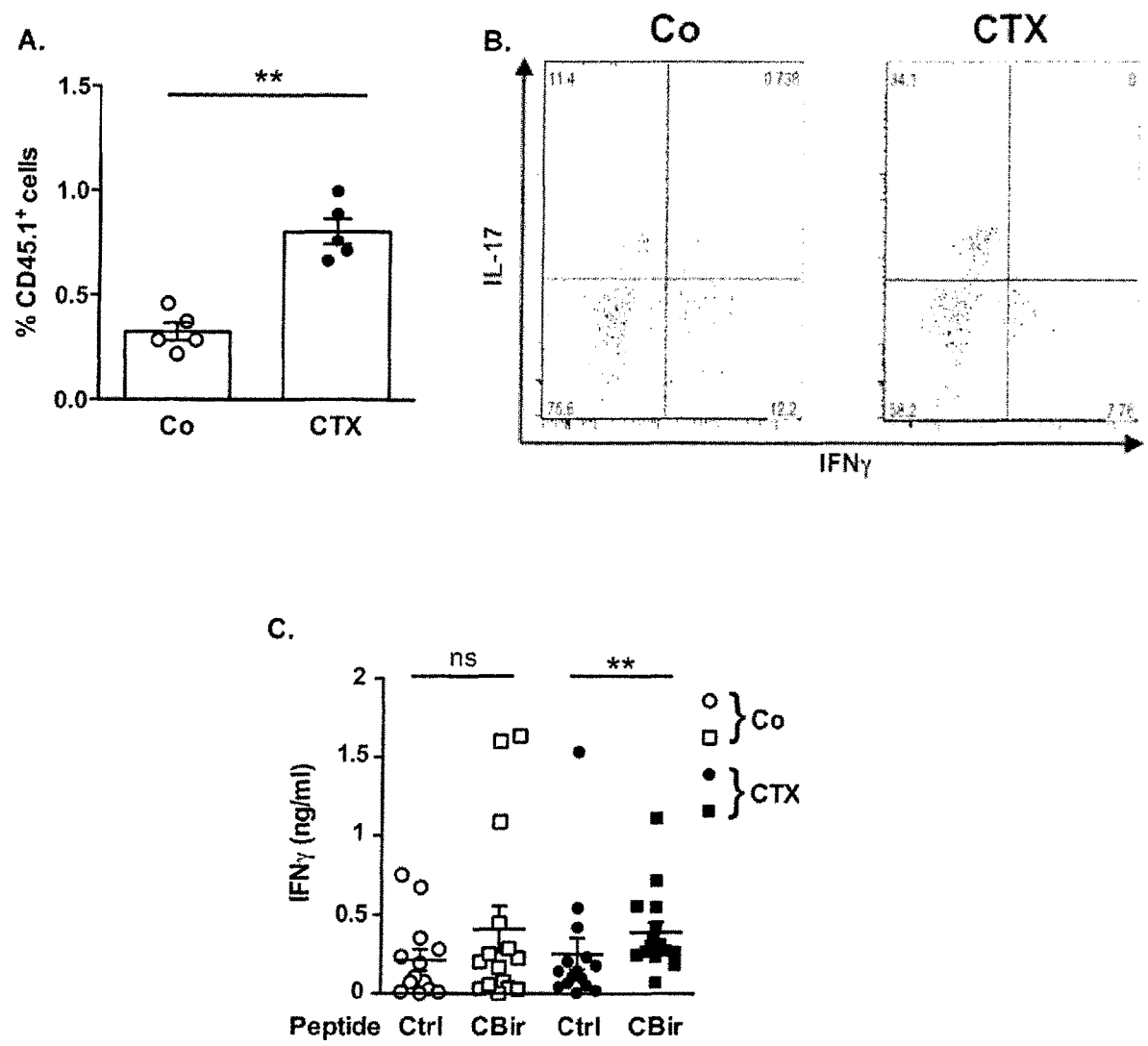

CTX increased the frequency of "pathogenic" Th17 (pTh17) cells, which share hallmarks of Th1 cells (nuclear expression of the transcription factor T-bet, cytoplasmic expression of IFNγ and surface exposure of the chemokine receptor CXCR3) and Th17 cells (expression of RORγt, IL-17 and CCR6) (Ghoreschi et al., 2010; Lee et al., 2012), within the spleen (FIG. 7F, FIG. 3C). Again, this response depended on the gut microbiota (FIG. 3C). Moreover, the increase in pTh17 cells required expression of myeloid differentiation primary response gene 88 (MyD88), which signals downstream of toll-like receptors (FIG. 10A) and is required for the therapeutic success of anticancer chemotherapies in several tumor models (Apetoh et al., 2007). In contrast, the two pattern recognition receptors, nucleotide-binding oligomerization domain-containing (Nod)1 and Nod2, were dispensable for the CTX-induced raise in splenic pTh17 cells and for the tumor growth retarding effects of CTX (FIG. 10B). These results establish the capacity of CTX to stimulate pTh17 cells through a complex circuitry that involves intestinal bacteria and MyD88, correlating with its anticancer effects. Beyond its general effect on the frequency of pTh17 cells, CTX induced TCR-restricted, antigen specific immune responses against commensal bacteria (FIG. 11). Hence, the inventors addressed whether Gram$^+$ bacterial species that translocated into secondary lymphoid organs in response to CTX (FIG. 2A) could polarize naïve CD4$^+$ T cells towards a Th1 or Th17 pattern. Both *L. johnsonii* and *E. hirae* stimulated the differentiation of naïve CD4$^+$ T cells into Th1 and Th17 cells in vitro, in the presence of bone marrow-derived dendritic cells, while toll-like receptor 4-activating purified bacterial lipopolysaccharide (LPS) or *E. coli* both had a minor effect (FIG. 12). Moreover, orally fed *L. johnsonii* and *E. hirae* but neither *L. plantarum* (a bacterium that was not detected in translocation experiments, FIG. 2B) nor *L. reuteri* facilitated the reconstitution of the pool of pTh17 cells in the spleen of ATB-treated SPF mice (FIG. 3D). Th1 memory responses against *L. johnsonii* were consistently detected in 50% of mice receiving CTX (FIG. 3E) but not in control mice, after in vitro restimulation of CD4$^+$ T cells with bone marrow-derived dendritic cells loaded with *L. johnsonii* (and to a lesser extent *E. hirae*, but not with other commensals or pathobionts). These results suggest that the translocation of a specific set of Gram$^+$ commensal bacteria can mediate the CTX-driven accumulation of pTh17 cells and Th1 bacteria-specific memory T cell responses.

Figure 4A:
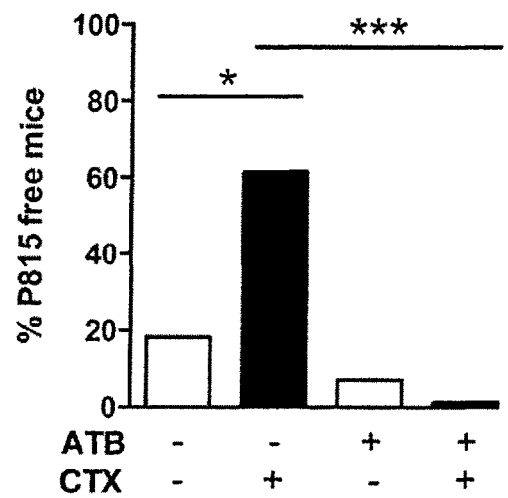
Figure 4B:
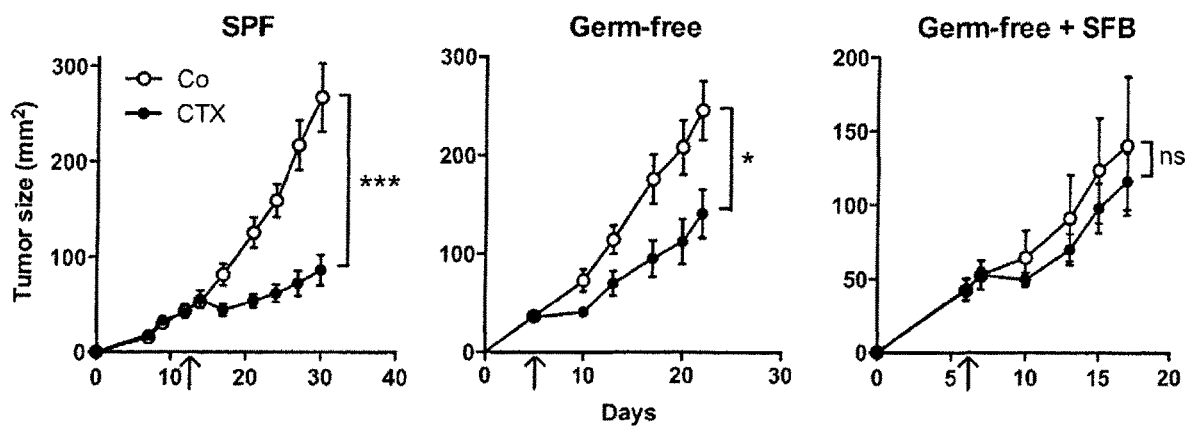
Figure 4C:
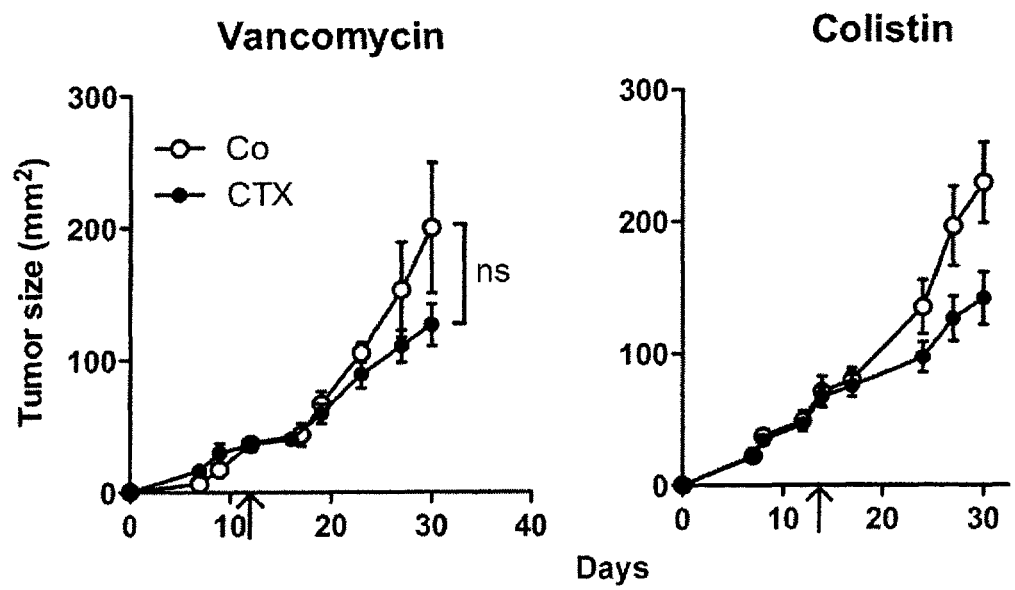
Figure 4D:
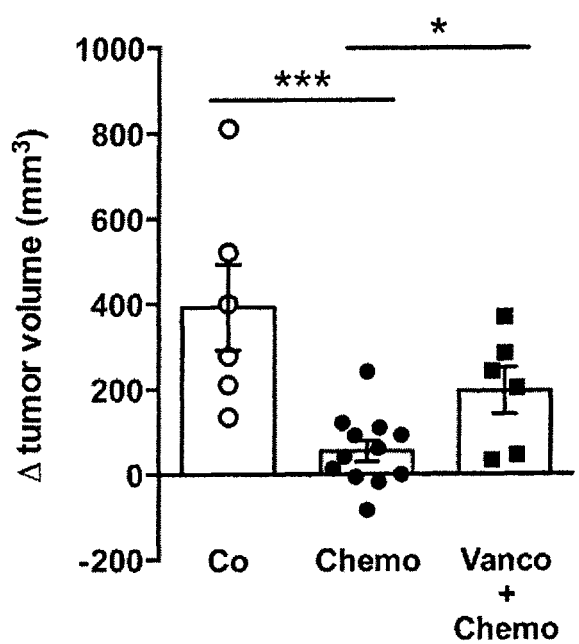
Figure 4E:
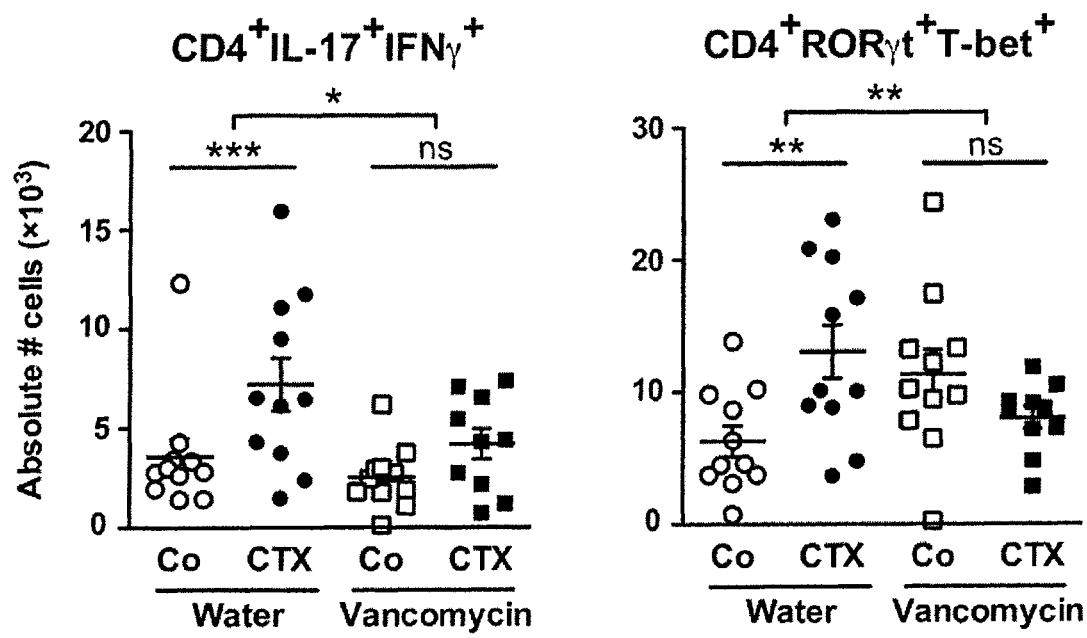
Figure 4F:
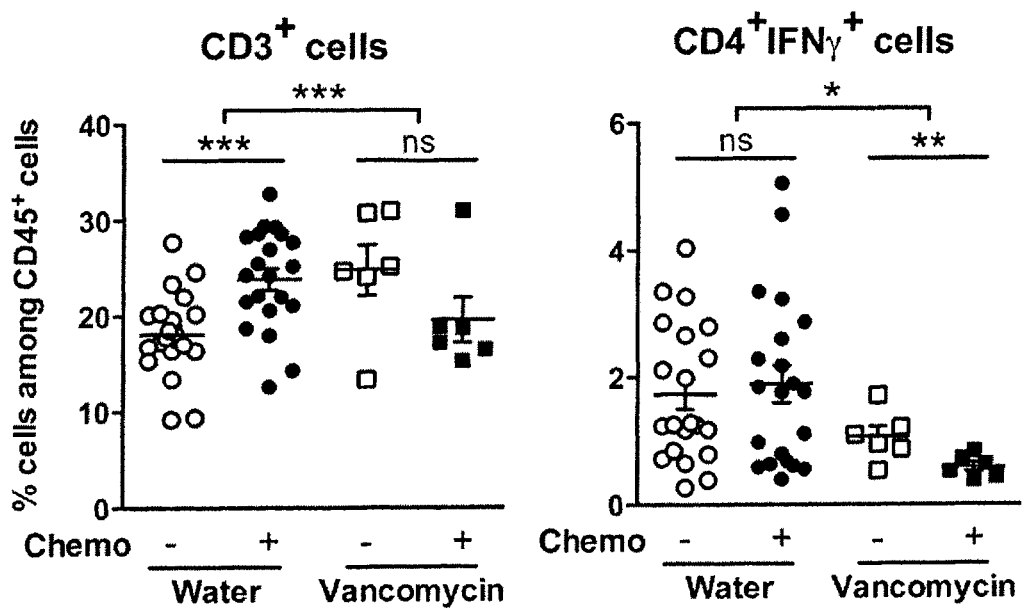

Because commensal bacteria modulate intestinal and systemic immunity post-CTX, the inventors further investigated the effect of antibiotics on CTX-mediated tumor growth inhibition. Long-term treatment with broad-spectrum ATB reduced the capacity of CTX to cure P815 mastocytomas established in syngenic DBA2 mice (FIG. 4A, FIG. 13A). Moreover, the antitumor effects mediated by CTX against MCA205 sarcomas were reduced in GF compared with SPF mice (FIG. 4B, left and middle panels). Driven by the observations that CTX mostly induced the translocation of Gram$^+$ bacteria and that Gram$^+$ bacteria correlated with splenic Th1/Th17 polarization, the inventors compared the capacity of several ATB regimens, namely vancomycin (depleting Gram$^+$ bacteria) and colistin (depleting most Gram$^-$ bacteria) to interfere with the tumor growth-inhibitory effects of CTX. Vancomycin, and to a lesser extent colistin compromised the anti-tumor efficacy of CTX against MCA205 sarcoma (FIG. 4C, FIG. 13B). Using a transgenic tumor model of autochthonous lung carcinogenesis driven by oncogenic K-Ras coupled to conditional p53 deletion (Cortez-Retamozo et al., 2013), the inhibitory role of vancomycin on the anticancer efficacy of a CTX-based chemotherapeutic regimen was confirmed (FIG. 4D). Vancomycin also prevented the CTX-induced accumulation of pTh17 in the spleen (FIG. 4E) and reduced the frequencies of tumor-infiltrating CD3$^+$ T cells and Th1 cells (FIG. 4F).

Although the feces of most SPF mice treated with ATB usually were free of cultivable bacteria (FIG. 9), some mice occasionally experienced the outgrowth of *Parabacteroides distasonis*, a species reported to maintain part of the intestinal regulatory T cell repertoire and to mediate local anti-inflammatory effects (Geuking et al., 2011; Kverka et al., 2011; Lathrop et al., 2011). This bacterial contamination was associated with the failure of an immunogenic chemotherapy (doxorubicin) against established MCA205 sarcomas (FIG. 14A). Moreover, experimental recolonization of ATB-sterilized mice with *P. distasonis* compromised the anticancer effects of doxorubicin (FIG. 14B), demonstrating that gut microbial dysbiosis abrogates anticancer therapy. Finally, monoassociation of tumor-bearing GF mice with SFB, which promotes Th17 cell differentiation in the LP (Hooper et al., 2012; Lee et al., 2012; Wu et al., 2010) also had a detrimental impact on the tumor growth-inhibitory effect of CTX (FIG. 4B, right panel).

Figure 4G:
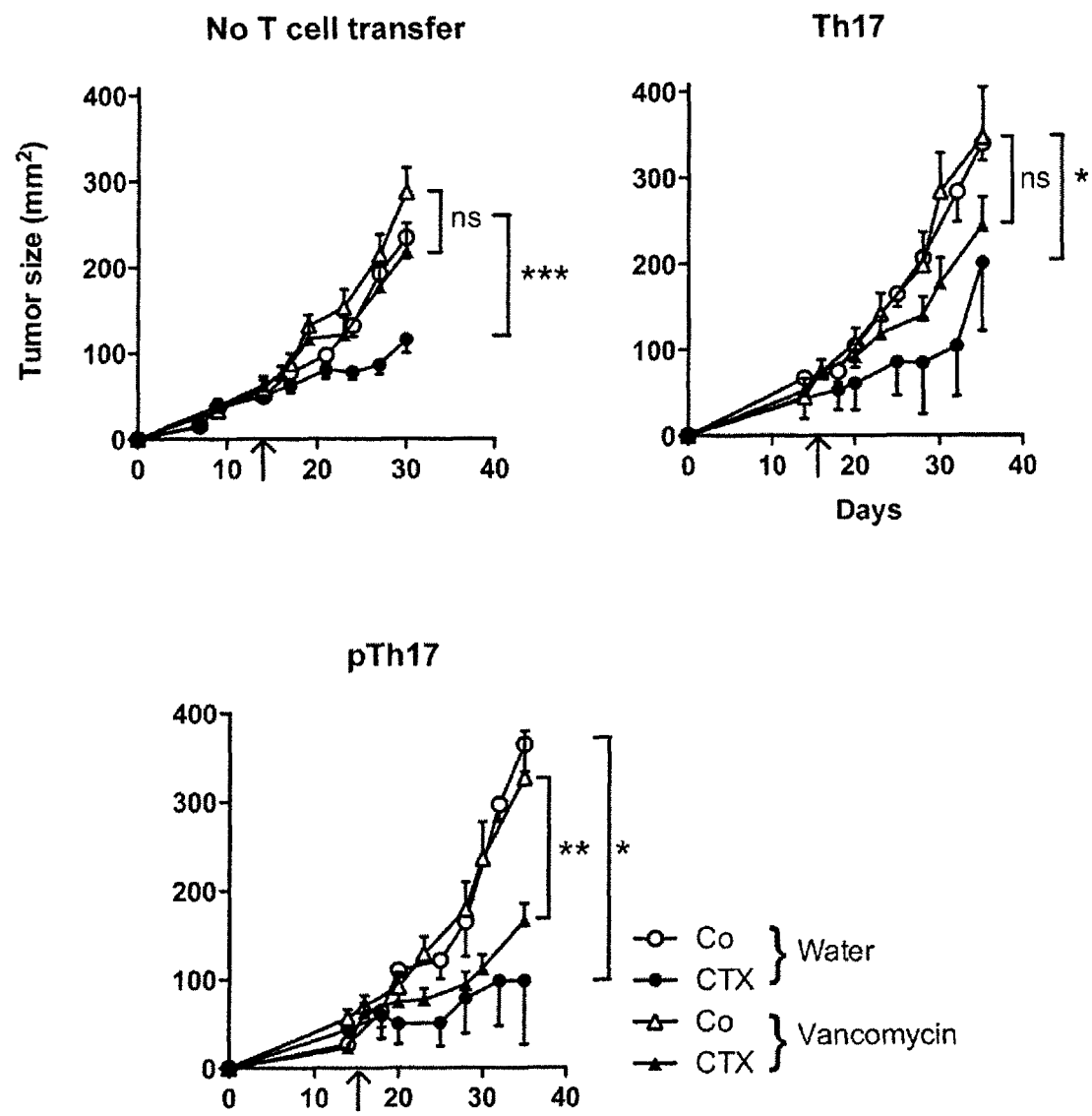

The aforementioned results highlight the association between specific CTX-induced alterations in gut microbiota, the accumulation of pTh17 cells in the spleen and the success of chemotherapy. To establish a direct causal link between these phenomena, the inventors adoptively transferred Th17 or pTh17 populations into vancomycin-treated mice and evaluated their capacity to reestablish the CTX-mediated tumor growth retardation. Ex vivo propagated pTh17 exhibited a pattern of gene expression similar to that expressed by CTX-induced splenic CD4$^+$ T cells in vivo (FIG. 15). Only pTh17 but not Th17 cells were able to rescue the negative impact of vancomycin on the CTX-mediated therapeutic effect (FIG. 4G). These results emphasize the importance of pTh17 cells for CTX-mediated anticancer immune responses.

To gain further insight into the links between gut microbiota and cellular anticancer-immunity, two distinct experimental approaches were used.

First, the inventors analyzed the impact of vancomycin on the microenvironment of auchthonous non-small cell lung cancers resulting from oncogenic activation of K-Ras and P53 and treated with CTX-based chemotherapy. They analyzed the impact of vancomycin on the infiltration of chemotherapy-treated tumor beds by γδT17 cells, which are known to be crucial for the recruitment of antitumor CTLs post-chemotherapy (Ma et al., 2011). In vancomycin- or broad-spectrum ATB-treated mice, tumor beds were devoid of γδT17 post-therapy in contrast to water-treated chemotherapy recipients (FIG. 17).

Secondly, they analyzed whether affecting gut microbiota with various antibiotic regimens could interfere with the elicitation of Th1 or Tc1 primary immune responses directed against a widely studied model antigen (chicken ovalbumin and its immunodominant H-$2^b$ restricted epitope) that were combined with the TLR3 agonist poly-(I:C) and injected into the foodpad of antibiotic-treated or untreated mice that received CTX. None of the antibiotics that were used was capable of inhibiting IFNγ production by draining lymph node cells. Similarly, IFNγ secretion triggered by restimulation with the H-$2^b$-restricted SIINFEKL immunodominant peptide of OVA was maintained in vancomycin-treated mice, suggesting that Th1 (or Tc1) immune responses are not affected by the gut microbiota (FIG. 18). So, in this model, the antibiotic-mediated elimination of commensal bacteria causes defects at the level of innate immunity (loss of γδT17 cells in the tumor microenvironment) that result in modulations of cognate antitumor immune responses (effector memory TILs) with a reduced $CD8^+$/Foxp3 ratio (FIG. 20) and blunted Th1 responses (FIG. 4).

Although much of the detailed molecular mechanisms governing the complex interplay between epithelial cells, gut microbiota and intestinal immunity remain to be deciphered, the present study unveils the unsuspected impact of the intestinal microbiota on chemotherapy-elicited anticancer immune responses. The above data underscore new risks associated with antibiotic medication during cancer treatments as well as the potential therapeutic utility of manipulating the gut microbiota.

Example 2: The Intestinal Microbiota Modulates the Anticancer Immune Effects of Cyclophosphamide—Results on a Preclinical Model Mimicking Human Tumorigenesis A transgenic tumor model of autochthonous NSCLC driven by oncogenic K-Ras coupled to a conditional P53 deletion (as initially described by T. Jacks, Cell 2012) was used to test the inhibitory role of vancomycin-based antibiotherapy on the anticancer efficacy of a combination of oxaliplatin plus CTX. In this preclinical model mimicking human tumorigenesis, the concept that the eradication of Gram-positive bacteria by vancomycin compromised the efficacy of CTX-based chemotherapy was validated (FIG. 19A and FIG. 4D), correlating with a reduced intratumoral $CD8^+$ T effector/$Foxp3^+$ regulatory T cell ratio (FIG. 19B).

Thus, Gram-positive bacteria appear to be necessary for the optimal efficacy of the CTX-induced anticancer immune response and tumor mass reduction.

Example 3: Human Results: Cyclophosphamide Induces Th1 and Th10 Immune Responses Directed Against Commensal Bacteria in Cancer Patients In order to further demonstrate that CTX induces bacterial translocation to secondary lymphoid tissues in humans as in mice, the inventors assessed memory $CD4^+$Th1 cell responses, in peripheral blood, specific for a series of bacteria in advanced cancer patients before and after treatment with metronomic cyclophosphamide (CTX). The responses that were monitored included those against enterococci (*E. hirae* and *E. faecalis*, both immunogenic in mice receiving CTX), lactobacilli (*L. johnsonii* and the less relevant *L. plantarum*), as well as against *E. coli*. The results were obtained from 6 patients with metastatic ovarian cancer treated with CTX+Avastin (Viaud et al., 2011), 3 NSCLC (non small cell lung cancer) patients treated with CTX before a DC-based exosome Phase II vaccine trial (Chaput et al., 2006), and 2 melanoma patients enrolled in a Phase I trial of targeted immunotherapy preceded by CTX (Chaput et al., 2013). From these 11 patients, 6 (54%) developed memory Th1 responses against enterococci, 2 against *L. johnsonii* (18%), 2 (18%) against *E. coli*, while one (9%) of them mounted a cellular immune response against *L. plantarum* (FIG. 20). Interestingly, some individuals elicited a Th10 immune response (i.e., IL-10 release which is often associated with tumor progression) against *E. faecalis* (high IL-10 & low IFNγ production, as Patients 5&6).

In summary, three patterns of cytokine release were observed in these experimental conditions: (i) no cytokine release, i.e., no memory response to commensals; (ii) memory response of a Th10 phenotype; and (iii) Memory response of a Th1 phenotype.

The inventors anticipate that only pattern 3 will be proned to benefit from chemotherapy, and they now correlate this anti-commensal bacterial immune response with clinical outcome. This pharmacodynamic assay is useful to predict, after 3-6 weeks (1-2 cycles of chemotherapy) whether such a CTX-based chemotherapy would trigger an adjuvant immune response and a clinical benefit.

Example 4: Human Results: Oxaliplatine-Based Chemotherapy Induces a Change in the Distribution of Bacterial Species in Gut Microbiota and an Increase of T-Bet Transcription by the Gut Microbiota During a surgery of debulking of a primary colon cancer, or pancreatic cancer or stomach cancer, it is conceivable to access the duodenum (for stomach and pancreatic tumors) or ileum (for right colon cancer). In such cases, mucosal samples can be scratched and harvested (for 16S rRNA gene pyrosequencing analyses and description of the mucosal microbiota composition at the different taxonomic levels as described above), as well as mucosa that can be kept frozen (in RNAzol for qRT-PCR) or in paraffin-embedded tissues (for immunohistochemistry analyses).

This surgery can be performed either before chemotherapy (adjuvant chemotherapy) or after chemotherapy (neoadjuvant chemotherapy).

In the present example, ileal mucosa from patients operated for a right colon cancer (6 patients in neoadjuvant oxaliplatine-based chemotherapy and 7 patients prior to therapy) were analyzed to compare the composition of ileal microbiota and the relative loss or gain of representativity of distinct genera and species (isolates) in cases of adjuvant versus neoadjuvant chemotherapy, meaning in colon cancer bearing patients that already received («chemo») or did not receive («controls») chemotherapy.

The distribution of bacteria at a species ($1^{st}$ relative isolates) level was significantly different in the ileum post-chemotherapy (principal component analyses, Monte Carlo test, p=0.018) (FIG. 21).

Like in mice, chemotherapy induced the decrease of species belonging to *Clostridium* cluster IV in almost all patients, more specifically of bacteria from the genera *Dorea, Coprococcus*, Lachnospiraceae, *Gemmiger, Alistipes*, and bacterial species *Faecalibacterium prausnitzii* (FIGS. 22 and 23, Table 3). In contrast, bacteria from the *Bifidobacterium* and *Lactobacillus* genera tended to increase post-chemotherapy (Table 3, FIG. 24).

TABLE 3

Differentially represented bacterial species (isolates) with p ≤ 0.1 between Chemo treated and non treated patients

| Bacetrial species | AV Chemo | AV_Control | SD Chemo | SD_Control | T-test p value | Classification_Genus |
|---|---|---|---|---|---|---|
| Bacteroidescaccae_JCM9498_EU136686 | 3.828 | 0.135 | 4.619 | 0.190 | 0.056 | *Bacteroides* |
| Flavonifractorplautii_17_GU968170 | 0.712 | 0.109 | 0.767 | 0.162 | 0.065 | Flavonifractor |
| Bifidobacteriumlongum_IMAUFB091_XI2813_JQ805709 | 0.530 | 0.029 | 0.653 | 0.076 | 0.067 | *Bifidobacterium* |
| Bilophilawadsworthia_L35148 | 0.195 | 0.023 | 0.242 | 0.061 | 0.092 | *Bilophila* |
| ClostridiumspAP4_JX101685 | 0.112 | 0.024 | 0.109 | 0.064 | 0.090 | unclassified_Ruminococcaceae |
| unidentifiedbacterium_CCCM26_AY654952 | 0.097 | 0.015 | 0.115 | 0.026 | 0.088 | unclassified_Clostridiales |
| ClostridiaceaebacteriumFH042_AB298771 | 0.053 | 0.000 | 0.070 | 0.000 | 0.068 | *Anaerovorax* |
| bacteriumNLAEzlC328_JQ608041 | 0.027 | 0.000 | 0.038 | 0.000 | 0.079 | *Bacteroides* |
| AlistipesspNML05A004_EU189022 | 0.000 | 0.023 | 0.000 | 0.024 | 0.028 | *Alistipes* |
| Doreaformicigenerans_SaLBHl10_JN093132 | 0.000 | 0.034 | 0.000 | 0.027 | 0.006 | Dorea |
| Bacteroidesuniformis_JCM5828T_AB050110 | 0.009 | 0.090 | 0.024 | 0.104 | 0.068 | *Bacteroides* |
| Clostridiumleptum_DSM753T_AJ305238 | 0.006 | 0.195 | 0.015 | 0.166 | 0.011 | *Clostridium* IV |
| butyrateproducingbacteriumSR1_1_AY305321 | 0.115 | 0.318 | 0.207 | 0.215 | 0.097 | *Blautia* |
| ClostridiaceaebacteriumDJF_LS13_EU728741 | 0.050 | 0.260 | 0.074 | 0.177 | 0.013 | Dorea |
| Clostridiumruminantium_LA1_EU089964 | 0.043 | 0.294 | 0.077 | 0.325 | 0.070 | *Clostridium* XI |
| ClostridialesbacteriumoraltaxonF32_VO026_HM099644 | 0.005 | 0.306 | 0.012 | 0.445 | 0.098 | *Acetivibrio* |
| unidentifiedeubacteriumcloneBSV28_AJ229190 | 0.068 | 0.440 | 0.126 | 0.521 | 0.091 | unclassified_Bacteria |
| butyrateproducingbacteriumA2231_AJ270484 | 0.047 | 0.438 | 0.087 | 0.438 | 0.039 | *Coprococcus* |
| BacteroidesspdnLKV2_JF813174 | 0.278 | 0.893 | 0.262 | 0.589 | 0.027 | *Bacteroides* |
| Gemmigerformicilis_ATCC27749_X256_GU562446 | 0.121 | 1.264 | 0.198 | 1.421 | 0.057 | *Gemmiger* |
| Alistipesputredinis_JCM16772_AB554232 | 0.000 | 1.171 | 0.000 | 1.319 | 0.037 | *Alistipes* |
| bacteriumIARFR184_KC153191 | 1.199 | 3.993 | 1.288 | 3.686 | 0.083 | Uncl Lachnospiraceae |
| Faecalibacteriumprausnitzii_A2165_AJ270469 | 1.167 | 4.820 | 1.585 | 3.226 | 0.020 | *Faecalibacterium* |

The inventors also investigated, in parallel to pyrosequencing analyses of 16SrRNA of gut microbiota of ileum, the transcriptional profiling of cytokines and transcription factors detectable in mucosae of patients receiving or not chemotherapy. This investigation was done by qRT-PCR from ileal mucosa from the same patients. While RORγt and IL-17 were not very different in both groups, T-bet was upregulated post-chemotherapy and in two patients that had high levels of *Bifidobacterium* and Lactobacilli post-chemotherapy, T-bet transcripts were rather high compared with the other patients, suggesting that a pTh17 T cell response had been elicited by the treatment.

Example 5: *E. hirae* is a pTH17/Th1 Bacteria, Alone or in Conjunction with Lactobacilli (*L. Johnsonii*) Inducing Probiotic Antitumor Effects To analyze the impact of distinct bacterial species (specifically those capable of translocation to the spleen post-CTX) on the priming of bacteria-specific pathogenic TH17 immune responses, the inventors treated C57BL/6 mice with broad spectrum ATB for 15 days (which sterilized the feces), performed an injection of CTX (100 mg/kg) followed by oral gavage with $10^9$ *E. hirae*±$10^9$ *L. johnsonii*. Six days post-bacteria mono- or bi-association, splenocytes were harvested for a flow cytometric analysis focusing on IFNγ+ or CXCR3+ T cells among TH17 cells (called "pTH17" henceforth) (FIG. 25A) that could arise from CD3+CD4+ RORγτ+ or CCR6+ T cells (called "TH17" henceforth) (FIG. 25B) and could give rise to bona fide CD3+CD4+ IFNγ+ or CXCR3+ T cells (called TH1 cells henceforth) (FIG. 25C). The obtained data revealed that *E. hirae* but not *L. johnsonii* was the dominant bacterium mediating a TH1 and a pTH17 response in the spleen post-CTX, that could be further magnified in the presence of *L. johnsonii* (FIG. 25A, 25C). In addition, the inventors now bring up evidence for a cause-effect relationship between the presence of a cocktail of Gram-positive bacteria (*L. johnsonii*+*E. hirae*) in the small intestine and, not only the mere elicitation of systemic pTH17 cells (FIG. 25), but also the partial restoration of CTX-induced antitumor effects in ATB-treated mice (FIG. 26).

Example 6: *E. hirae* Enhanced the Anticancer Immune Response In Vivo

To investigate whether cognate TH responses directed against *E. hirae* could promote anticancer T cell responses, two distinct preclinical models were set up.

First, tumor cell lines genetically modified to express the ovalbumin antigen (OVA) (the fibrosarcoma MCA205 OVA) have been implanted sc. after a 14 day-broad spectrum ATBs therapy (or saline as control). Animals have been adoptively transferred with $OVA_{323-339}$ specific MHC class II-restricted OTII TCR transgenic T cells, and treated with CTX (or saline). The inventors monitored the "clinical" impact of oral gavage with *E. hirae* on the expansion and activation of syngeneic CD45.1+ T cells and congenic CD45.2+ OTII cells in the spleen and in tumor beds (experimental setting presented in FIG. 27A). In the spleen, they confirmed the *E. hirae*-induced expansion of host (CD45.1+) splenocytes (FIG. 27B, left panel), due at least in part to the proliferation of CD4+ T cells (FIG. 27B, middle panel) accompanied by the accumulation of pTH17 cells (FIG. 27B, right panel). Indeed, they demonstrated the *E. hirae*-mediated division, accumulation and differentiation into memory T cells of the adoptively transferred CD45.2 OTII cells in the spleen (FIG. 27C). Moreover, CD45.2+ T cells were recovered from the tumor beds, acquired CD44 molecules and proliferated almost as efficiently as host TILs in the context of oral feeding with *E. hirae* (FIG. 27D-F).

Secondly, to mimic a clinically relevant mouse model, we set up and reported original orthotopic models of head and neck and lung cancers using the TC1 cell lines expressing the human papillomavirus 16 (HPV16) E7 (F. Sandoval et al., 2013). Tumor regression could be obtained by vaccinating mice using a nonreplicative delivery system composed of the B subunit of Shiga toxin coupled to E7 antigen (SBxT-E7) as a mucosal vector. Vingert et al. reported that only intranasal vaccination targeting CD103+ DC residing in the thoracic LN (and not the macrophages) could elicit polyfunctional $D^b_{-E739-47}$ tetramer binding CD8+T cells expressing mucosal integrins (CD49a and CD103) (B. Vingert et al., 2006). The experimental setting of this experiment is presented in FIG. 28A. In a sc. TC1 model, tumor growth could be significantly reduced by the combination of SBxT-E7 and CTX, eventually leading to complete tumor eradication (FIG. 28B-C). The negative impact of broad spectrum ATB on the efficacy of the vaccine is depicted in FIG. 28B-C where the percentages of animals completely rejecting their TC1 tumors was drastically reduced. Next, the "clinical" impact of oral gavage with *E. hirae* on the expansion of polyfunctional $D^b$ E739-47 tetramer binding CD8+T cells in the spleens was monitored. Indeed, *E. hirae* restored the expansion of $D^b_{-E739-47}$ tetramer binding CD8+T cells in mice that had rejected their tumors (but not in the others), as shown in non ATB/CTX-treated positive controls (FIG. 28D).

Altogether, monoassociation of gut sterilized mice with *E. hirae* could partially restore CTX-induced anticancer immune responses, keeping in check tumor progression.

Example 7: Comparisons Between Various Clones of *E. hirae* (for pTH17, for Caco-2 Anti-Apoptotic Effects)

Up to 13 other *E. hirae* isolates/clones were tested to analyze their differential immunogenicity in vivo and capacity to mediate such "an anticancer probiotic" property. The alignment of the bacterial genomic patterns of various clones of *E. hirae* analyzed in pulsed-field gel electrophoresis (PFGE) (FIG. 29) revealed that the clone initially isolated by the inventors (clone "Villejuif", which was deposited on Nov. 7, 2013 at the Collection Nationale de Cultures de Microorganismes de l'Institut Pasteur, Paris (CNCM), under the number I-4815) differs from many others in terms of genomic sequences. One human isolate (clone 708) exhibited greater TH1 and Tc1 potential than the clone CNCM I-4815 (FIG. 30). However, clone 708 did not perform better than the CNCM I-4815 clone for the anticancer probiotic effect in CTX-treated established MCA205 sarcomas (not shown). Sequence and functional differences inbetween various *E. hirae* isolates were corroborated in an in vitro assay aimed at monitoring LDH release (featuring cell death) and human β2 defensin secretion from the Caco-2 epithelial intestinal cell line exposed to CTX+/− various clones of *E. hirae* or *E. coli*. While clone CNCM I-4815 and clone 708 could prevent CTX-induced Caco-2 cell death by, most likely, promoting the production of antimicrobial peptide β2 defensin, *E. coli* failed to do so (not shown).

Example 8: TLR4, Nod1 and Nod2 Prevent CTX-Mediated Bacterial Translocation, pTH17 Elicitation and Tumoricidal Activity To analyze which gut immune checkpoints could keep in check bacterial translocation during a therapy with alkylating agents, the inventors investigated the role of major pattern recognition receptors regulating intestinal homeostasis in the elicitation of splenic pTH17 cells and in tumor control promoted by CTX in MCA205-breaing C57BL/6 mice.

Bacterial translocation analyzed by culturing bacterial colonies from spleens in anaerobic conditions, known to primarily allow the proliferation of *E. hirae* and *L. johnsonii* (Viaud et al., Science November 2013), was enhanced in NOD1×NOD2$^{-/-}$ (FIG. 31A). In addition, the priming of splenic pTH17 cells following CTX administration was augmented in NOD2$^{-/-}$ mice (while it was abrogated in Myd88$^{-/-}$ animals compared with wild type (WT) mice, Viaud et al. Science 2013) (FIG. 31B). In accordance with these findings obtained using gene deficient animals, the inventors phenocopied these effects using pharmacomimetics, i.e., ligands for NOD1 and NOD2, the peptidoglycans myramyl dipeptide and TriDAP, which acted locally by promoting the release of the antimicrobial peptide lipocalin-2 in stools (FIG. 31D), thereby reducing CTX-mediated pTH17 in the spleen (FIG. 31C).

These results were corroborated in another experimental system where broad spectrum ATB-treated mice were reconstituted by oral gavage of *E. hirae* and treated with CTX before a kinetic monitoring of bacterial translocation in mesenteric LN. In this setting, it was indeed shown that the frequencies of *E. hirae* colonies recovered post-CTX in mLN and the incidence of growth in anaerobic conditions was increased in TLR4, NOD1 and NOD2 KO mice (not shown). Accordingly, the elicitation of CTX-induced pTH17 cells following oral gavage with Gram+ bacteria in ATB-treated recipients was dramatically reduced in the presence of a TLR4 agonist (LPS or *E. coli*) (FIG. 32B) while CTX-induced TH1 and Tc1 cells were not affected (FIG. 32A).

The immune-dependent anti-sarcoma effects mediated by CTX were not ameliorated in single knock out mice (NOD1 or NOD2 or RIP2 or CARD15) compared with WT counterparts (FIG. 33A-C) but were significantly enhanced in NOD1$^{-/-}$×NOD2$^{-/-}$ mice (FIG. 33 D-E). Moreover, providing exogenous *E. coli* or LPS to oral gavage with *E. hirae*+*L. johnsonii* in ATB-treated mice severely compromised the anticancer probiotic effects of the Gram+ bacteria (FIG. 34A-B), supporting the notion that TLR4 signaling prevents translocation, and therefore pTH17 accumulation and subsequent antitumor effects.

Figure 35A:
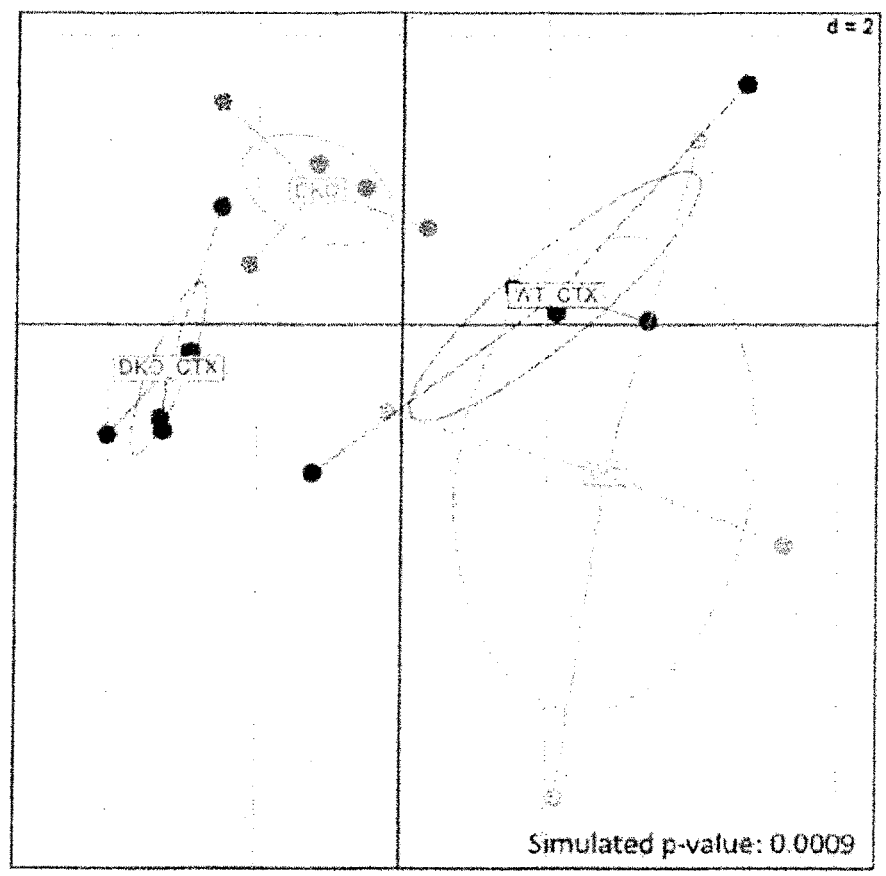
Figure 35A:
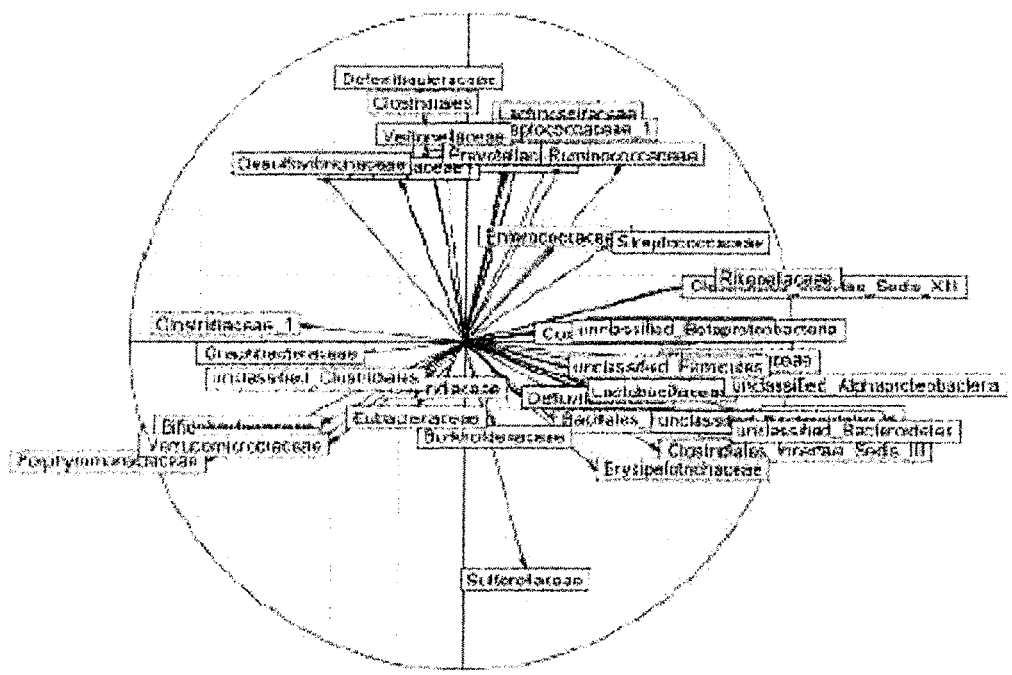
Figure 35B:
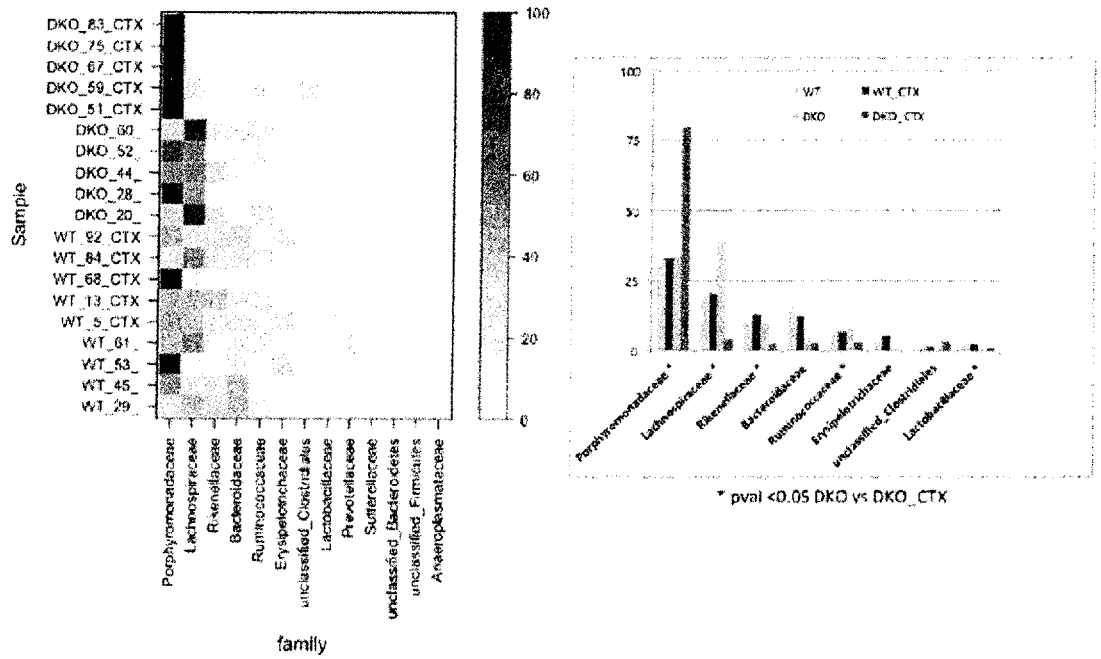
Figure 35C:
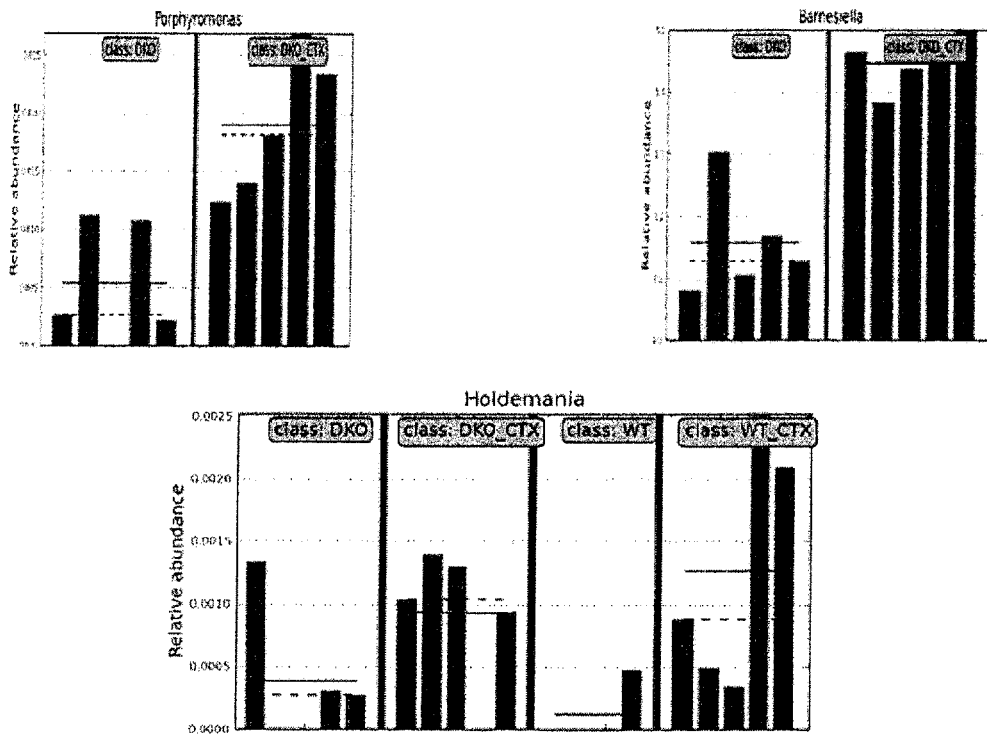

Example 9: Beneficial Dysbiosis in Nod1$^{-/-}$× Nod2$^{-/-}$ Mice Associated with Increased Tumoricidal Activity of CTX Pyrosequencing analyses of 16S rRNA gene amplicons from both biofilms of the small intestine and stool harvested from WT versus NOD1$^{-/-}$×NOD2$^{-/-}$ naïve mice were performed seven days post-CTX or PBS administration. Principle coordinate analysis revealed that bacterial community structures were significantly different inbetween CTX groups from WT versus gene deficient mice (FIG. 35-36 for the phyla and genera, FIG. 40 for the OTU). There was an overrepresentation of Clostridiaceae in the small intestines (SI) (FIG. 36 A-B), mainly attributable to Segmented filamentous bacteria (FIG. 40) and of Porphyromonadaceae (mainly *Barnesiella*) in the stool (FIG. 35A-B) with a relative loss of Erysipelotrichaceae in SI (FIG. 36 A-B) and of Lachnospiraceae in feces of NOD1$^{-/-}$×NOD2$^{-/-}$ naïve mice receiving CTX compared with PBS (FIG. 35A-B).

Reconstitution of ATB-sterilized mice with a bi-association of *E. hirae*+*Clostridium perfringens* mediated additive/synergistic anticancer probiotic effects in CTX-treated mice (FIG. 37). In mammals, a combination of *E. hirae* with a non pathobiontic *clostridium* such as SFB or a *Barnesiella* or a *Holdemania* is as efficient as the combination *E. hirae*+*C. perfringens* and less toxic.

Example 10: Gram Negative Bacteria are Mandatory for Anticancer Memory T Cell Responses Taking into account the overrepresentation of Gram negative OTU isolated in NOD1xNOD2 double knock out mice that exhibited a better anticancer response, the inventors addressed the role of Gram negative bacteria in the long term protection generated using an OVA-based cancer vaccine used in conjunction with CTX. Broad spectrum ATB prevented the long term protection of a cancer vaccine against a lethal challenge with OVA-engineered tumor cells. Interestingly, vancomycine did not prevent the vaccine from immunizing the animal while colistine, which killed Gram negative bacteria, did (FIG. 38). It can be concluded that CTX can mobilize Gram negative gut adjuvant to boost tumor vaccines.

Example 11: Antibiotic Regimen Ameliorating the CTX-Mediated Antitumor Effects Since dysbiosis mediated or enforced by NOD genetic defects could ameliorate the therapeutic success of CTX, the inventors addressed whether distinct ATB regimen, as described in Zhang Y et al. (2014), could positively affect tumor outgrowth. Indeed, protocols reported to reduce Firmicutes, most specifically Clostridiae eventually decreasing the Firmicutes/Bacteroides ratio (such as the combination of neomycine+cephalothin or vancomycine+imipenem) (FIG. 39 C-D) could improve the CTX-induced antitumor effects while cifloxacin (which, in contrast, induced a marked suppression of Bacteroidetes) was not efficient (FIG. 39B). Of note, the combination of neomycine+cephalothin could augment SFB representation while vanco+imipenem increased that of *Porphyromonas* (Zhang Y et al., 2014).

REFERENCES

Apetoh, L. et al. (2007) Toll-like receptor 4-dependent contribution of the immune system to anticancer chemotherapy and radiotherapy. Nat Med, 13, 1050-1059.

Arrntzen E H, (2008), Cancer Immunol Immunother 57 (10): 1559

Bottger, E. C. (1989) Rapid determination of bacterial ribosomal RNA sequences by direct sequencing of enzymatically amplified DNA. FEMS Microbial Lett, 53, 171-176.

Caporaso, J. G. et al. (2010). QIIME allows analysis of high-throughput community sequencing data. Nat Methods, 7, 335-336.

Chaput, N. et al. (2013) Phase I clinical trial combining imatinib mesylate and IL-2: HLA-DR NK cell levels correlate with disease outcome. Oncoimmunology, 2, e23080.

Chaput, N. et al. (2006) Dendritic cell derived-exosomes: biology and clinical implementations. J Leukoc Biol, 80, 471-478.

Caux C et al. (1996), J Exp Med, 184 (2): 695.

Cole, J. R., et al. (2009) The Ribosomal Database Project: improved alignments and new tools for rRNA analysis. Nucleic Acids Res, 37, D141-145.

Cong, Y. et al. (2009) A dominant, coordinated T regulatory cell-IgA response to the intestinal microbiota. Proc Natl Acad Sci USA, 106, 19256-19261.

Cortez-Retamozo, V. et al. (2012). Origins of tumor-associated macrophages and neutrophils. Proc Natl Acad Sci USA, 109, 2491-2496.

Cortez-Retamozo, V. et al. (2013). Angiotensin II drives the production of tumor-promoting macrophages. Immunity, 38, 296-308.

Darfeuille-Michaud, A. et al. (2004) High prevalence of adherent-invasive *Escherichia coli* associated with ileal mucosa in Crohn's disease. Gastroenterology, 127, 412-421.

Demidenko, E. (2006) The assessment of tumour response to treatment. Journal of the royal statistical society series C-applied statistics, 55, 365.

Dzutsev A, et al. (2014) The role of the microbiota in inflammation, carcinogenesis, and cancer therapy. Eur J Immunol. 2014 Oct. 18. doi: 10.1002/eji.201444972. [Epub ahead of print] PubMed PMID: 25328099.

Furet, J. P. et al. (2009). Comparative assessment of human and farm animal faecal microbiota using real-time quantitative PCR. FEMS Microbial Ecol, 68, 351-362.

Furet, J. P., et al. (2010). Differential adaptation of human gut microbiota to bariatric surgery-induced weight loss: links with metabolic and low-grade inflammation markers. Diabetes, 59, 3049-3057.

Geuking, M. B., et al. (2011) Intestinal bacterial colonization induces mutualistic regulatory T cell responses. Immunity, 34, 794-806.

Ghiringhelli, F., et al. (2004) CD4+CD25+ regulatory T cells suppress tumor immunity but are sensitive to cyclophosphamide which allows immunotherapy of established tumors to be curative. Eur J Immunol, 34, 336-344.

Ghoreschi, K. et al. (2010). Generation of pathogenic T(H) 17 cells in the absence of TGF-beta signalling. Nature, 467, 967-971.

Grivennikov, S. I. et al. (2012). Adenoma-linked barrier defects and microbial products drive IL-23/IL-17-mediated tumour growth. Nature, 491, 254-258.

Heinze, G. (2006) A comparative investigation of methods for logistic regression with separated or nearly separated data. Stat Med, 25, 4216-4226.

Helsel, D. R. (2005) Nondectects and Data Analysis; Statistics for censored environmental data. John Wiley and Sons, USA, NJ.

Hooper, L. V. et al. (2012). Interactions between the microbiota and the immune system. Science, 336, 1268-1273.

Hugenholtz, P., et al. (2001) Investigation of candidate division TM7, a recently recognized major lineage of the domain Bacteria with no known pure-culture representatives. Appl Environ Microbiol, 67, 411-419.

Joossens, M., et al. (2011). Dysbiosis of the faecal microbiota in patients with Crohn's disease and their unaffected relatives. Gut, 60, 631-637.

Kroemer, G., et al. (2013). Immunogenic cell death in cancer therapy. Annu Rev Immunol, 31, 51-72.

Kverka, M., et al. (2011) Oral administration of *Parabacteroides distasonis* antigens attenuates experimental murine colitis through modulation of immunity and microbiota composition. Clin Exp Immunol, 163, 250-259.

Lathrop, S. K., et al. (2011). Peripheral education of the immune system by colonic commensal microbiota. Nature, 478, 250-254.

Lee, Y., et al. (2012). Induction and molecular signature of pathogenic TH17 cells. Nat Immunol, 13, 991-999.

Lee, Y. K., et al. (2011). Proinflammatory T-cell responses to gut microbiota promote experimental autoimmune encephalomyelitis. Proc Natl Acad Sci USA, 108 Suppl 1, 4615-4622.

Lepage, P., et al. (2005). Biodiversity of the mucosa-associated microbiota is stable along the distal digestive tract in healthy individuals and patients with IBD. Inflamm Bowel Dis, 11, 473-480.

Lesterhuis W J, (2008) Crit Rev Oncol Hematol, 66, 118

Ley, R. E., et al. (2005). Obesity alters gut microbial ecology. Proc Natl Acad Sci USA, 102, 11070-11075.

Li, W. and Godzik, A. (2006) Cd-hit: a fast program for clustering and comparing large sets of protein or nucleotide sequences. Bioinformatics, 22, 1658-1659.

Ma, Y., et al. (2011). Contribution of IL-17-producing gamma delta T cells to the efficacy of anticancer chemotherapy. J Exp Med, 208, 491-503.

Manichanh, C., et al. (2006) Reduced diversity of faecal microbiota in Crohn's disease revealed by a metagenomic approach. Gut, 55, 205-211.

Mayeur, C., et al. (2013). Faecal D/L lactate ratio is a metabolic signature of microbiota imbalance in patients with short bowel syndrome. PLoS One, 8, e54335.

Michaud, M., et al. (2011). Autophagy-dependent anticancer immune responses induced by chemotherapeutic agents in mice. Science, 334, 1573-1577.

Newton, E. and Rudel, R. (2007) Estimating correlation with multiply censored data arising from the adjustment of singly censored data. Environ Sci Technol, 41, 221-228.

Palucka K, (2013) Curr Opin Immunol 25 (3): 396

Rice, L. B. (2006) Antimicrobial resistance in gram-positive bacteria. Am J Infect Control, 34, S11-19; discussion S64-73.

Romesburg, H. C. (1985) Exploring, confirming and randomization tests. Computers and Geosciences, 11, 19.

Sallusto F, (1994) J Exp Med 179: 1109.

Sandoval F. et al. (2013), Mucosal imprinting of vaccine-induced CD8(+) T cells is crucial to inhibit the growth of mucosal tumors. Science translational medicine 5, 172ra20.

Schlitzer, A., et al. (2013). IRF4 transcription factor-dependent CD11b+ dendritic cells in human and mouse control mucosal IL-17 cytokine responses. Immunity, 38, 970-983.

Seksik, P., et al. (2003) Alterations of the dominant faecal bacterial groups in patients with Crohn's disease of the colon. Gut, 52, 237-242.

Sobhani, I., et al. (2011). Microbial dysbiosis in colorectal cancer (CRC) patients. PLoS One, 6, e16393.

Sokol, H., et al. (2006) Specificities of the fecal microbiota in inflammatory bowel disease. Inflamm Bowel Dis, 12, 106-111.

Sugar, E., et al. (2012). Reporting of preclinical tumor-graft cancer therapeutic studies. Cancer Biol Ther, 13, 1262-1268.

Turnbaugh, P. J., et al. (2009) A core gut microbiome in obese and lean twins. Nature, 457, 480-484.

Ubeda, C., et al. (2010). Vancomycin-resistant *Enterococcus* domination of intestinal microbiota is enabled by antibiotic treatment in mice and precedes bloodstream invasion in humans. J Clin Invest, 120, 4332-4341.

Vanlint S, (2014) Cancer Immunol Immunother, 63 (9): 959.

van Vliet, M. J., et al. (2010). The role of intestinal microbiota in the development and severity of chemotherapy-induced mucositis. PLoS Pathog, 6, e1000879.

Viaud, S., et al. (2011). Cyclophosphamide induces differentiation of Th17 cells in cancer patients. Cancer Res. 71(3), 661-665.

Viaud, S. et al. (2013), The intestinal microbiota modulates the anticancer immune effects of cyclophosphamide. Science 342(6161): 971-6.

Viaud S, et al. (2014). Harnessing the intestinal microbiome for optimal therapeutic immunomodulation. Cancer Res. 2014 Aug. 15; 74(16):4217-21. doi: 10.1158/0008-5472.CAN-14-0987. Epub 2014 Jul. 29. PubMed PMID: 25074615.

Viaud S, et al. (2014). Gut microbiome and anticancer immune response: really hot Sh*t! Cell Death Differ. 2014 May 16. doi: 10.1038/cdd.2014.56. [Epub ahead of print] Review. PubMed PMID: 24832470.

Viaud S, et al. (2014). Why should we need the gut microbiota to respond to cancer therapies? Oncoimmunology. 2014 Jan. 1; 3(1):e27574. Epub 2014 Jan. 17. PubMed PMID: 24800167; PubMed Central PMCID: PMC4006853.

Vingert B. et al. (2006). The Shiga toxin B-subunit targets antigen in vivo to dendritic cells and elicits anti-tumor immunity. European journal of immunology 36, 1124.

Wu, H. J., et al. (2010). Gut-residing segmented filamentous bacteria drive autoimmune arthritis via T helper 17 cells. Immunity, 32, 815-827.

Wu, N., et al. (2013). Dysbiosis signature of fecal microbiota in colorectal cancer patients. Microb Ecol, 66, 462-470.

Wu, S., et al. (2009) A human colonic commensal promotes colon tumorigenesis via activation of T helper type 17 T cell responses. Nat Med, 15, 1016-1022.

Yang, J., et al, (2013). The changes induced by cyclophosphamide in intestinal barrier and microflora in mice. Eur J Pharmacol, 714, 120-124.

Yin, Y., et al. (2013). Comparative analysis of the distribution of segmented filamentous bacteria in humans, mice and chickens. Isme J, 7, 615-621.

Zhang Y et al. (2014) Toxicology and Applied Pharmacology 277: 138-145.

Zitvogel, L., et al. (2008) Immunological aspects of cancer chemotherapy. Nat Rev Immunol, 8, 59-73.

Zwielehner, J., et al. (2011). Changes in human fecal microbiota due to chemotherapy analyzed by TaqMan-PCR, 454 sequencing and PCR-DGGE fingerprinting. PLoS One, 6, e28654.

The invention claimed is:

1. A method of treating cancer in a human subject in need thereof, comprising administering to the subject: (a) a probiotic composition comprising an amount of an *Enterococcus hirae* strain; and (b) dose(s) of an alkylating chemotherapeutic agent, wherein the administering of the probiotic composition and the alkylating chemotherapeutic agent to the subject induces a T-bet/Th1 local and systemic immune response, thereby treating the cancer in the subject.

2. The method of claim 1, wherein the probiotic composition further comprises at least one additional bacteria selected from the group consisting of *Porphyromonas, Barnesiella* and *Holdemania*.

3. The method of claim 2, wherein the probiotic composition further comprises *Lactobacillus johnsonii*.

4. The method of claim 1, wherein the probiotic composition is formulated for oral administration.

5. The method of claim 1, wherein the probiotic composition is administered to the subject after administration the administering of the alkylating chemotherapeutic agent.

6. The method of claim 1, wherein the subject has a dysbiosis with an under-representation of bacteria species, and wherein the bacteria species is present in the probiotic composition.

7. The method of claim 1, wherein the probiotic composition is administered to the subject after administration of a broad-spectrum antibiotic.

8. The method of claim 1, wherein the *Enterococcus hirae* strain is *Enterococcus hirae* strain 13144 Villejuif deposited at the Collection Nationale de Cultures de Microorganismes (CNCM), under the number I-4815, on Nov. 7, 2013.

9. The method of claim 1, wherein the alkylating chemotherapeutic agent is cyclophosphamide (CTX).

10. The method of claim 1, wherein the alkylating chemotherapeutic agent is oxaliplatin.

11. A method of treating cancer in a human subject in need thereof, comprising administering to the subject: (a) a probiotic composition comprising an *Enterococcus hirae* strain; and (b) an alkylating chemotherapeutic agent, to thereby treat the cancer; wherein said *Enterococcus hirae* strain is one which mediates a TH1 and a pTH17 response in the spleen of C57BL/6 mice treated with broad-spectrum antibiotics for a period of 15 days, followed by administration of said alkylating chemotherapeutic agent in combination with oral gavage delivering $10^9$ bacteria from of said *Enterococcus hirae* strain.

12. The method of claim 11, wherein the probiotic composition further comprises at least one additional bacteria selected from the group consisting of *Porphyromonas, Barnesiella* and *Holdemania*.

13. The method of claim 12, wherein the probiotic composition further comprises *Lactobacillus johnsonii*.

14. The method of claim 11, wherein the probiotic composition is formulated for oral administration.

15. The method of claim 11, wherein the probiotic composition is administered to the subject after the administering of the alkylating chemotherapeutic agent.

16. The method of claim 11, wherein the subject has a dysbiosis with an under-representation of bacteria species, and wherein the bacteria species is present in the probiotic composition.

17. The method of claim 11, wherein the probiotic composition is administered to the subject after administration of a broad-spectrum antibiotic.

18. The method of claim 11, wherein the *Enterococcus hirae* strain is *Enterococcus hirae* strain 13144 Villejuif deposited at the Collection Nationale de Cultures de Microorganismes (CNCM), under the number I-4815, on Nov. 7, 2013.

19. The method of claim 11, wherein the alkylating chemotherapeutic agent is cyclophosphamide (CTX).

20. The method of claim 11, wherein the alkylating chemotherapeutic agent is oxaliplatin.

\* \* \* \* \*

UNITED STATES PATENT AND TRADEMARK OFFICE
CERTIFICATE OF CORRECTION

PATENT NO. : 10,646,521 B2  
APPLICATION NO. : 15/038073  
DATED : May 12, 2020  
INVENTOR(S) : Laurence Zitvogel et al.

Page 1 of 1

It is certified that error appears in the above-identified patent and that said Letters Patent is hereby corrected as shown below:

On the Title Page

At item (71) delete "INSTITUT DE LA RECHERCHE AGRONOMIQUE" and add --INSTITUT NATIONAL DE LA RECHERCHE AGRONOMIQUE--

At item (73) delete "INSTITUT DE LA RECHERCHE AGRONOMIQUE" and add --INSTITUT NATIONAL DE LA RECHERCHE AGRONOMIQUE--

In the Claims

Column 57, Lines 29-30 delete "after administration the administering" and add --after the administering--

Signed and Sealed this  
Twenty-first Day of July, 2020

Andrei Iancu  
*Director of the United States Patent and Trademark Office*